(12) United States Patent
Chang et al.

(10) Patent No.: US 9,689,009 B2
(45) Date of Patent: *Jun. 27, 2017

(54) MICROORGANISM PRODUCING O-PHOSPHOSERINE AND METHOD OF PRODUCING L-CYSTEINE OR DERIVATIVES THEREOF FROM O-PHOSPHOSERINE USING THE SAME

(75) Inventors: Jin Sook Chang, Seoul (KR); Jae Hyun Jo, Seoul (KR); Hyun Ae Bae, Incheon (KR); Byeong Cheol Song, Uiwang-si (KR); Sol Kim, Seoul (KR); Hye Won Kim, Seongnam-si (KR); Hye Won Um, Suwon-si (KR); Sung Hoo Jhon, Seoul (KR); Yong Uk Shin, Yongin-si (KR); Eun Bin Yang, Seoul (KR); Kyoung Min Lee, Seoul (KR); Soo An Shin, Seoul (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 11 days.

This patent is subject to a terminal disclaimer.

(21) Appl. No.: 13/278,106

(22) Filed: Oct. 20, 2011

(65) Prior Publication Data

US 2012/0190083 A1 Jul. 26, 2012

(30) Foreign Application Priority Data

Oct. 20, 2010 (KR) ................. 10-2010-0102664
Aug. 26, 2011 (KR) ................. 10-2011-0086081

(51) Int. Cl.
| | |
|---|---|
| C12P 13/12 | (2006.01) |
| C12P 13/06 | (2006.01) |
| C12N 9/10 | (2006.01) |
| C12N 9/16 | (2006.01) |
| C12N 15/70 | (2006.01) |
| C12N 15/77 | (2006.01) |

(52) U.S. Cl.
CPC ............ *C12P 13/12* (2013.01); *C12N 9/1085* (2013.01); *C12N 9/16* (2013.01); *C12N 15/70* (2013.01); *C12N 15/77* (2013.01); *C12P 13/06* (2013.01); *C12Y 205/01065* (2013.01); *C12Y 301/03003* (2013.01)

(58) Field of Classification Search
USPC ............ 435/193, 69.1, 15, 113, 320.1, 252.3
See application file for complete search history.

(56) References Cited

U.S. PATENT DOCUMENTS 6,579,705 B2   6/2003 Maier et al.
7,083,952 B2 * 8/2006 Ziegler et al. ................. 435/116

FOREIGN PATENT DOCUMENTS

| EP | 0943687 | * | 9/1999 |
|---|---|---|---|
| EP | 0885962 B1 | | 4/2005 |
| EP | 0943687 B1 | | 1/2006 |
| KR | 10-0620092 | | 6/2006 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sousa et al., Microbiology 148(Pt5):1291-1303, 2002.*
Branch, A., TIBS 23:45-50, 1998.*
Agren et al., FEBS Letters 583:330-336, 2009.*
Ravnikar et al., Journal of Bacteriology 169(6):2611-2617, 1987.*
Wanner et al., FEMS Microbiology Letters 100:133-140, 1992.*
Peters-Wendisch et al., Applied and Environmental Microbiology 71(11):7139-7144, 2005.*
Duncan et al., Biochem. J. 234:49-57, 1986.*
Ryu et al., Process Biochemistry 32(3):201-209, 1997.*
Witt et al., Analytical Biochemistry 66:253-258, 1975).*
Inouye et al., Journal of Bacteriology 146(2):668-675, 1981.*
Fraser et al., FEBS Letters 455:344-348, 1999.*
Sadowski et al., Current Opinion in Structural Biology 19:357-362, 2009.*
Agren et al., Journal of Biological Chemistry 283(46):31567-31574, 2008.*
Walton SP, FEBS J. 277(23):4806-4813, 2010.*
Reuter et al., BMC Bioinformatics 11:29, 2010.*
Grant et al., Biochemistry 39:7316-7319, 2000.*
Fleischmann et al., Genbank accession No. ABK70074, Mar. 2010.*
Oda et al., J. Mol. Bio. 351:334-344, 2005.*
Garnier et al., Genbank accession No. P63874, Nov. 2010.*
Kakuda et al., J. Biochem. 116:916-922, 1994.*
Garnant, M.K., et al., Construction and Analysis of Plasmids Containing the *Escherichia coli* serB Gene, Mol Gen Genet 193:72-75, 1984.
Agren, et al., "The C-terminal of CysM from *Mycobacterium tuberculosis* protects the aminoacrylate intermediate and is involved in sulfur donor selectivity," FEBS Letters 583:330-336 (2009).
Burns, et al., "Reconstitution of a New Cysteine Biosynthetic Pathway in *Mycobacterium tuberculosis*," J. Am. Chem. Soc. 127(33):11602-11603 (2005).

(Continued)

*Primary Examiner* — Delia Ramirez
(74) *Attorney, Agent, or Firm* — Cooley LLP

(57) ABSTRACT

The present invention provides methods for the production of cysteine or derivates thereof by culturing a microorganism having reduced activity of endogenous phosphoserine phosphatase and the activity of PhnC, PhnD, and PhnE is reduced, and enhanced activity of phosphoglycerate dehydrogenase and/or phosphoserine aminotransferase. The O-phosphoserine produced by such an organism can then be reacted with a sulfide in the presence of a sulfydrylase or a microorganism expressing a sulfhydrylase to produce cysteine or a derivative thereof. Microorganisms having these reduced and enhanced properties noted above are also provided herein.

17 Claims, 5 Drawing Sheets

(56) References Cited

OTHER PUBLICATIONS

Chang, et al., "Molecular Cloning, DNA Sequencing, and Biochemical Analyses of *Escherichia coli* Glyoxylate Carboligase," The Journal of Biological Chemistry 268(6):3911-3919 (Feb. 25, 1993).

Cusa, et al., "Genetic Analysis of a Chromosomal Region Containing Genes Required for Assimilation of Allantoin Nitrogen and Linked Glyoxylate Metabolism in *Escherichia coli*," Journal of Bacteriology 181(24):7479-7484 (Dec. 1999).

Franke et al., "YfiK from *Escherichia coli* Promotes Export of O-Acetylserine and Cysteine," Journal of Bacteriology 185(4)1161-1166 (Feb. 2003).

Grant et al., "The Contribution of Adjacent Subunits to the Active Sites of D-3-Phosphoglycerate Dehydrogenase," The Journal of Biological Chemistry 274(9):5357-5361 (Feb. 26, 1999).

Grant et al., "Role of an Interdomain Gly-Gly Sequence at the Regulatory—Substrate Domain Interface in the Regulation of *Escherichia coli*. D-3-Phosphoglycerate Dehydrogenase," Biochemistry 39(24):7316-7319 (2000).

Grant et al., "Amino Acid Residue Mutations Uncouple Cooperative Effects in *Escherichia coli* D-3-Phosphoglycerate Dehydrogenase, "The Journal of Biological Chemistry 276(21):17844-17850 (May 25, 2001).

Gui et al., "Autoregulation of iclR, the Gene Encoding the Repressor of the Glyoxylate Bypass Operon," The Journal of Bacteriology 178(1):321-324 (Jan. 1996).

Kim et al., "Identification and Characterization of glxR, a Gene Involved in Regulation of Glyoxylate Bypass in *Corynebacterium glutamicum*," Journal of Bacteriology 186(11):3453-3460 (Jun. 2004).

Kredich and Tomkins, "The Enzymic Synthesis of L-Cysteine in *Escherichia coli* and *Salmonella typhimurium*," The Journal of Biological Chemistry 241(21):4955-4965 (Nov. 10, 1966).

Kumari et al., "Cloning, Characterization, and Functional Expression of acs, the Gene Which Encodes Acetyl Coenzyme A Synthetase in *Escherichia coli*," Journal of Bacteriology 177(10):2878-2886 (May 1995).

Mino and Ishikawa, "A novel O-phospho-L-serine sulfhydrylation reaction catalyzed by O-acetylserine sulfhydrylase from *Aeropyrurn pernix* K1," FEBS Letters 551:133-138 (2003).

Nakamura, "Evidence that Thiosulfate Assimilation by *Salmonella typhimurium* Is Catalyzed by Cysteine Synthase B," Journal of Bacteriology 156(2):656-662 (Nov. 1983).

Peters-Wendisch et al., "3-Phosphoglycerate dehydrogenase from *Corynebacterium glutamicum*: the C-terminal domain is not essential for activity but is required for inhibition by L-serine," Appl Microbiol Biotechnol 60:437-441 (2002).

Ryu et al., "Continuous L-cysteine production using immobilized cell reactors and product extractors," Process Biochemistry 32(3):201-209 (1997).

Sauer et al., "The Soluble and Membrane-bound Transhydrogenases UdhA and PntAB Have Divergent Functions in NADPH Metabolism of *Escherichia coli*," The Journal of Biological Chemistry 279(8):6613-6619 (Feb. 20, 2004).

Wada and Takagi, "Metabolic pathways and biotechnological production of L-cysteine," Appl Microbiol Biotechnol 73:48-54 (2006).

Wanner and Metcalf, "Molecular genetic studies of a 10.9-kb operon in *Escherichia coli* for phosphonate uptake and biodegradation," FEMS Microbiology Letters 100:133-140 (1992).

Westrop et al., "Cysteine Biosynthesis in *Trichomonas vaginalis* Involves Cysteine Synthase Utilizing O-Phosphoserine," The Journal of Biological Chemistry 281(35):25062-25075 (Sep. 1, 2006).

\* cited by examiner

MICROORGANISM PRODUCING O-PHOSPHOSERINE AND METHOD OF PRODUCING L-CYSTEINE OR DERIVATIVES THEREOF FROM O-PHOSPHOSERINE USING THE SAME

CROSS-REFERENCE TO RELATED APPLICATIONS

This application claims the priority benefit of Korean Patent Application Nos. 10-2011-0086081, filed Aug. 26, 2011 and 10-2010-0102664, filed Oct. 20, 2010. The contents of these patent applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_004_02US_ST25.txt. The text file is 79 KB, was created on Oct. 20, 2011, and is being submitted electronically via EFS-Web.

TECHNICAL FIELD

The present invention relates to a method for production of cysteine or its derivatives using O-phosphoserine as an intermediate and recombinant microorganism for use in production of O-phosphoserine.

BACKGROUND ART

L-cysteine is an amino acid that plays an important role in sulfur metabolism of all living organisms. It is used in the biosynthesis of proteins, such as hair keratin, glutathione, biotin, methionine and other sulfur-containing metabolites as well as serving as a precursor of coenzyme A. In addition, the biosynthesis of cysteine is known to be closely associated with the biosynthesis of other amino acids including L-serine, L-glycine, and L-methionine. Industrially, L-cysteine and its derivatives find applications in a variety of fields including the pharmaceutical industry (for treatment of bronchial diseases), the cosmetics industry (in hair shampoo, compositions for permanent waves), and the food industry (antioxidants, flavorant enhancers, dough aids, etc.).

L-cysteine was once obtained industrially by acid hydrolysis of human hairs or animal feathers (Biotechnology of the Amino Acids Production edited by Ko Aida, p 217-223, 1986). However, not only does the production of cysteine from hairs or feathers ensure a yield of as low as 7~8%, but also the use of hydrochloric acid or sulfuric acid produces a lot of waste resulting in environmental pollution. Further, extraction from hairs or feathers may induce the user to have a strong adversion thereto. These problems have caused a push for the development of environmentally friendly production processes of L-cysteine. The main contemporary route involves fermentation utilizing microorganisms.

Representative among the microbial production of L-cysteine is 1) the biological conversion of D,L-ATC using a microorganism (Ryu O H, Ju J Y and Shin C S, Process Biochem., 32:201-209, 1997). This conversion process is, however, difficult to apply industrially due to the low solubility of the precursor D,L-ATC. 2) Another method of L-cysteine production is direct fermentation using *E. coli* (Patent No. EP0885962B; Wada M and Takagi H, Appl. Microbiol. Biochem., 73:48-54, 2006). Excessive accumulation of L-cysteine within microorganisms incurs intracellular toxicity, exhibiting a limitation in the production of L-cysteine at a high concentration. To overcome this drawback, L-cysteine-exporting proteins are employed, but there have been no significant improvements in productivity.

Referring to the biosynthesis pathway of L-cysteine in microorganisms and plants, O-acetyl-serine (OAS) acts as an intermediate precursor providing the carbon backbone of L-cysteine (Kredich N M and Tomkins G M, J. Biol. Chem., 241: 4955-4965, 1966). The enzyme O-acetylserine sulfhydrylase (OASS), using hydrogen sulfide as a sulfur donor, catalyses the conversion of O-acetylserine to cysteine. Alternatively, $SO_4$ may be reduced to thiosulfate for use as a sulfur donor in cysteine production (Nakamura T, Kon Y, Iwahashi H and Eguchi Y, J. Bacteriol., 156: 656-662, 1983). Therefore, cystein may be produced using microorganisms accumulating OAS and OASS using various sulfur donors (U.S. Pat. No. 6,579,705). The cysteine biosynthesis pathway via OAS uses the two enzymes of serine acetyltransferase (CysE), which catalyzes the conversion of OAS from serine, and cysteine synthase (CysK), which catalyzes the conversion of OAS to cysteine. Among them, serine acetyltransferase (CysE) is highly sensitive to feedback inhibition by the final product cysteine (Wada M and Takagi H, Appl. Microbiol. Biochem., 73:48-54, 2006).

DISCLOSURE

Technical Problem

Leading to the present invention, the present inventors found out the existence of O-phosphoserine sulfhydrylase (OPSS) in *Aeropyrum pernix, Mycobacterium tuberculosis,* and *Trichomonas vaginalis* that takes an O-phospho-L-serine (OPS)-specific pathway, rather than the OAS-specific pathway, to synthesize L-cysteine through intensive research (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006) and that the OPSS of *M. tuberculosis*, can use $Na_2S$ as a sulfur donor in converting OPS to cysteine even in the absence of the additional enzymes when five C-terminal amino acid residues are removed therefrom (Argen D, Schnell R and Schneider G, FEBS letters, 583: 330-336, 2009). In the present invention, a microorganism is mutated to accumulate OPS therein, following incubation to convert OPS into cysteine in the presence of the OPSS enzyme. Nowhere has this method been previously described.

Technical Solution

It is an object of the present invention to provide a method for producing cysteine or a derivative thereof.

It is another object of the present invention to provide a recombinant microorganism for the production of O-phosphoserine.

Advantageous Effects

The method of the present invention in which O-phosphoserine is produced at high yield by a recombinant microorganism and is used for conversion into cysteine, as it is, is more friendly to the environment and ensures higher efficiency in the production of cysteine than do chemical synthesis methods. The cysteine and its derivatives produced by the fermentation and bioconversion of the present invention can be widely used in the production of animal and human foods and food additives.

DESCRIPTION OF DRAWINGS

FIG. 4 is a photograph showing the expression level of Msm-T in a pET system and a pCL-Pcj1 system as analyzed by SDS PAGE.

BEST MODE

Figure 1:
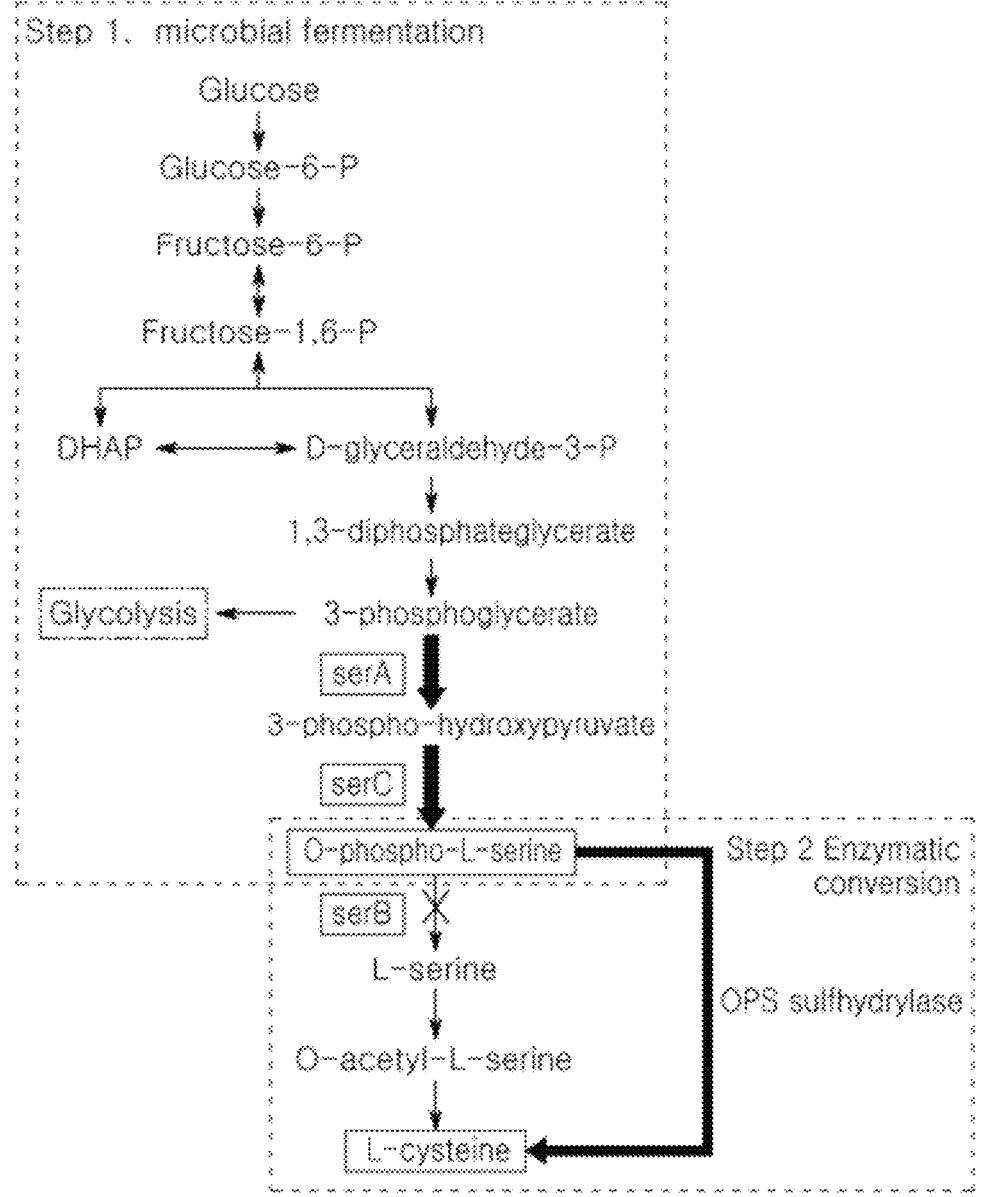
FIG. 1 is a schematic diagram showing the accumulation of O-phosphoserine by microbial fermentation and the enzymatic conversion of the accumulated O-phosphoserine into L-cysteine.

As used herein, the term "cysteine conversion" is intended to refer to the catalytic reaction of O-phosphoserine sulfhydrylase (OPSS) which results in the conversion of the substrate O-phosphoserine (OPS) into the product cysteine, that is, it refers to the catalytic reaction of converting OPS into cyteine.

As used herein, the term "cysteine conversion rate" refers to the percentage of the amount of the product cysteine to the amount of the starting material OPS. Under optimal reaction conditions, 1 mole of OPS is conveted into 1 mole of cysteine. For example, if 100 moles of OPS is converted into 100 moles of cysteine, the cysteine conversion rate is 100%.

In accordance with an aspect thereof, the present invention provides a method for producing cysteine or a derivative thereof, comprising:

1) culturing a recombinant microorganism in which the activity of endogeneous phosphoserine phosphatase (SerB) to produce O-sphosphoserine (OPS); and 2) reacting the OPS of step 1) with a sulfide in the presence of O-phosphoserine sulfhydrylase (OPSS) or a microorganism expressing OPSS, to produce cysteine or a derivative thereof.

The SerB is a protein that has the activity of hydrolyzing OPS into L-serine. Thus, a microorganism which has reduced endogeneous SerB activity is characterized by the accumulation of OPS therein. The SerB is not limited to, may comprise any amino acid sequences, which exhibits SerB activity, and may have preferably the amino acid sequence of SEQ ID NO: 1 or 2. However, as long as it exhibits SerB activity, any amino acid sequence is used, which preferably has a homology of 90% or higher, more preferably 96% or higher, far more preferably 98% or higher, and most preferably 99% or higher with that of SEQ ID NO: 1 or 2. The reduced SerB activity means a decrease in SerB activity, compared to that of a prior-modified strain, and encompasses the disrupting of SerB. Various techniques for reduction of SerB activity are well known in the art. Illustrative examples include the deletion of a chromosomal serB, the introduction of mutation into the chromosomal serB to reduce endogenouse SerB activity, the introduction of mutation into a regulatory region for the serB to reduce endogenouse SerB activity, the substitution of the chromosomal serB with a gene mutated to reduce the endogenouse SerB activity and the introduction of an antisense oligonucleotide complementary to a transcript of the serB to inhibit the translation of the mRNA, but methods for reducing the SerB activity are not limited to these. These techniques may be applied to the reducing the activity of other enzymes in the present invention.

The disruption of endogenous SerB results in the introduction of serine auxotrophy into the recombinant microorganism so that the medium must be supplemented with glycine or serine. Glycine may be provided in the form of purified glycine, a glycine-containing yeast extract, or tryptone. Glycine is contained at a concentration of from 0.1 to 10 g/L, and preferably at a concentration of from 0.5 to 3 g/L. As for serine, it may be provided in the form of purified serine, a serine-containing yeast extract or tryptone. Its concentration in the culture medium ranges from 0.1 to 5 g/L, and preferably from 0.1 to 1 g/L.

In one embodiment of the present invention, when cultured in a glycine- or serine-containing medium, mutant *Corynebacterium glutamicum* or *E. coli* in which the activity of endogenous SerB was disrupted was found to produce a higher amount of OPS, compared to the wild-type (see Tables 2, 3, 6 and 7).

In addition, the recombinant microorganism of the present invention may have enhanced phosphoglycerate dehydrogenase (SerA) or phosphoserine aminotransferase (SerC) activity. The SerA is a protein that has the activity of converting 3-phosphoglycerate to 3-phosphohydroxypyruvate. The SerA may have wild-type amino acids or a mutant amino acid sequence which shows resistance to feedback inhibition by serine, but is not limited to these. Preferably, the SerA may have one selected from the group consisting of amino acid sequences of SEQ ID NOS: 3 to 7. So long as it exhibits wild-type SerA activity or the mutant SerA activity resistant to serine feedback inhibition, any amino acid sequence may be used, although it preferably shares a homology of 90% or higher, more preferably 96% or higher, far more preferably 98% or higher, and most preferably 99% or higher with that of one of SEQ ID NO: 3 to 7. A "mutant SerA resistant to feedback inhibition" means the mutant showing a maintained or enhanced SerA activity irrespective of the feedback inhibition by serine or glycine. The feedback-resistant mutants are well known in the art (Grant G A et al., J. Biol. Chem., 39: 5357-5361, 1999; Grant G A et al., Biochem., 39: 7316-7319, 2000; Grant G A et al., J. Biol. Chem., 276: 17844-17850, 2001; Peters-Wendisch P et al., Appl. Microbiol. Biotechnol., 60: 437-441, 2002; EP0943687B). In one embodiment of the present invention, when a feedback-resistant serA was further introduced thereinto, *Corynebacterium glutamicum* or *E. coli* having a disrupted serB was found to produce a higher amount of OPS, as compared to the wild-type (see Tables 4 and 9).

The SerC is a protein that has the activity of converting 3-phosphohydroxypyruvate to O-phosphoserine. The SerC is not limited to, may comprise the sequences which exhibits SerC activity, and may have preferably the amino acid sequence of SEQ ID NO: 8. However, as long as it exhibits SerC activity, any amino acid sequence may be employed, but it should preferably share a homology of 90% or higher, more preferably 96% or higher, far more preferably 98% or higher, and most preferably 99% or higher with that of SEQ ID NO: 8. Furthermore, a mutation may be introduced into the serC so that the enzyme activity can be increased. In one embodiment of the present invention, when an serC was further introduced thereinto, *Corynebacterium glutamicum* or *E. coli* having a disrupted serB and a feedback-resistant serA was found to produce a higher amount of OPS, compared to the wild-type (see Table 9).

Further, the capacity of the recombinant microorganism of the present invention to perform the intracellular uptake of or the degradation of O-phosphoserine may be decreased. In detail, the recombinant microorganism may be modified to reduce the activity of PhnC/PhnD/PhnE alkylphosphonate ABC transporter (PhnCDE operon, that is, ATP-binding component of phosphonate transport (PhnC; EG 10713)-periplasmic binding protein component of Pn transporter (PhnD; EG 10714)-integral membrane component of the alkylphosphonate ABC transporter (PhnE; EG 11283)), alkaline phosphatase (PhoA) or acid phosphatase (AphA).

In one embodiment of the present invention, the further deletion of the phnCDE operon from the recombinant mutant was observed to lead to an increase in OPS production (Table 10). In the recombinant microorganism which was further disrupted of PhoA or AphA activity, OPS degradation started to decrease at the time when the concentration of phosphoric acid in the culture medium is decreased (Table 12). Moreover, the introduction of a feedback-resistant serA or a serC raised OPS production (Tables 14 to 16).

Also, the recombinant microorganism of the present invention may be further characterized by the enhancement of pyrimidine nucleotide transhydrogenase (PntAB; EC 1.6.1.1) activity. As described previously (Sauer U P et al., J Biol. Chem. 20; 279(8):6613-9. Epub 2003), PntAB participates in NADPH metabolism to regulate intracelluar redox balance. In one embodiment of the present invention, the recombinant microorganism in which PntAB activity was further enhance by overexpression of pntAB was found to increase OPS production (Table 17).

Moreover, the recombinant microorganism of the present invention may be characterized by the enhancement of O-acetylserine/cysteine efflux permease (YfiK), homoserine/homoserine lactone efflux protein (RhtB; EG 11469) or threonine/homoserine lactone efflux protein (RhtC; EG11468). The YfiK is known as an exporter for exporting cysteine and OAS extracellularly (Franke I et al., J. Bacteriology, 185: 1161-1166, 2003) and RhtB is reported to act as an extracellular exporter of homoserine/homoserine lactone, a threonine precursor. Further, the RhtC is known as an exporter of threonine and homoserine. The enhancement of the activity of YfiK, RhtC and RhtB showed an increase in the growth and OPS production of the OPS accumulation strain (Table 18).

The enhancement of the enzyme activity may be achieved using various well-known methods, including, but not being limited to, increasing the copy number of a gene encoding an enzyme of interest, introducing a mutation into a regulatory region for the gene to enhance the enzyme activity, substituting the chromosomal gene with a gene mutated to enhance the enzyme activity, and introducing a mutation into the chromosomal gene to enhance the enzyme activity.

In addition, the recombinant microorganism of the present invention is further characterized by the reduced activity of phosphoglycerate mutase. The phosphoglycerate mutase exists as three isozymes: GpmI, GpmA and GpmB and is responsible for the conversion of 3-phosphoglycerate to 2-phosphoglycerate in the glycolysis process. For the use of 3-phosphoglycerate as a substrate, these enzymes are in competition with SerA that catalyzes the synthesis of 3-phosphohydroxypyruvate. Therefore, the decreasing activity of each of the enzymes was observed to cause an abundance of 3-phosphoglycerate, a precursor of OPS, resulting in the production of an increased level of OPS (Table 19).

In the recombinant microorganism of the present invention, L-serine dehydratase I (SdaA; EC 4.3.1.17) or 2-amino-3-ketobutyrate coenzyme A ligase (Kbl) may be also reduced. Thus, the recombinant microorganism is characterized by the OPS production maintained or increased even when it is cultured in a medium containing a low concentration of glycine or serine (Table 20).

Further, the recombinant microorganism of the present invention may be further characterized by the reduced activity of IclR. IclR is a transcription factor that functions to repress the expression of aceBAK, a glyoxylate bypass operon (L Gui et al., J. Bacteriol., Vol 178, No. 1, 321-324, 1996). When it was deleted, the production of OPS was observed to increase (Table 21).

Also, the recombinant microorganism of the present invention may be further characterized by the enhancement of an enzyme activity selected from the group consisting of i) acetyl-CoA synthetase (Acs), ii) acetic acid kinase (AckA)-phosphotransacetylase (Pta), iii) malate synthase G (GlcB), iv) malate dehydrogenase (MaeB), v) glutamate dehydrogenase (GdhA), vi) glyoxylate carboligase (Glc), vii) tartronate semialdehyde reductase 2 (GlxR), viii) glycerate kinase II (GlxK), and a combination thereof.

In a concrete embodiment of the present invention, when i) Acs (EC No. 6.2.1.1; J. Bacteriol. 1995 May; 177(10): 2878-86) or pyruvate oxidase monomer (PoxB; EC 1.2.2.2) or ii) AckA and Pta (EC 2,3,1,8), all of which aim to effectively reuse accumulated acetate with the concomitant consumption of produced NADH, were further enhanced, the recombinant microorganism of the present invention was found to increase production of OPS (Table 22). Functioning to catalyze the synthesis of malate from glyoxylate and the conversion of malate into pyruvate, iii) GlcB (EC No. 2.3.3.9) and iv) MaeB (EC 1.1.137) can weaken the TCA cycle and thus be used to increase the glucose consumption and the production of O-phosphoserine (Table 23). According to one embodiment of the present invention, the enhancement of v) GdhA; (EC 1.4.1.2), which catalyzes the synthesis of glutamate, a substrate of SerC, from 2-oxoglutarate and NADPH, bestowed a much higher potential for producing OPS on the microorganism (Table 17). All of vi) Glc(EC 4.1.1.47), vii) GlxR(EC 1.1.1.60) and viii) GlxK(EC 2.7.1.31) are known to convert glyoxylate into 3-phosphoglycerate, that is, to increase the level of the substrate of phosphoglycerate dehydrogenase (Kim H J et al., J. Bacteriol., 186(11), 3453-3460, 2004; Eva Cusa et al., J. Bacteriol., 181(24), 7479-7484, 1999; Chang Y Y et al., J. Biol. Chem. 268(6): 3911-3919, 1993). The recombinant microorganism of the present invention, when further enhanced in the activity of Glc, GlxR and GlxK, was improved in sugar consumption and growth (Table 24).

The recombinant microorganism of the present invention refers to any microorganism in which there is the reduction of SerB activity, thus producing OPS at an elevated level. If this condition is satisfied, any microorganism, whether prokaryotic or eukaryotic, falls within the scope of the present invention. Representative among them are enterobacteria or coryneform bacteria. Examples of the microorganisms useful in the present invention include *Escherichia* sp., *Erwinia* sp., *Serratia* sp., *Providencia* sp., *Corynebacterium* sp., and *Brevibacterium* sp. Preferable are *Escherichia* sp. and

*Corynebacterium* sp, with more preference given for *Escherichia* sp. and with the highest preference being for *E. coli*.

In an embodiment, the recombinant strain capable of producing OPS was named *E. coli* CA07-0012, and deposited with the Korean Culture Center of Microorganisms, located at 361-221, Hongje 1, Seodaemun, Seoul, Korea, on Oct. 12, 2011 under accession number KCCM11212P.

In addition, in an embodiment, the recombinant strain capable of producing OPS was named *E. coli* CA07-0022/ pCL-prmf-serA*(G336V)-serC, and deposited with the Korean Culture Center of Microorganisms, located at 361-221, Hongje 1, Seodaemun, Seoul, Korea, on Sep. 28, 2010 under accession number KCCM11103P. Herein, the term "CA07-0022/pCL-prmf-serA*(G336V)-serC" is used interchangeably with CA07-0022 serA*(G336V)/pCL-prmf-serA*(G336V)-serC.

After the strain was cultured for 80 hours in a 1 L fermenter, O-phosphoserine was produced at a concentration of 19.5 g/L (Example 35).

As used herein, the term "culturing" is intended to mean growing microorganisms under artificially controlled conditions. A culturing procedure may be conducted using a suitable medium and culturing conditions well known in the art. Those skilled in the art can readily control the culturing procedure to correspond to the strains employed. For example, it may be performed in a batch type, in a continuous type, or in a fed-batch type, but is not limited thereto.

In addition, the culture medium contains a carbon source. Examples of the carbon source include saccharides and carbohydrates such as glucose, sucrose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be present solely or in combination in the culture medium. As a nitrogen source, an organic material such as peptone, yeast extract, meat juice, malt extract, corn steep liquor, soybean, and wheat protein, or an inorganic nitrogen compound such as urea, ammonium sulfate, ammonium chloride, ammonium phosphate, ammonium carbonate and ammonium nitrate may be contained in the culture medium. These nitrogen sources may be used solely or in combination. The medium may contain potassium dihydrogen phosphate, potassium phosphate, or corresponding sodium salts as a phosphorous source. The medium may contain metallic salts such as magnesium sulfate or iron sulfate. The culture medium may also contain amino acids, vitamins and suitable precursors. The nutrients may be added in a batch manner or a continuos manner to the medium.

A compound such as ammonium hydroxide, potassium hydroxide, ammonia, phosphoric acid and sulfuric acid may be added in a suitable manner to the culture medium during culturing to adjust the pH of the culture. In addition, during culturing, an anti-foaming agent such as fatty acid polyglycol ester is used to suppress the formation of foam. Further, in order to maintain the culture medium in an aerobic condition, oxygen or oxygen-containing gas can be injected into the culture medium. For an anaerobic or microaerobic condition, nitrogen, hydrogen, or carbon dioxide is provided without aeration. The culture medium may be typically maintained at a temperature of from 27° C. to 37° C. and preferably at a temperature of from 30° C. to 35° C. As for the culture period, it may be maintained until the product of interest is obtained in a desired amount, and preferably it ranges from 10 to 100 hours.

For further collection and recovery of the OPS produced during the culturing step from the culture medium, a suitable method well known in the art may be selected depending on the type of culture, be it a batch, continuous or fed-batch culture.

In the method of the present invention, step 2) addresses the reaction of the OPS of step 1) with a sulfide in the presence of O-phosphoserine sulfhydrylase (OPSS) or a microorganism expressing OPSS, to induce the conversion of O-phosphoserine into cysteine or its derivatives.

The sulfide may be provided in a liquid or gas form as well as in a solid form typically used in the art, because of the difference in pH, pressure and/or solubility. So long as it may be converted to a thiol group (SH), any sulfur compound such as sulfide ($S^{2-}$) or thiosulfate ($S_2O_3^{2-}$) may be used in the present invention. Preferably, $Na_2S$, NaSH, $H_2S$, $(NH_4)_2S$, NaSH and $Na_2S_2O_3$, all of which can provide a thiol group for OPS, may be used. In the reaction, one thiol group is supplied to one OPS molecule to afford one molecule of cysteine or a derivative thereof. In this enzymatic conversion, a sulfide may be preferably added at a molar concentration 0.1 to 3 times and more preferably 1 to 2 times as high as that of OPS used. In light of the economy, a thiol group-providing sulfide and OPS are most preferably used at a molar ratio of 1:1. In one embodiment of the present invention, $Na_2S$ was used as the source of sulfur. $Na_2S$ was added at a molar concentration 1 to 3 times as high as that of OPS used in the conversion reaction. Preferably, it is fed at a molar concentration twice as high as that of OPS to effectively convert OPS into cysteine (Table 34).

As used herein, the term "O-phosphoserine sulfhydrylase (OPSS)" refers to an enzyme that catalyzes the transfer of a thiol group (SH) to OPS(O-phosphoserine) to convert OPS into cysteine. The enzyme was first found in *Aeropyrum pernix, Mycobacterium tuberculosis,* and *Trichomonas vaginalis* (Mino K and Ishikawa K, FEBS letters, 551: 133-138, 2003; Burns K E et al., J. Am. Chem. Soc., 127: 11602-11603, 2005). The above mentioned enzymes have the amino acid sequences of SEQ ID No: 9 and 12.

As used herein, the term "mutant" refers to a culture or an individual that shows an inheritable or non-heritable alteration in phenotype. When used in conjunction with OPSS, the term "mutant" is intended to mean an OPSS enzyme which is genetically altered such that its activity can be effectively enhanced, compared to the wild-type.

In the present invention, the OPSS mutant can be constructed by deleting, substituting or adding a part of a nucleotide sequence encoding OPSS. According to one embodiment of the present invention, an OPSS enzyme with enhanced activity was prepared by deleting five C-terminal amino acid residues of the OPSS enzyme of *Mycobacterium smegmatis*. The mutant enzymes have the amino acid sequences of SEQ ID NO: 10 and 11.

The OPSS mutant can be obtained in *E. coli*, widely used for enzyme expression, using gene synthesis techniques based on codon optimization by which enzymes of interest can be obtained in high yield. Alternatively, screening methods of useful enzyme resources based on the bioinformatics of massive amounts of genetic information about microorganisms may be used to obtain the OPSS mutant. In one embodiment of the present invention, OPSS enzymes that utilize OPS as a substrate to synthesize cysteine were selected from various microbes by screening the homology of amino acid sequences. In this regard, cell pellets obtained using a medium and culture conditions that were suitable in the art were lyzed, followed by the purification of the supernatant containing the enzyme to afford the OPSS enzyme (Table 26).

In addition, a high-yield expression system was developed for obtaining the OPSS enzyme economically. A pET vector employing a T7 promoter is well known in the art. However, the present inventors developed an enzyme expression system, named the CJ1 system (Korean Patent 10-0620092 B1), instead of employing the typical system. In one embodiment of the present invention, the expression levels of OPSS between a pET system comprising a T7 promoter and the CJ1 system comprising a CJ1 promoter were compared given the same conditions. As a result, the CJ1 system showed a higher expression level of OPSS than the pET system. In addition, the overexpression of OPSS required a low temperature (18° C.) and a long period of time in the pET system, but a high temperature (37° C.) and a short period of time in the pCL-pCJ1 system. Preferably, the pCL-pCJ1 system is used to obtain OPSS (Example 46).

The enhancement of the enzyme activity may be achieved using various well-known methods. For example, it can be performed by increasing the number of copies of a gene encoding OPSS, using a strong promoter, or introducing a genetic mutation.

Optimization of the enzymatic conversion of OPSS may be achieved using various methods known in the art. For example, the optimization may be based on a full understanding of the characteristics of OPSS, such as the optimal temperature and pH, inhibition against substrates, substrate concentration, heat stability, etc. In addition, the optimization may be determined by optimal conditions for the enzymatic conversion, such as the optimal OPSS concentration, the optimal balances of the substrates used in terms of concentrations, a preference for sulfur compounds providing SH for the enzymatic conversion, a preference for certain buffers, the influence of ions generated, and cofactors and their optimal concentrations.

In one embodiment of the present invention, the OPSS enzyme obtained using the above-mentioned method was characterized and on the basis of the determined characteristics, an economically beneficial enzymatic conversion process that has a high conversion rate of cysteine from OPS, with the guarantee of enzyme stability, was developed. In the enzymatic conversion process, the reaction temperature can be set from 37° C. to 80° C. In detail, Ape-OPSS (SEQ ID NO: 12), belonging to Archea, exhibits increased enzymatic activity at 60° C. compared to 37° C., and the enzyme itself is highly stable to heat, with optimal reactivity at 60° C. On the other hand, Msm-T (SEQ ID NO: 10) exhibits optimal activity at 37° C. and is relieved the activity to heat treatment at 60° C. The OPSS enzyme was observed to have enzymatic activity over a pH range of 6.0 to 10.0. Ape-OPSS showed optimal activity at pH 7.4. With the appearance of optimal activity at a pH of from 8.0 to 9.0, Msm-T showed stability over a wider pH range, compared to Ape-OPSS (Tables 28 and 31, and FIGS. 2 and 3).

As a cofactor, 0.001-2 mM PLP (pyridoxal-5'-phosphate) or 0.001-100 mM DTT may be used in the enzymatic conversion. In one embodiment of the present invention, the cysteine conversion rate was 2.3-fold increased in the presence of 25 mM DTT or 0.2 mM PLP. As such, treatment with DTT or PLP brought about an improvement in the cysteine conversion rate of step 2). The addition of the cofactor was set to a reasonable level in consideration of the increased production cost and the increased conversion rate (Table 30).

Figure 5:
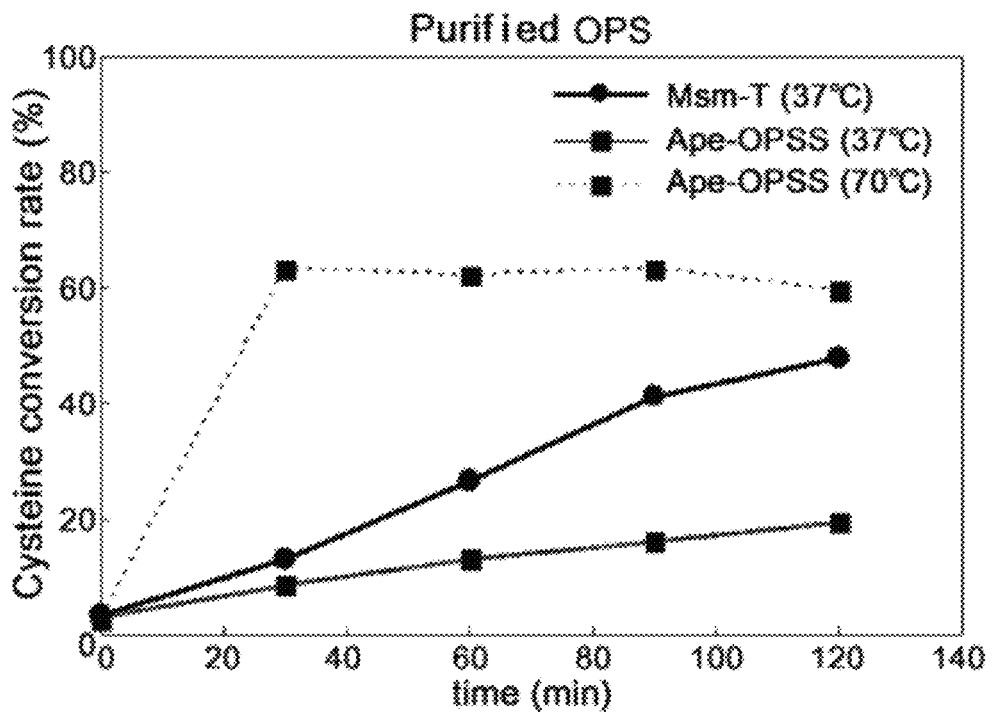
FIG. 5 is a graph showing the enzymatic activity of OPS sulfhydrylase to convert purified OPS fermentation broth into cysteine.
Figure 6:
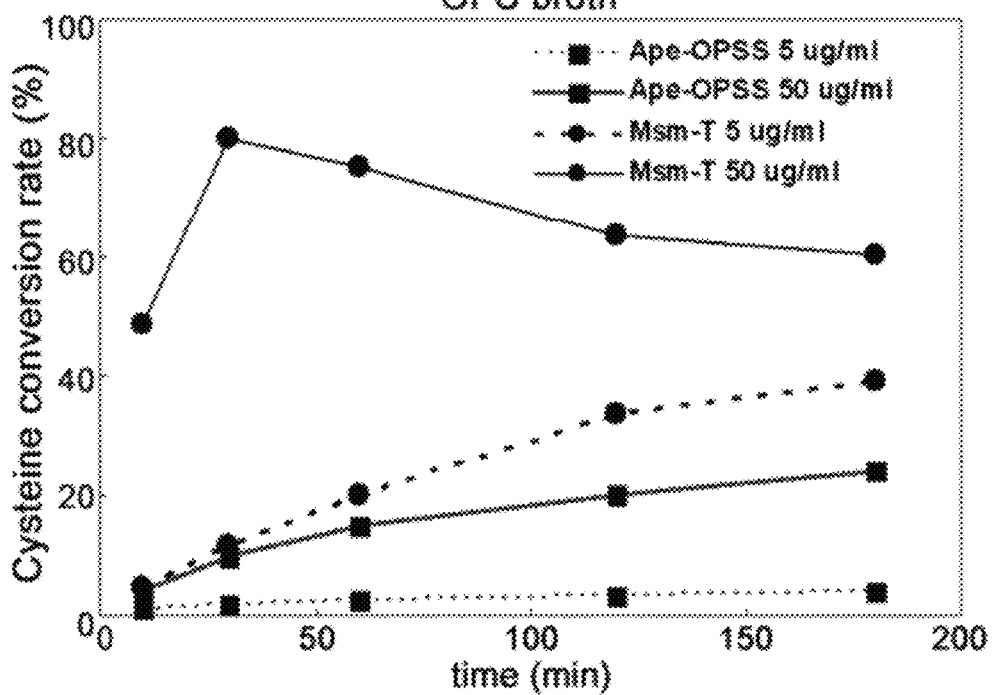
FIG. 6 is a graph showing the enzymatic activity of OPS sulfhydrylase to convert OPS fermentation broth into cysteine.

The reaction conditions for OPSS may vary depending on the kinds and concentration of the OPS used. In one embodiment of the present invention, pure OPS (commercially available), OPS purified from the culture prepared in step 1), and the OPS-containing culture of step 1) were used under various conditions to provide the optimal conversion rates. As a result, the cysteine conversion rate varied depending on the kind and concentration of OPSS and the reaction temperature and the kind and concentration of OPS (FIGS. 5 and 6, and Table 35).

The method of the present invention may further comprise isolating and purifying the cysteine produced in step 2). After the enzymatic conversion, cysteine can be isolated and purified from the culture medium using a method well known in the art.

Those skilled in the art may chemically synthesize cysteine derivatives from cysteine using a well known method. Cysteine may be readily reacted with an acetylation agent to give NAC (N-acetylcysteine) and with haloacetic acid under basic conditions to give SCMC (S-carboxymethylcysteine). These cysteine derivatives are used as materials in medicines that treat coughs, bronchitis, bronchial asthma, and sore throat.

In the present invention, the OPS broth obtained through microbial fermentation is used as a substrate for synthesizing cysteine. The OPS broth obtained by microbial fermentation has economical advantages over commercially available pure OPS in that the OPS broth can be used without having to be additionally purified and the cofactor PLP necessary for the conversion can be obtained from the fermented culture.

In one embodiment of the present invention, a conversion process was developed which ensures a cysteine conversion rate of as high as 80% when 50 µg/ml Msm-T was used under reaction conditions of a 50 mM OPS broth or a 60 mM purified OPS broth, 100 mM $Na_2S$ or 120 mM $Na_2S$, and 0.2 mM PLP. It should be appreciated to those skilled in the art that the enzymatic conversion using highly active enzymes can easily be optimized and scaled up.

In accordance with another aspect thereof, the present invention provides a recombinant microorganism which is reduced the activity of SerB for the production of OPS. In one embodiment, the recombinant microorganism shows an enhancement of serine feedback-resistant serA or serC or deletion of at least one selected from among PhnC/PhnD/PhnE alkylphosphonate ABC transporter (phnCDE operon), alkaline phosphatase (phoA) and acid phosphatase (aphA). Preferably, the recombinant microorganisms for the production of OPS are the microorganism deposited under accession No. KCCM11103P or KCCM11212P. More preferably, the recombinant microorganism for the production of OPS is the microorganism deposited under accession No. KCCM11103P.

MODE FOR INVENTION

A better understanding of the present invention may be obtained through the following examples which are set forth to illustrate, but are not to be construed to limit the present invention.

Preparation of O-Phosphoserine Producing *Corynebacterium* and Production of O-Phosphoserine Using the Same Example 1: Preparation of Phosphoserine Phosphatase (serB) Deficient *Corynebacterium* Strain

*Corynebacterium glutamicum* 13032 was modified by deleting the serB gene (SEQ ID NO: 13, EC 3.1.3.3)

encoding phosphoserine phosphatase, which catalyses the synthesis of L-serine from O-phosphoserine, therefrom. To this end, a fragment for inactivation of serB was constructed. In this regard, primers were designed for the preparation of the recombinant strain 13032-ΔserB of the present invention. First, the serB sequence of *Corynebacterium glutamicum* 13032 was obtained with reference to the data of the NIH GenBank, and primers SEQ ID NOS: 22 to 27 were synthesized on the basis of the serB sequence. For the site-specific gene disruption, a pDC vector which cannot replicate in *Corynebacterium glutamicum* was employed. A pDC-ΔserB plasmid in which the open reading frame of serB was internally disrupted was constructed and adopted for the preparation of a site-specific serB gene deletion in *Corynebacterium glutamicum* mutant strain. The internal gene disruption of the pDC-ΔserB was generated by crossover PCR using primer pairs of SEQ ID NOS: 22 and 23 and SEQ ID NOS: 24 and 25, with the genomic DNA of *Corynebacterium glutamicum* ATCC13032 serving as a template, and introducing the PCR product into a pDC vector. The resulting recombinant plasmid was transformed into wild-type *Corynebacterium glutamicum* by electroporation (van der Rest et al. 1999). The plasmid was introduced into the chromosome by primary recombination (crossing over), followed by secondary recombination (crossing over) to excise the original serB from the chromosome.

After completion of the secondary recombination, the *Corynebacterium glutamicum* transformants containing the deletion mutation of serB was analyzed by diagnostic PCR using a pair of gene-specific primers SEQ ID NOS: 26 and 27. The recombinant strain was named CB01-0047.

Example 2: Assay for O-Phosphoserine Productivity in the Phosphoserine Phosphatase Deficient *Corynebacterium* Strain The mutant strain CB01-0047, resulting from the deletion of serB from *Corynebacterium glutamicum* 13032, which was anticipated to accumulate O-phosphoserine, was spread over BHIS plates and incubated overnight in a 30° C. incubator. Afterwards, the colonies appearing on the BHIS plates were inoculated in 25 mL of a titer medium shown in Table 1 using a platinum loop and then incubated at 30° C. for 48 hours with shaking at 200 rpm. The results are summarized in Table 2, below.

TABLE 1

| Composition | Amount (per liter) |
|---|---|
| Glucose | 100 g |
| $KH_2PO_4$ | 1.1 g |
| $(NH_4)_2SO_4$ | 45 g |
| $MgSO_4 \cdot 7H_2O$ | 1.2 g |
| HSM | 20 g |
| Trace elements | 20 ml |
| Calcium carbonate | 30 g |
| pH | 7.2 |
| Trace elements | |
| Biotin | 0.09 g |
| Thiamine | 0.45 g |
| Ca-Panthenate | 0.45 g |
| NCA | 3 g |
| $FeSO_4 \cdot 7H_2O$ | 9 g |
| $MnSO_4 \cdot 4H_2O$ | 9 g |
| $ZnSO_4 \cdot 7H_2O$ | 0.045 g |
| $CuSO_4 \cdot 5H_2O$ | 0.045 g |

TABLE 2

| Strain | OD 562 nm | Sugar consumed (g/L) | O-phosphoserine (g/L) |
|---|---|---|---|
| *C. glutamicum* 13032 | 25 | 100 | 0.02 |
| CB01-0047 | 6.5 | 23 | 0.07 |

The CB01-0047 strain was observed to grow very slowly in the titer medium. This growth retardation was not improved even upon the addition of an L-glycine supplement. However, the growth was increased in the presence of L-serine, but a slight increase in the production of 0-phosphoserine compared to the wild-type was observed. The results are summarized in Table 3, below.

TABLE 3

| Strain | A.A. (amino acids) added | OD 562 nm | Sugar consumed (g/L) | O-phosphoserine (g/L) |
|---|---|---|---|---|
| CB01-0047 | — | 6.3 | 21 | 0.09 |
| | L-Glycine | 6.9 | 22 | 0.09 |
| | L-Serine | 24.5 | 100 | 0.05 |

Example 3: Construction of Mutated Phosphoglycerate Dehydrogenase (SerA*) Gene Derived from *Corynebacterium*

The *Corynebacterium glutamicum*-derived genes serA* (E235K) (SEQ ID NO: 14) and serA*(197Δ) (SEQ ID NO: 15) were constructed, which encode respective mutants of 3-phosphoglycerate dehydrogenase, an enzyme catalyzing the synthesis of 3-phosphohydroxypyruvate from 3-phosphoglycerate. The mutants were reported to be feedback resistant (FBR) to serine (Peters-Wendisch P et al., Appl. Microbiol. Biotechnol., 60: 437-441, 2002; EP0943687B). serA*(E235K) was obtained by sewing PCR on the genomic DNA of ATCC13032 using primers of SEQ ID NOS: 28 to 31 while serA*(197Δ) was constructed by PCR using pairs of primers of SEQ ID NOS: 28 to 32. The PCR products thus obtained were inserted into respective T vectors to construct recombinant vectors called Tblunt-serA*(E235K) and Tblunt-serA*(197Δ). Subsequently, the two vectors were treated with restriction enzymes EcoRV and XbaI to give two DNA fragments serA*(E235K) and serA*(197Δ). These fragments were inserted to respective pECCG117-Pcj7-GFP-terminator vectors which had been digested with the same restriction enzymes. As a result, two recombinant vectors pECCG117-Pcj7-serA*(E235K), and pECCG117-Pcj7-serA*(197Δ) were obtained.

Example 4: Preparation of serA* Overexpressing *Corynebacterium* Strain and Assay for O-Phosphoserine Productivity The two *Corynebacterium*-derived FBR-serA* plasmids constructed in Example 3 were introduced into *Corynebacterium glutamicum* CB01-0047. To evaluate O-phosphoserine productivity, the transformants were spread over BHIS plates and incubated overnight at 30° C. Afterwards, the colonies appearing on the BHIS plates were inoculated in 25 mL of a titer medium shown in Table 1 additionally contained 2 g/L L-serine using a platinum loop and then incubated at 30° C. for 48 hours with shaking at 200 rpm. The results are summarized in Table 4, below.

TABLE 4

| Strain | OD 562 nm | Sugar consumed (g/L) | O-phosphoserine (g/L) |
|---|---|---|---|
| CB01-0047/pECCG117 | 24.5 | 100 | 0.03 |
| CB01-0047/pECCG117-Pcj7-serA*(E235K) | 25.3 | 100 | 0.3 |
| CB01-0047/pECCG117-Pcj7-serA*(197Δ) | 24.3 | 100 | 0.28 |

In the *Corynebacterium glutamicum* strains transformed with the *corynebacterium*-derived FBR-serA*, as shown in Table 4, The accumulations of O-phosphoserine at a concentration of from 0.1 to 0.3 g/L were observed.

Preparation of O-Phosphoserine Producing *E. coli* and Production of O-Phosphoserine Using the Same Example 5: Preparation of *E. Coli* Strain Having the Reduced Activity of Phosphoserine Phosphatase (SerB)

*E. coli* was modified by deleting the serB gene (SEQ ID NO: 16) encoding phosphoserine phosphatase, which catalyses the synthesis of L-serine from O-phosphoserine, therefrom. The deletion mutant *E. coli* K12 was prepared using the one-step inactivation method (Datsenko K A and Wanner B L, Proc. Natl. Acad. Sci., 97: 6640-6645, 2000) to delete an antibiotic-resistant maker gene. To prepare the serB deletion strain, first, PCR was performed on a pKD3 plasmid (Datsenko K A and Wanner B L, Proc. Natl. Acad. Sci., 97: 6640-6645, 2000; GenBank No. AY048742) using a pair of primers of SEQ ID NOS: 33 and 34. The PCR product was introduced into competent cells of pKD46 containing *E. coli* K12 (Datsenko K A and Wanner B L, Proc. Natl. Acad. Sci., 97: 6640-6645, 2000; GenBank No. AY048746) by electroporation. Thereafter, strains that showed resistance to chloramphenicol were subjected to PCR to confirm the deletion of serB, and then transformed with pCP20 (Datsenko K A and Wanner B L, Proc. Natl. Acad. Sci., 97: 6640-6645, 2000) to remove the antibiotic-resistant marker. The resulting mutant strain was named CA07-0012.

In addition, the initiation codon of serB was modified to lower phosphoserine phosphatase activity as follows. The wild-type serB gene with ATG as an initiation codon was obtained by PCR with the genomic DNA of *E. coli* W3110 serving as a template. A mutant serB with CTG as an initiation codon was constructed by sewing PCR. A pair of primes of SEQ ID NOS: 35 and 36 was used in the PCR for amplifying the wild-type serB while pairs of primers of SEQ ID NOS: 37 to 38 were employed for PCR amplification of the mutant serB. The PCR products was treated with HindIII and cloned into pccBAC1 (Epicentre) at the HindIII restriction site to construct pccBAC1-Pself-ATG-serB, and pccBAC1-Pself-CTG-serB respectively. The wild-type and the mutant serB vector was introduced into CA07-0012 to compare the phosphoserine phosphatase activity.

Example 6: Assay of Strain Having the Reduced Activity of SerB for O-Phosphoserine Productivity The phosphoserine phosphatase deficient mutant strain CA07-0012 that was anticipated to accumulate O-phosphoserine, was spread over LB plates and incubated overnight in a 33° C. incubator. Afterwards, the colonies appearing on the LB plates were inoculated in 25 mL of a titer medium shown in Table 5 using a platinum loop and then incubated at 33° C. for 48 hours with shaking at 200 rpm. The results are summarized in Table 6, below.

TABLE 5

| Composition | Amount (per liter) |
|---|---|
| Glucose | 40 g |
| $KH_2PO_4$ | 2 g |
| $(NH_4)_2SO_4$ | 17 g |
| $MgSO_4 \cdot 7H_2O$ | 1 g |
| $FeSO_4 \cdot 7H_2O$ | 10 mg |
| $MnSO_4 \cdot 4H_2O$ | 10 mg |
| $ZnSO_4 \cdot 7H_2O$ | 10 mg |
| Yeast extract | 2 g |
| Calcium carbonate | 30 g |
| pH | 6.8 |

TABLE 6

| Strain | OD 562 nm | Sugar consumed (g/L) | O-phosphoserine (g/L) |
|---|---|---|---|
| *E. coli* W3110 | 16 | 40 | 0.03 |
| CA07-0012 | 9.8 | 16 | 0.5 |
| CA07-0012/pccBAC1-Pself-ATG-serB | 20 | 40 | 0 |
| CA07-0012/pccBAC-Pself-CTG-serB | 15 | 40 | 0.7 |

To enhance the growth and O-phosphoserine productivity thereof, CA07-0012 was cultured for 48 hours in the titer medium of Table 5 additionally contained 1 g/L L-glycine. The results are summarized in Table 7, below.

TABLE 7

| Strain | OD 562 nm | Sugar consumed (g/L) | O-phosphoserine (g/L) |
|---|---|---|---|
| *E.coli* W3110 | 16 | 40 | 0.03 |
| CA07-0012 | 18 | 40 | 1.5 |

As shown in Table 7, the addition of L-glycine to the culture medium allowed the strain to increase the growth rate and the O-phosphoserine productivity.

Example 7: Construction of the Vector Harvoring the Mutated Phosphoglycerate Dehydrogenase (Sera*) Gene Derived from *E. coli*

The *E. coli*-derived genes serA*(G336V) (SEQ ID NO: 18), serA*(G336V, G337V) (SEQ ID NO: 19), and serA* (G336V, R338G) (SEQ ID NO: 20) encoding respective mutants of 3-phosphoglycerate dehydrogenase, an enzyme catalyzing the synthesis of 3-phosphohydroxypyruvate from 3-phosphoglycerate were constructed. The mutants were reported to be feedback resistant (FBR) to serine (Grant G A, Xu X L and Hu Z, Biochem., 39: 7316-7319, 2000; Grant G A, Hu Z and Xu X L, J. Biol. Chem., 276: 17844-17850, 2001). The introduction of the mutant genes into the chromosome of *E. coli* was carried out using the sewing PCR method. The DNA fragments containing mutations were prepared using following primers.

Primers of SEQ ID NOS: 39 and 41 were used commonly in SerA* gene. To introduce mutations into the serA gene, PCR was performed with a pair of primers of SEQ ID NOS: 42 and 43 for serA*(G336V), with a pair of primers of SEQ ID NOS: 44 and 45 for serA*(G336V, G337V), and with a pair of primers of SEQ ID NOS: 46 and 47 for serA* (G336V, R338G). The primers were synthesized on the basis of information about the K12 W3110 gene (GenBank accession number AP 003471) and its neighboring nucleotide sequences, registered in the NIH GenBank.

Example 8: Cloning of *E. Coli*-Derived SerA Gene, SerA* Gene, and 3-Phosphoserine Aminotransferase (serC) Gene serA (SEQ ID NO: 17, EC 1.1.1.95), serC (SEQ ID NO: 21, EC 2.6.1.52), serA*(G336V), serA*(G336V, G337V) and serA*(G336V, R338G) were cloned as follows. serA and serC were obtained by performing PCR on the genomic DNA of *E. coli* W3110 while serA*(G336V), serA*(G336V, G337V), and serA*(G336V, R338G) were constructed by PCR with the DNA fragments of Example 7 serving as templates. PCR primers were SEQ ID NOS: 48 and 49 for serA and SEQ ID NOS: 50 and 51 for serC. After treatment with EcoRV and HindIII, the PCR products were cloned into the recombinant vector pCL-Prmf, constructed by inserting the *E. coli* rmf promoter into the pCL1920 vector (GenBank No AB236930) to produce respective recombinant vectors named pCL-Prmf-serA, pCL-Prmf-serC, pCL-Prmf-serA* (G336V), pCL-Prmf-serA*(G336V, G337V), and pCL-Prmf-serA*(G336V, R338V) respectively.

In addition, plasmids in which serA, one of the three serA mutants, and/or serC form an operon, that is, pCL-Prmf-serA-(RBS)serC, pCL-Prmf-serA*(G336V)-(RBS)serC, pCL-Prmf-serA*(G336V, G337V)-(RBS)serC, and pCL-Prmf-serA*(G336V, R338V)-(RBS)serC were constructed. In this regard, an (RBS)serC fragment was obtained using primers of SEQ ID NOS: 51 and 52 and cloned at a HindIII site into pCL-Prmf-serA, pCL-Prmf-serA*(G336V), pCL-Prmf-serA*(G336V, G337V), and pCL-Prmf-serA*(G336V, R338V).

Example 9: Preparation of *E. coli*-Derived serA, serA* and serC Enhanced Strains and Assay for O-Phosphoserine Productivity The eight plasmids constructed in Example 8 were transformed into CA07-0012 and the resulting recombinant strains were assayed for the productivity of O-phosphoserine. Each strain was spread over LB plates and incubated overnight at 33° C. Afterwards, colonies appearing on the LB plates were inoculated into 25 mL of titer media of Table 8 and cultured at 33° C. for 48 hours with shaking at 200 rpm. The results are summarized in Table 9, below.

TABLE 8

| Composition | Amount (per liter) |
|---|---|
| Glucose | 40 g |
| KH$_2$PO$_4$ | 4 g |
| (NH$_4$)$_2$SO$_4$ | 17 g |
| MgSO$_4$•7H$_2$O | 1 g |
| FeSO$_4$•7H$_2$O | 10 mg |
| MnSO$_4$•4H$_2$O | 10 mg |
| ZnSO$_4$•7H$_2$O | 10 mg |
| L-Glycine | 2.5 g |
| Tryptone | 2 g |

TABLE 8-continued

| Composition | Amount (per liter) |
|---|---|
| Yeast extract | 2 g |
| Calcium carbonate | 30 g |
| pH | 6.8 |

TABLE 9

| Strain | OD 562 nm | Sugar consumed (g/L) | O-phosphoserine (g/L) |
|---|---|---|---|
| CA07-0012 | 23 | 40 | 1.7 |
| CA07-0012/pCL-Prmf-serA | 25 | 40 | 1.8 |
| CA07-0012/pCL-Prmf-serA*(G336V) | 23 | 37 | 2.2 |
| CA07-0012/pCL-Prmf-serA*(G336V, G337V) | 21 | 36 | 2.1 |
| CA07-0012/pCL-Prmf-serA*(G336V, R338V) | 22 | 37 | 2.2 |
| CA07-0012/pCL-Prmf-serA-(RBS)serC | 20 | 35 | 2.1 |
| CA07-0012/pCL-Prmf-serA*(G336V)-(RBS)serC | 18 | 31 | 2.5 |
| CA07-0012/pCL-Prmf-serA*(G336V, G337V)-(RBS)serC | 17 | 32 | 2.5 |
| CA07-0012/pCL-Prmf-serA*(G336V, R338V)-(RBS)serC | 16 | 30 | 2.6 |

As apparent from the data of Table 9, the *E. coli* CA07-0012 strain increased in the productivity of O-phosphoserine when it was transformed with serA, and the productivity of O-phosphoserine was increased to a greater extent upon the introduction of one of the three serA* mutants. The strains in which serA, or one of three serA* mutants and serC that were activated simultaneously showed higher productivity of O-phosphoserine than did those in which there was the sole activation of serA or serA*. The highest productivity of O-phosphoserine was detected in a strain in which the mutant serA* and serC were activated simultaneously.

Example 10: Preparation of PhnC/PhnD/PhnE Alkylphosphonate ABC Transporter (phnCDE Operon) Deficient *E. coli* Strain In *E. coli*, PhnC/PhnD/PhnE alkylphosphonate ABC transporter is reported to translocate O-phosphoserine into the cytoplasm (Wanner B L and Metcalf W W. FEMS Microbiol. Lett., 15:133-139, 1992). The phnCDE operon encoding a PhnC/PhnD/PhnE alkylphosphonate ABC transporter protein was deleted from a serB deletion strain to prepare the CA07-0016 strain. For the deletion of phnCDE, a pair of primers of SEQ ID NOS: 53 and 54 were employed. The deletion was performed in a manner similar to that of Example 5.

In addition, pCL-Prmf-serA*(G336V)-(RBS)serC, constructed in Example 8, was introduced into CA07-0016.

Example 11: Assay of phnCDE Operon Deficient *E. Coli* Strain for O-Phosphoserine Productivity The strains CA07-0016 and CA07-0016/pCL-Prmf-serA* (G336V)-(RBS)serC, prepared in Example 10, were evaluated for O-phosphoserine productivity. Each strain was spread over LB plates or LB (spectinomycine) plates and incubated overnight at 33° C. Afterwards, colonies appearing on the LB plates or the LB (spectinomycine) plates were inoculated into 25 mL of titer media of Table 8 using a platinum loop and cultured at 33° C. for 48 hours with shaking at 200 rpm. The results are summarized in Table 10, below.

TABLE 10

| Strain | OD 562 nm | Sugar consumed (g/L) | O-phosphoserine (g/L) |
|---|---|---|---|
| CA07-0012 | 22 | 40 | 1.8 |
| CA07-0016 | 23 | 38 | 2.0 |
| CA07-0012/pCL-Prmf-serA*(G336V)-(RBS)serC | 21 | 35 | 2.1 |
| CA07-0016/pCL-Prmf-serA*(G336V)-(RBS)serC | 20 | 40 | 2.4 |

As seen in Table 10, the phnCDE operon deletion strain showed only a slight increase in O-phosphoserine productivity.

Example 12: Preparation of Alkaline Phosphatase (phoA), Acid Phosphatase (aphA) Deficient *E. Coli* Strain The phosphoserine phosphatase deletion *E. coli* strain was additionally deleted the phoA gene coding for alkaline phosphatase and the aphA gene coding for acid phosphatase. A DNA fragment for use in deleting phoA was obtained by performing PCR on a pkD3 plasmid with a pair of primers of SEQ ID NOS: 55 and 56. On the other hand, a DNA fragment for use in deleting aphA was obtained using a pair of primers of SEQ ID NOS: 57 and 58 in the same manner. Each deletion strain was prepared in the same manner as in Example 5. The strain which deleted both phoA and aphA was prepared by electroporating the DNA fragment for aphA deletion into a competent cell of the phoA deletion strain which had been transformed again with pKD46. Thereafter, the transformants which were resistant to chloramphenicol were subjected to PCR to confirm the deletion of aphA, and then transformed with pCP20 to remove the antibiotic-resistant marker. The resulting mutant strains and their genotypes are summarized in Table 11, below.

TABLE 11

| Strain | Genotype |
|---|---|
| CA07-0013 | W3110 Δ serB Δ phoA |
| CA07-0015 | W3110 Δ serB Δ aphA |
| CA07-0018 | W3110 Δ serB Δ phoA Δ aphA |

To each deletion strain, pCL-Prmf-serA*(G336V)-(RBS)serC, constructed in Example 8, was introduced in the same manner as in Example 10.

Example 13: Assay of Alkaline Phosphatase (phoA), Acid Phosphatase (aphA) Deficient *E. coli* Strain for Ability to Degrade O-Phosphoserine The strains prepared in Example 12 were assayed for the productivity of OPS and the incapability of degrading OPS. Each strain was spread over LB plates or LB (spectinomycine) plates and incubated overnight at 33° C. Afterwards, colonies appearing on the LB plates or the LB (spectinomycine) plates were inoculated into 25 mL of titer media of Table 8 using a platinum loop and cultured at 33° C. for 72 hours with shaking at 200 rpm. The results are summarized in Table 12, below. Incapability of degrading OPS was evaluated by a change in phosphate ion level as determined by phosphate ion analysis.

TABLE 12

| Strain | OD 562 nm | Sugar consumed (g/L) | O-phosphoserine (g/L) | PO$_4$ (ppm) |
|---|---|---|---|---|
| CA07-0012 | 23 | 40 | 0.3 | 692 |
| CA07-0013 | 22 | 40 | 1.6 | 459 |
| CA07-0015 | 7.4 | 25 | 0 | 1098 |
| CA07-0018 | 19 | 40 | 1.7 | 487 |
| CA07-0012/pCL-Prmf-serA*(G336V)-(RBS)serC | 20 | 40 | 0.1 | 714 |
| CA07-0013/pCL-Prmf-serA*(G336V)-(RBS)serC | 16 | 40 | 1.8 | 385 |
| CA07-0018/pCL-Prmf-serA*(G336V)-(RBS)serC | 17 | 40 | 1.6 | 593 |

As seen in Table 12, the aphA deletion strain showed an abnormal growth phenomenon whereas the strains which lacked phoA or both phoA and aphA somewhat increased in O-phosphoserine productivity and decreased in the capability of degrading O-phosphoserine. On the other hand, the strain in which neither phoA nor aphA was deleted degraded the O-phosphoserine accumulated for 72 hours, with the concomitant increase of the PO$_4$ level.

Example 14: Preparation of phnCDE Operon, phoA and aphA Deficient Strains

The serB deficient strain (CA07-0012) was modified to further delete phnC/phnD/phnE alkylphosphonate ABC transporter-encoding phnCDE, alkaline phosphatase-encoding phoA, and acid phosphatase-encoding aphA. The strains thus prepared are given in Table 13, below. The one-step inactivation method described in Example 5 was employed to prepare the deletion mutants.

TABLE 13

| Strain | Genotype |
|---|---|
| CA07-0020 | W3110 Δ serB Δ phoA Δ phnCDE |
| CA07-0022 | W3110 Δ serB Δ phoA Δ aphA Δ phnCDE |

Into each of the deletion strains, the pCL-Prmf-serA*(G336V)-(RBS)serC, constructed in Example 8, was introduced in the same manner as in Example 10.

Example 15: Assay of phnCDE Operon, phoA and aphA Deficient *E. Coli* Strains for O-Phosphoserine Productivity The strains prepared in Example 14 were assayed for OPS productivity. Each strain was spread over LB plates or LB (spectinomycine) plates and incubated overnight at 33° C. Afterwards, colonies appearing on the LB plates or the LB (spectinomycine) plates were inoculated into 25 mL of titer media of Table 8 using a platinum loop and cultured at 33° C. for 72 hours with shaking at 200 rpm. The results are summarized in Table 14, below.

TABLE 14

| Strain | OD 562 nm | Sugar consumed (g/L) | O-phosphoserine (g/L) | PO$_4$ (ppm) |
|---|---|---|---|---|
| CA07-0012 | 23 | 40 | 0.3 | 692 |
| CA07-0020 | 18.3 | 40 | 1.9 | 262 |
| CA07-0022 | 19.1 | 40 | 2 | 263 |
| CA07-0012/pCL-Prmf-serA*(G336V)-(RBS)serC | 20 | 40 | 0.1 | 714 |
| CA07-0020/pCL-Prmf-serA*(G336V)-(RBS)serC | 17.6 | 40 | 2.5 | 174 |
| CA07-0022/pCL-Prmf-serA*(G336V)-(RBS)serC | 17 | 40 | 2.6 | 218 |

CA07-0020 and CA07-0022 were found to have increased OPS productivity and decreased ability to degrade O-phosphoserine, compared to CA07-0012. This property was also detected in the strains transformed further with pCL-Prmf-serA*(G336V)-(RBS)serC.

Example 16: Preparation of E. Coli Mutants Deficient of phnCDE Operon, phoA, and aphA Genes and Having Substitution of Phosphoglycerate Dehydrogenase (serA*)

In CA07-0022, 3-phosphoglycerate dehydrogenase-encoding serA was substituted with serA*(G336V), serA*(G336V, G337V), or serA*(G336V, R338G), all being reported to have feedback resistance to serine, on the chromosome, as follows. To introduce mutations into the serA gene on the chromosome, vectors were constructed as follows. PCR was performed with a pair of primers of SEQ ID NOS: 40 and 41 on serA*(G336V), serA*(G336V, G337V), and serA*(G336V, R338G), prepared in Example 7. After treatment with both SacI and BamHI, the PCR products thus obtained were cloned into pSG76C at the SacI and BamHI site. The resulting recombinant vector was transformed into E. coli BW which was then spread over LB plates. The colonies appearing on the plates were subjected to base sequencing, and the transformants into which mutations were introduced were selected. From them, plasmids were prepared using a typical miniprep method. According to the introduced mutations, the plasmids were named pSG76C-serA*(G336V), pSG76C-serA*(G336V, G337V) and pSG76C-serA*(G336V, R338G).

Each of the E. coli mutants was prepared as described previously (Posfai G, Kolisnychenko V, Bereczki Z and Blattner F R, Nucleic Acids Res. 27: 4409-4415, 1999), and the antibiotic-resistant marker gene was removed from them. To prepare the serA*(G336V) mutant, pSG76C-serA*(G336V) was introduced into a competent cell of CA07-0022 by electroporation. The strains resistant to chloramphenicol were subjected to PCR to confirm the introduction of serA*(G336V). The strain was transformed with pST76-ASceP (Posfai G, Kolisnychenko V, Bereczki Z and Blattner F R, Nucleic Acids Res. 27: 4409-4415, 1999) to remove the antibiotic-resistant marker gene. The resulting strain was named CA07-0022 serA*(G336V). The CA07-0022 serA*(G336V) strain was transformed with pSG76C-serA*(G336V, G337V) and pSG76C-serA*(G336V, R338G) in a similar manner to give serA*(G336V, G337V) and serA*(G336V, R338G) mutants, named CA07-0022 serA*(G336V, G337V) and serA*(G336V, R338G), respectively.

Example 17: Assay of E. Coli Mutants Deficient of phnCDE Operon, aphA, and aphA Genes and Having Substitution of Phosphoglycerate Dehydrogenase (serA*) for O-Phosphoserine Productivity The strains prepared in Example 16 were assayed for O-phosphoserine productivity. Each strain was spread over LB plates or LB (spectinomycine) plates and incubated overnight at 33° C. Afterwards, colonies appearing on the LB plates or the LB (spectinomycine) plates were inoculated into 25 mL of titer media of Table 8 using a platinum loop and cultured at 33° C. for 48 hours with shaking at 200 rpm. The results are summarized in Table 15, below.

TABLE 15

| Strain | OD 562 nm | Sugar consumed (g/L) | O-phosphoserine (g/L) |
|---|---|---|---|
| CA07-0022 | 22 | 40 | 2.2 |
| CA07-0022 serA*(G336V) | 21 | 35 | 2.7 |
| CA07-0022 serA*(G336V, G337V) | 20 | 36 | 2.8 |
| CA07-0022 serA*(G336V, R338G) | 20 | 38 | 2.7 |

The strains in which serA had been altered to sereine feedback-resistant genes showed somewhat decreased growth rates, but an increase in O-phosphoserine productivity.

Example 18: Preparation of Mutant E. Coli Strains Deficient of phnCDE Operon, phoA and aphA and Having Substituted Phosphoglycerate Dehydrogenase (serA*) and Enhanced 3-Phosphoserine Aminotransferase and Assay for O-Phosphoserine Productivity Into the strains prepared in Example 16, that is, CA07-0022 serA*(G336V), CA07-0022 serA*(G336V, G337V), and CA07-0022 serA*(G336V, R338G) was introduced in the plasmid prepared in Example 8, that is, pCL-Prmf-serC. The resulting mutants were evaluated for O-phosphoserine productivity in the same manner as in Example 9. The results are summarized in Table 16, below.

TABLE 16

| Strain | OD 562 nm | Sugar consumed (g/L) | O-phosphoserine (g/L) |
|---|---|---|---|
| CA07-0022/pCL-Prmf-serC | 20 | 38 | 2.9 |
| CA07-0022 serA*(G336V)/pCL-Prmf-serC | 19.5 | 34 | 3.45 |
| CA07-0022 serA*(G336V, G337V)/pCL-Prmf-serC | 20 | 33 | 3.55 |
| CA07-0022 serA*(G336V, R338G)/pCL-Prmf-serC | 19 | 35 | 3.6 |

As seen in Table 16, the serC-activated strains were found to be improved in O-phosphoserine productivity. This phenomenon was more apparent in the strain in which serA was modified into a serine feedback-resistant gene.

Example 19: Pyrimidine Nucleotide Transhydrogenase (PntAB)-Enhanced Strain and Construction of Glutamate Dehydrogenase (GdhA) Containing Vector To prepare a strain in which pntAB encoding for pyrimidine nucleotide transhydrogenase is upregulated, the pntAB promoter was changed with a trc promoter using a mutant loxP system (Arakawa H et al., BMC Biotechnol. 1: 7, 2001). In this regard, PCR was performed on the pmlox-trc (ref) plasmid using a pair of primers of SEQ ID NOS: 59 and 60, and the PCR product thus obtained was introduced into a competent cell of CA07-0022 serA*(G336V) anchoring pKD46 by electroporation. The transformants which showed resistance to chloramphenicol were subjected to PCR to confirm the replacement of the promoter, followed by transformation with pJW168 (Le Borgne S et al., Methods Mol. Biol. 267: 135-43, 2004) to remove the antibiotic-resistant marker gene. The resulting strain was named CA07-0022 serA*(G336V) P(trc)-pntAB. The primers used for the PCR were designed on the basis of the information about the K12 W3110 gene (GenBank accession number AP002223, AP002224) and its neighboring nucleotide sequences, registered in the NHI GenBank.

The glutamate dehydrogenase-encoding gdhA gene was amplified using PCR with a pair of primers of SEQ ID NOS: 61 and 62 to give a single polynucleotide. Both the primers of SEQ ID NOS: 61 and 62 have the restriction enzyme site HindIII. The primers were designed on the basis of the information about the K12 W3110 gene (GenBank accession number AP 002380) and its neighboring nucleotide sequences, registered in the NHI GenBank.

PCR started with denaturation at 94° C. for 3 min and proceeded with 25 cycles of denaturing at 94° C. for 30 sec, annealing at 56° C. for 30 sec and extending at 72° C. for 2 min, followed by extending at 72° C. for 7 min. As a result, a 1714-bp-long polynucleotide was obtained. After treatment with HindIII, the PCR product was cloned into pCC1BAC at the HindIII site and introduced into E. coli DH5α which was then spread over LB plates. Base sequencing allowed the selection of the developed colonies that had no mutations in their gdhA gene. The plasmid was isolated using a typical miniprep method and named pCC1BAC-P (native)-gdhA.

Example 20: Introduction of pntAB and gdhA into OPS-Producing Strain and Assay for OPS Productivity To prepare an OPS-producing strain in which pntAB and gdhA were upregulated, the CA07-0022 serA*(G336V) strain or the CA07-0022 serA*(G336V) P(trc)-pntAB strain was transformed with pCL-P(trc)-serA*(G336V)-serf and pCC1BAC-P(native)-gdhA individually or in combination, as shown in the following table. Each transformant was incubated overnight at 33° C. on LB plates. The colonies were inoculated into the 25 mL of titer media of Table 8 using a platinum loop and cultured at 33° C. for 48 hours with shaking at 200 rpm.

TABLE 17

| Strain | OD 562 nm | Sugar consumed (g/L) | OPS (g/L) |
| --- | --- | --- | --- |
| CA07-0022 serA*(G336V)/ pCL-P(trc)-serA*(G336V)-serC | 20 | 37 | 3.1 |
| CA07-0022 serA*(G336V) P(trc)-pntAB/ pCL-P(trc)-serA*(G336V)-serC | 19 | 35 | 3.4 |
| CA07-0022 serA*(G336V) P(trc)-pntAB/ pCC1BAC-P(native)-gdhA | 7.2 | 11 | 0.2 |
| CA07-0022 serA*(G336V) P(trc)-pntAB/ pCC1BAC-P(native)-gdhA/ pCL-P(trc)-serA*(G336V)-serC | 27.0 | 40 | 3.95 |

As seen in Table 17, the strain was improved in O-phosphoserine productivity when pntAB was upregulated therein. The upregulation of both pntAB and gdhA brought about a bigger increase in O-phosphoserine productivity, as compared to the control. Hence, pntAB and gdhA are understood to play an important role in the production of OPS.

Example 21: Construction of Vectors Carrying Genes Encoding E. coli O-Acetylserine/Cysteine Efflux Protein (ydeD), O-Acetylserine/Cysteine Efflux Permease (yfiK), Homoserine/Homoserine Lactone Efflux Protein (rhtB), Threonine/Homoserine Efflux Protein (rhtC), Arsenite/Antimonite Transporter (asrB), and Leucine/Isoleucine/Valine Transport Subunit (livHM)

The release of the produced O-phosphoserine out of the cell requires a suitable export factor none of which have, however, been reported previously. In this context, six genes, that is, O-acetylserine/cysteine efflux protein-encoding ydeD, O-acetylserine/cysteine efflux permease-encoding yfiK (Franke I, Resch A, Dassler T, Maier T and Bock A, J. Bacteriology, 185: 1161-166, 2003), homoserine/homoserine lactone efflux protein-encoding rhtB, threonine/homoserine efflux protein-encoding RhtC, arsenite/antimonite transporter-encoding asrB, and leucine/isoleucine/valine transport subunit-encoding livHM were selected from among the previously reported variety of transporter genes, and were cloned and evaluated.

Each gene was obtained by performing PCR on the genomic DNA of E. coli W3110, with a pair of primers of SEQ ID NOS: 63 and 64 for ydeD, with a pair of primers of SEQ ID NOS: 65 and 66 for yfiK, with a pair of primers of SEQ ID NOS: 67 and 68 for rhtB, with a pair of primers of SEQ ID NOS: 69 and 70 for rhtC, with a pair of primers of SEQ ID NOS: 71 and 72 for asrB, and with a pair of primers of SEQ ID NOS: 73 and 74 for livHM. After treatment with EcoRV and HindIII, each of the PCR products thus obtained was cloned at the EcoRV and HindIII site into the pCL-Prmf-GFP, to give recombinant vectors, named pCL-Prmf-ydeD, pCL-Prmf-yfiK, pCL-Prmf-rhtB, pCL-Prmf-rhtC, pCL-Prmf-arsB, and pCL-Prmf-livHM.

Example 22: Introduction of Vectors Carrying Genes Encoding E. coli YdeD, YfiK, RhtB, RhtC, AsrB, livhm into O-Phosphoserine-Producing Strain and Assay for O-Phosphoserine Productivity The CA07-0022 serA*(G336V) strain was transformed with the six plasmids constructed in Example 21 and evaluated for O-phosphoserine productivity in the same manner as in Example 9. The results are given in Table 18, below.

TABLE 18

| Strain | OD 562 nm | Sugar consumed (g/L) | O-phosphoserine (g/L) |
|---|---|---|---|
| CA07-0022 serA*(G336V) | 22.1 | 37.7 | 2.5 |
| CA07-0022 serA*(G336V)/ pCL-Prmf-ydeD | 7.4 | 22.3 | 0.69 |
| CA07-0022 serA*(G336V)/ pCL-Prmf-yfiK | 21 | 40 | 2.55 |
| CA07-0022 serA*(G336V)/ pCL-Prmf-rhtB | 23 | 40 | 2.8 |
| CA07-0022 serA*(G336V)/ pCL-Prmf-rhtC | 22.5 | 40 | 2.75 |
| CA07-0022 serA*(G336V)/ pCL-Prmf-arsB | 21 | 38 | 2.4 |
| CA07-0022 serA*(G336V)/ pCL-Prmf-livHM | 8 | 23 | 0.8 |

As shown in Table 18, the strains transformed with ydeD, mdtG or livHM exhibited decreased growth rate and decreased OPS productivity whereas transformation with yfiK, rhtB or rhtC increased growth rate and OPS productivity (Table 18).

Example 23: Preparation of Phosphoglycerate Mutase (gpmI, gpmA and gpmB) Deficient Strain gpmI, gpmA, and gpmB, each encoding phosphoglycerate mutase, were deleted solely or in combination from CA07-0022 serA*(G336V) to produce the mutant strains named CA07-0022 serA*(G336V)ΔgpmI, CA07-0022 serA*(G336V)ΔgpmA, CA07-0022 serA*(G336V)ΔgpmB, CA07-0022 serA*(G336V)ΔgpmIΔgpmA, CA07-0022 serA*(G336V)ΔgpmAΔgpmB, and CA07-0022 serA*(G336V)ΔgpmIΔgpmAΔgpmB, respectively. The gpmA- and gpmB-deletion strains were prepared in a manner similar to that of Example 5, using a pair of primers of SEQ ID NOS: 75 and 76 for gpmA and a pair of primers of SEQ ID NOS: 81 and 82 for gpmB. For the construction of a gpmI deletion strain, as described in Example 16, a gpmI mutation containing a stop codon was introduced using pSG76C. A gpmI mutant containing a stop codon was amplified by sewing PCR using primers of SEQ ID NOS: 77 to 81, with the genomic DNA of K12 W3110 serving as a template, and cloned into pSG76 at the SacI/BamHI site.

Example 24: Assay of gpmI, gpmA and gpmB Deficient Strains for OPS Productivity The strains prepared in Example 23 were evaluated for OPS productivity in the same manner as in Example 9. The results are summarized in Table 19, below.

TABLE 19

| Strain | OD562 nm | Sugar consumed (g/L) | OPS (g/L) |
|---|---|---|---|
| CA07-0022 serA*(G336V) | 23 | 40 | 2.4 |
| CA07-0022 serA*(G336V)ΔgpmI | 22 | 38 | 2.5 |
| CA07-0022 serA*(G336V)ΔgpmA | 20 | 34 | 2.8 |
| CA07-0022 serA*(G336V)ΔgpmB | 20 | 34 | 2.7 |
| CA07-0022 serA*(G336V)ΔgpmIΔgpmA | 19 | 32 | 2.6 |
| CA07-0022 serA*(G336V)ΔgpmAΔgpmB | 21 | 35 | 3.3 |

As can be seen in Table 19, when each of gpmI, gpmA and gpmB was deleted and the others not deleted, the sugar consumption of the mutant strains decreased, but their OPS productivity increased, compared to the mother strain. Particularly, the strain devoid of both gpmA and gpmB had similar sugar consumption, but increased OPS productivity, compared to the strains devoid of either gpmA or gpmB. Therefore, the deletion of gpmI, gpmA and gpmB is understood to produce an increased amount of 3-phosphoglycerate, a precursor of OPS, thus leading to increased OPS production.

Example 25: Preparation of 2-Amino-3-Ketobutyrate CoA Ligase (kbl), L-Serine Deaminase I (sdaA) Deficient Strains The kbl gene coding for 2-amino-3-ketobutyrate CoA ligase and the sdaA gene coding for L-serine deaminase I were deleted from CA07-0022 serA*(G336V) to yield CA07-0022 serA*(G336V) Δkbl, and CA07-0022 serA*(G336V) ΔsdaA, respectively. The kbl- and the sdaA-deletion strain were prepared in a manner similar to that of Example 5, using a pair of primers of SEQ ID NOS: 83 and 84 for kbl and a pair of primers of SEQ ID NOS: 85 and 86 for sdaA.

Example 26: Assay for OD and Sugar Consumption of kbl/sdaA Deficient Strains According to Glycine Concentration The strains prepared in Example 25 were evaluated for OD, sugar consumption, and O-phosphoserine productivity when they were incubated in the same medium condition as described in Table 8 of Example 9, with the exception that glycine was used in an amount of from 0 to 2.5 g/L.

TABLE 20

| Glycine Conc. (g/L) | Strain | OD 562 nm | Sugar Consumed (g/L) | OPS (g/L) |
|---|---|---|---|---|
| 0 | CA07-0022 serA*(G336V) | 8 | 10 | 0.7 |
|  | CA07-0022 serA*(G336V)Δkbl | 7 | 8 | 0.7 |
|  | CA07-0022 serA*(G336V)ΔsdaA | 9 | 10 | 0.7 |
| 1 | CA07-0022 serA*(G336V) | 15 | 30 | 1.5 |

TABLE 20-continued

| Glycine Conc. (g/L) | Strain | OD 562 nm | Sugar Consumed (g/L) | OPS (g/L) |
|---|---|---|---|---|
| | CA07-0022 serA*(G336V)Δkbl | 14 | 28 | 1.2 |
| | CA07-0022 serA*(G336V)ΔsdaA | 22 | 39 | 2.4 |
| 2 | CA07-0022 serA*(G336V) | 19 | 35 | 2.1 |
| | CA07-0022 serA*(G336V)Δkbl | 17 | 32 | 1.7 |
| | CA07-0022 serA*(G336V)ΔsdaA | 23 | 40 | 2.5 |
| 2.5 | CA07-0022 serA*(G336V) | 22 | 38 | 2.5 |
| | CA07-0022 serA*(G336V)Δkbl | 23 | 39 | 2.7 |
| | CA07-0022 serA*(G336V)ΔsdaA | 24 | 40 | 2.3 |

As can seen in Table 20, the OD and the rate of sugar consumption in all three of the strains increased when the glycine level in the medium was increased. Particularly, the sdaA-deletion strain showed a significant increase in OD and sugar consumption rate at a glycine concentration of 1 g/L. The OPS productivity of the kbl deletion strain greatly improved in the presence of 2.5 g/L glycine.

Example 27: Preparation of iclR Deficient Strain

The transcription factor iclR was deleted from CA07-0022 serA*(G336V) to produce CA07-0022 serA*(G336V) ΔiclR. The deletion mutant strain was prepared using the one-step inactivation method as in Example 5 and the antibiotic-resistant marker gene was removed. For the preparation of the iclR deletion strain, PCR was performed with a pair of primers of SEQ ID NOS: 87 and 88.

Example 28: Assay of the iclR Deficient Strain for OPS Productivity

The strain prepared in Example 27 was evaluated for OPS productivity in the same manner as in Example 9.

TABLE 21

| Strain | OD562 nm | Sugar consumed (g/L) | OPS (g/L) |
|---|---|---|---|
| CA07-0022 serA*(G336V) | 22 | 38 | 2.5 |
| CA07-0022 serA*(G336V)ΔiclR | 22 | 40 | 2.7 |

As is apparent from the data of Table 21, the OPS productivity of the iclR deletion strain was found to increase.

Example 29: Construction of Vectors Carrying E. Coli Acetyl CoA Synthetase (acs), Pyruvate Oxidase Monomer (poxB), Acetate Kinase (ackA) and Phosphate Acetyltransferase (pta)

To enhance the production and reuse of acetate in the O-phosphoserine-producing strain, expression plasmids carrying acetyl CoA synthetase-encoding acs, pyruvate oxidase monomer-encoding poxB, acetate kinase-encoding ackA and phosphate acetyltransferase-encoding pts, respectively, were constructed.

Each gene was obtained by performing pfu PCR on the genomic DNA of E. coli W3110 with a pair of primers of SEQ ID NOS: 89 and 90 for acs, with a pair of primers of SEQ ID NOS: 91 and 92 for poxB, and with a pair of primers of SEQ ID NOS: 93 and 94 for ackA and pta. After treatment with HindIII, each of the PCR products thus obtained was cloned at the EcoRV and HindIII site into the pCL-Prmf-GFP vector constructed by inserting an E. coli rmf promoter into pCL1920, so as to give pCL-Prmf-acs, pCL-Prmf-poxB, and pCL-Prmf-ackA-pta. Subsequently, these plasmids were treated with EcoRI to obtain DNA inserts, that is, Prmf-acs, Prmf-poxB, and Prmf-ackA-pta, which were then introduced into pCC1BAC (EcoRI) (CopyControl™ pcc1BAC™ Vector, Epicentre. Cat. Nos. CBAC311) to construct pCC1BAC-Prmf-acs, pCC1BAC-Prmf-poxB, and pCC1BAC-Prmf-ackA-pta, respectively.

Example 30: Preparation of E. Coli acs, poxB, ackA, pta-Enhanced OPS-Producing Strain and Assay for OPS Productivity The CA07-0022 serA*(G336V) strain was transformed with the three vectors prepared in Example 29 and assayed for OPS productivity in the same manner as in Example 9.

TABLE 22

| Strain | OD562 nm | Sugar consumed (g/L) | OPS (g/L) |
|---|---|---|---|
| CA07-0022 serA*(G336V) | 21.9 | 35.5 | 2.45 |
| CA07-0022 serA*(G336V)/ pCC1BAC-Prmf-acs | 23.6 | 40 | 2.65 |
| CA07-0022 serA*(G336V)/ pCC1BAC-Prmf-poxB | 18.3 | 36.8 | 1.86 |
| CA07-0022 serA*(G336V)/ pCC1BAC-Prmf-ackA-pta | 21.8 | 40 | 2.65 |

As can be seen in Table 22, the growth rate of the strain transformed with poxB decreased whereas the introduction of acs or ackA-pta increased the growth rate and OPS productivity.

Example 31: Construction of Vectors Carrying E. Coli Malate Synthase A (aceB), Isocitrate Lyase Monomer (aceA), Phosphoenolpyruvate Carboxykinase (pckA), Malate Synthase G (glcB), and Malate Dehydrogenase (maeB)

Plasmids which allow the expression of both malate synthase A-encoding aceB and isocitrate lyase monomer-encoding aceA, phosphoenolpyruvate carboxykinase-encoding pckA, malate synthase G-encoding glcB, and malate dehydrogenase-encoding maeB in E. coli, respectively, were constructed.

The genes were prepared by performing pfu PCR on the genomic DNA of E. coli W3110 with a pair of primers of SEQ ID NOS: 95 and 96 for aceBA, with a pair of primers of SEQ ID NOS: 97 and 98 for pckA, with a pair of primers of SEQ ID NOS: 99 and 100 for glcB, and with a pair of primers of SEQ ID NOS: 101 and 102 for maeB. After treatment with HindIII, each of the PCR products thus obtained was cloned at the EcoRV and HindIII site into the pCL-Prmf-GFP vector constructed by inserting an E. coli rmf promoter into pCL1920, so as to give pCL-Prmf-aceBA, pCL-Prmf-pckA, pCL-Prmf-glcB, and pCL-Prmf-maeB.

Example 32: Preparation of E. Coli aceB, aceA, pckA, glcB and maeB-Enhanced OPS-Producing Strain and Assay for O-Phosphoserine Productivity The CA07-0022 serA*(G336V) strain was transformed with the four vectors prepared in Example 31 and assayed for O-phosphoserine productivity in the same manner as in Example 9.

TABLE 23

| Strain | OD 562 nm | Sugar consumed (g/L) | OPS (g/L) |
| --- | --- | --- | --- |
| CA07-0022 serA*(G336V) | 23 | 40 | 2.4 |
| CA07-0022 serA*(G336V)/pCL-Prmf-aceBA | 20 | 36 | 1.9 |
| CA07-0022 serA*(G336V)/pCL-Prmf-pckA | 10 | 11 | 0 |
| CA07-0022 serA*(G336V)/pCL-Prmf-glcB | 21 | 40 | 2.8 |
| CA07-0022 serA*(G336V)/pCL-Prmf-maeB | 21 | 40 | 2.9 |

As can be seen in Table 23, the sugar consumption rate and OPS productivity of the strain somewhat decreased when transformed with aceBA and the growth rate significantly decreased when transformed with pckA whereas the introduction of glcB or maeB increased OPS productivity.

Example 33: Construction of Vectors Carrying Glyoxylate Carboligase (glc), Tartronate Semialdehyde Reductase 2 (glxR), and Glycerate Kinase II (glxK)

Glyoxylate carboligase-encoding gcl, tartronate semialdehyde reductase 2-encoding glxR, and glycerate kinase II-encoding glxK, all of which are involved in the conversion of glyoxylate into 3-phosphoglycerate, were cloned as follows. The genes were obtained by performing PCR on the genomic DNA of E. coli W3110 with a pair of primers of SEQ ID NOS: 103 and 104 for gcl, and with pairs of primers of SEQ ID NOS: 105 to 108 for glxR-glxK. After digestion with EcoRV and HindIII, each of the PCR products was cloned at the EcoRV and HindIII sites into the pCL-Prmf-GFP vector constructed by inserting an E. coli rmf promoter into pCL1920 to afford recombinant plasmids, named pCL-Prmf-gcl, pCL-Prmf-glxR-glxK, and pCL-Prmf-glxR-glxK-Prmf-gcl, respectively.

Example 34: Introduction of Vectors Carrying glc, glxR, glxK into O-Phosphoserine-Producing Strain and Assay for O-Phosphoserine Productivity The three plasmids constructed in Example 33 were introduced into CA07-0022 serA*(G336V) which were then evaluated for O-phosphoserine productivity in the same manner as in Example 9. The results are summarized in Table 24, below.

TABLE 24

| Time | Strain | OD 562 nm | Sugar consumed (g/L) | O-phosphoserine (g/L) |
| --- | --- | --- | --- | --- |
| 24 h | CA07-0022 serA*(G336V) | 15.6 | 24 | 1.25 |
| | CA07-0022 serA*(G336V)/pCL-Prmf-gcl | 19.6 | 29.7 | 1.2 |
| | CA07-0022 serA*(G336V)/pCL-Prmf-glxR-glxK | 21 | 33 | 1.3 |
| | CA07-0022 serA*(G336V)/pCL-Prmf-glxR-glxK-Prmf-gcl | 18.4 | 29.7 | 1.03 |
| 48 h | CA07-0022 serA*(G336V) | 23 | 40 | 2.4 |
| | CA07-0022 serA*(G336V)/pCL-Prmf-gcl | 31.5 | 40 | 1.67 |
| | CA07-0022 serA*(G336V)/pCL-Prmf-glxR-glxK | 26.2 | 40 | 1.5 |
| | CA07-0022 serA*(G336V)/pCL-Prmf-glxR-glxK-Prmf-gcl | 22 | 40 | 1.61 |

As can be seen in Table 24, the final O-phosphoserine productivity of the strains transformed respectively with gcl, glxR-glxK and glxR-glxK-gcl was decreased, but growth rate and sugar consumption rate were increased, compared to the CA07-0022 serA*(G336V) strain itself. Particularly, the introduction of glxR-glxK was found to have the greatest increase on growth rate and sugar consumption rate.

Example 35: Evaluation of O-phosphoserine-Producing Strain in a Fermentor

CA07-0022 serA*(G336V)/pCL-Prmf-serA*(G336V)-serC strains were incubated at 33° C. for 24 hours on MMYE agar plates (2 g/L glucose, 2 mM magnesium sulfate, 0.1 mM calcium chloride, 6 g/L sodium pyrophosphate, 0.5 g/L sodium chloride, 3 g/L potassium dihydrogen phosphate, 10 g/L yeast extract, 18 g/L agar) containing 50 μg/mL spectinomycine. The resulting colonies were scraped from 1/10 of the area of each agar plate, inoculated into a 50 μg/mL spectinomycine-containing seed medium, 10 g/L glucose, 0.5 g/L magnesium sulfate, 3 g/L potassium dihydrogen phosphate, 10 g/L yeast extract, 0.5 g/L sodium chloride, 1.5 g/L ammonium chloride, 12.8 g/L sodium pyrophosphate, 1 g/L glycine) in a baffle flask, and incubated at 30° C. for six hours while shaking at 200 rpm. To 300 mL of a main medium in a 1 L fermentor, the resulting seed culture in an amount as large as 16% of the volume of the main medium was added, followed by incubation at 33° C. and pH 7.0. The main medium had the composition given in Table 25, below.

TABLE 25

| [Composition of Main Medium] | |
| --- | --- |
| Glucose | 20 g/L |
| Magnesium sulfate | 0.3 g/L |
| Potassium dihydrogen phosphate | 1.5 g/L |
| Yeast extract | 5 g/L |
| Ammonium sulfate | 5 g/L |
| Tryptone | 10 g/L |

TABLE 25-continued

| | |
|---|---|
| Glycine | 2 g/L |
| Sodium chloride | 0.5 g/L |
| Sodium citrate | 1 g/L |
| Iron sulfide | 75 mg/L |
| Calcium chloride | 15 mg/L |
| Trace elements | 1 ml/L |
| [Trace elements] | |
| Cobalt chloride | 0.7 g/L |
| Zinc sulfate | 0.3 g/L |
| Molybdate | 0.15 g/L |
| Boric acid | 1.2 g/L |
| Manganese sulfate | 1.6 g/L |
| Copper sulfate | 0.25 g/L |

During incubation, the pH of the culture medium was adjusted to 7.0 with ammonia water. Upon the depletion of glucose from the culture medium, fed-batch-type fermentation was conduced by adding a 520 g/L glucose solution. Following fermentation for 80 hours, O-phosphoserine was produced at a concentration of 19.5 g/L as measured by HPLC.

Development and Characterization of
O-Phosphoserine (OPS) Sulfhydrylase (OPSS)

Example 36: Development of OPS Sulfhydrylase (OPSS)

*Aeropyrum pernix*, *Mycobacterium tuberculosis*, and *Trichomonas vaginalis* are reported to have O-phosphoserine sulfhydrylase (OPSS), an enzyme that employs O-phospho-L-serine (OPS), instead of O-acetyl serine (OAS) in *E. coli*, as a substrate for the synthesis of cysteine (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006). Based on the report, the present inventors found two types of OPS sulfhydrylase, which converts OPS into cysteine, from *Aeropyrum pernix* and *Mycobacterium tuberculosis* H37Rv. Of them, the *Mycobacterium tuberculosis* H37Rv-derived OPSS enzyme was used for screening amino acid homology. As a result, three types of OPSS were secured from *Mycobacterium smegmatis* str. MC2 155, *Rhodococcus jostii* RHA1, and *Nocardia farcinica* IFM 10152.

To obtain OPSS from each strain, a pET28a vector system (Novagen), which is typically used for enzyme expression, was constructed. Each templates and primers for use in cloning the five different OPS sulfhydrylase genes and the resulting recombinant plasmids are summarized in Table 26, below. Suitable combinations of the templates and the primers, as given in Table 26, were used for PCR for amplifying respective OPSS genes. The PCR products and the pET28a vector were digested with NdeI and HindIII (37° C. for 3 hours). Each of the gene fragments was ligated to the digested pET28a vector (Novagen). Base sequencing confirmed the construction of the expression vectors carrying the each OPSS genes. The enzyme expression vectors were introduced into *E. coli* (DE3) to produce strains capable of expressing five OPSS enzymes. Enzyme names are given in Table 26, below.

TABLE 26

| Enzyme | Vector | Template | Primer |
|---|---|---|---|
| Ape-OPSS | pET28a-Ape-OPSS | Synthetic DNA | SEQ ID NOS: 109 and 110 |
| Mtb-OPSS | pET28a-Mtb-OPSS | Mtb Genomic DNA | SEQ ID NOS: 111 and 112 |
| Msm-OPSS | pET28a-Msm-OPSS | Msm Genomic DNA | SEQ ID NOS: 113 and 114 |
| Rjo-OPSS | pET28a-Rjo-OPSS | Rjo Genomic DNA | SEQ ID NOS: 115 and 116 |
| Nfa-OPSS | pET28a-Nfa-OPSS | Nfa Genomic DNA | SEQ ID NOS: 117 and 118 |

Expression of the enzymes was conducted according to the instructions of the pET system manufacturer (Novagen). Single colonies of each strain from the LB plates were inoculated into 5 mL of LB broth and incubated at 37° C. for 16 hours while shaking at 200 rpm. The cultures were transferred to 25 mL of fresh LB broth (in 250 mL flasks) and incubated to an $OD_{600}$ of 0.5-0.6 (for 2-3 hours) in the same condition, immediately after which 1 mM IPTG was added to the media to induce the enzymes to be expressed during incubation at 18° C. for 18 hours while shaking at 120 rpm. The enzymes were purified using Ni-NTA columns for His-tag, with the aid of His SpinTrap (GE Healthcare). Of the five OPSS enzymes thus isolated, four were found to be in soluble forms, with one (Rjo-OPSS) being an inclusion body, as analyzed by 14% SDS-PAGE electrophoresis.

Example 37: Assay of OPS Sulfhydrylase (OPSS) for Cysteine Synthesis Activity

The OPS sulfhydrylase enzymes obtained from the four microorganism strains were assayed for ability to catalyze the conversion of O-phosphoserine (OPS) to cysteine. With regard to assay conditions and methods (cysM enzyme assay), reference was made to previous reports (Mino K and Ishikawa K, FEBS letters, 551: 133-138, 2003; Burns K E, Baumgart S, Dorrestein P C, Zhai H, McLafferty F W and Begley T P, J. Am. Chem. Soc., 127: 11602-11603, 2005; Westrop G D, Goodall G, Mottram J C and Coombs G H, J. Biol. Chem., 281: 25062-25075, 2006). The amount of the substrate used is represented by a unit of mL. Assay conditions for enzyme activity are summarized in Table 27, below.

TABLE 27

| Stock soln | Final Conc. | Blank | OPS sulfhydrylase |
|---|---|---|---|
| 6x his-enzyme | — | | 40 (50 mg) |
| 1M HEPES(pH7.4) | 100 mM HEPES | 100 | 100 |
| 0.5M $Na_2S$ | 10 mM $Na_2S$ | 20 | 20 |
| 10 mM PLP | 0.2 mM PLP | 20 | 20 |
| 100 mM OPS | 5 mM OPS | 0 | 50 |
| DW | | 790 | 750 |
| Total | | 1000 | 1000 |

Reaction solutions excepting of the enzymes were incubated at 37° C. for 5 min, after which 50 mg of purified OPS sulfhydrylase was added to the reaction solution. At predetermined times during incubation at 37° C., 100 mL of the enzyme reactions was taken and mixed with 100 mL of 33.2% TCA to stop the enzymatic reaction. The cysteine concentrations of the enzyme reactions were quantitatively analyzed by measuring absorbance at $OD_{560}$ according to the Gaitonde method. Cysteine synthesis activities of the four different OPS sulfhydrylase enzymes are summarized in Table 28, below. The cysteine synthesis titers of the OPSS enzymes are expressed as cysteine conversion rates with reaction time.

TABLE 28

| | Cysteine Conversion Rate (%) | | |
|---|---|---|---|
| | 10 min | 30 min | 60 min |
| Ape-OPSS | 63.4 | 89.7 | 97.4 |
| Mtb-OPSS | 1.7 | 4.8 | 10.1 |
| Msm-OPSS | 12.8 | 25 | 43.7 |
| Nfa-OPSS | 0.1 | 0.1 | 0.2 |

The OPS sulfhydrylase enzymes derived from *Aeropyrum pernix* and *Mycobacterium tuberculosis* H37Rv, which were previously reported (Mino K and Ishikawa K, FEBS letters, 551: 133-138, 2003; Westrop G D, Goodall G, Mottram J C and Coombs G H, J. Biol. Chem., 281: 25062-25075, 2006), were confirmed to have the activity of using OPS as a substrate to synthesize cysteine. The cysteine synthesis activity of the novel *Mycobacterium smegmatis* str. MC2 155-derived OPS sulfhydrylase, which was obtained by screening amino acid homology with the Mtb-OPSS enzyme, was first found. As seen in the data of Table 28, the conversion rate from OPS into cysteine of Ape-OPSS reached near 100% in one hour. The final conversion rate of the Msm-OPSS enzyme, which was newly selected through enzyme screening on the basis of previously reported *Mycobacterium tuberculosis* H37Rv-derived OPSS, was 43.7% that was 4.3 times as high as that of Mtb-OPSS. On the other hand, the novel *Nocardia farcinica* IFM 10152-derived OPS sulfhydrylase, obtained by the homology screening, exhibited insufficient activity of converting O-phosphoserine into cysteine.

Example 38: Preparation of Mtb-T and Msm-T that Encode C-Terminally 5 Amino Acid Residues Truncated Mtb-OPSS and Msm-OPSS

*Mycobacterium tuberculosis* H37Rv-derived OPSS (Mtb-OPSS), which catalyzes the conversion of OPS to cysteine with the aid of the additional enzymes mec+ and cysO, is reported to be able to use an $S^{2-}$ containing sulfur source in converting OPS to cysteine even in the absence of the additional enzymes when five C-terminal amino acid residues are removed therefrom (Agren D, Schnell R and Schneider G, FEBS letters, 583: 330-336, 2009). On the basis of this report, Mtb-T (SEQ ID NO: 11), which can rapidly convert OPS in the presence of $S^{2-}$ as a sulfur source, was obtained. Msm-T was also obtained from Msm-OPSS (SEQ ID NO: 9) that shares an amino acid homology with Mtb-OPSS. Expression vectors carrying the two enzyme mutants were constructed. In this regard, pfu PCR was performed on the genomic DNA of *Mycobacterium tuberculosis* H37Rv or *Mycobacterium smegmatis* in the presence of a pair of primers of SEQ ID NOS: 119, 120, 121 and 122. The OPSS gene fragments thus obtained were treated with NdeI and HindIII and were cloned into the pET28a vector digested with the same restriction enzymes to construct recombinant expression vectors named pET28a-Mtb-T and pET28a-Msm-T, respectively. The recombinant expression vectors were introduced into *E. coli* (DE3). The expression of the two mutant OPSS enzymes was confirmed by 14% SDS PAGE. The two mutant OPSS enzymes are purified and expressed in the same conditions as in Example 36. As a result, Mtb-T (SEQ ID NO: 11) and Msm-T (SEQ ID NO: 10) were obtained.

Example 39: Assay of Mtb-T and Msm-T for Cysteine Conversion Activity

On the basis of the report that *Mycobacterium tuberculosis* H37Rv-derived OPSS mutants devoid of five C-terminal amino acid residues show increased affinity for an $S^{2-}$ group-containing sulfur source even in the absence of subsidiary enzymes (Agren D, Schnell R and Schneider G, FEBS letters, 583: 330-336, 2009), Mtb-T and Msm-T were obtained. They were evaluated for enzymatic activity by measuring final cysteine conversion rates. Enzymatic activity was assayed in the same condition and manner as in Example 37. The produced cysteine was quantitatively analyzed using the Gaitonde method.

TABLE 29

| | Cysteine Conversion Rate (%) | | |
|---|---|---|---|
| | 10 min | 30 min | 60 min |
| Mtb-T | 9.5 | 18.6 | 37.1 |
| Msm-T | 20.3 | 54.6 | 100 |

As seen in Table 29, Msm-T, being devoid of the five C-terminal amino acid residues of *Mycobacterium smegmatis* str. MC2 155-derived OPSS allowed the conversion of cysteine from the substrate at a rate of 100% in one hour.

When its amino acid sequence was modified, the O-phosphoserine sulfhydrylase (OPSS) can more effectively catalyze the biosynthesis of L-cysteine.

Example 40: Requirement of Cofactor for OPS Sulfhydrylase Activity

To examine the effect of cofactors on the cysteine conversion of OPSS, the cysteine conversion rate of Msm-T was measured in the absence or presence of PLP (pyridoxal-5'-phosphate) and DTT (dithiothreitol). In this regard, the substrates of 50 mM OPS broth and 100 mM $Na_2S$ were reacted at 37° C. for 30 min in the presence of 25 mM DTT or 0.2 mM PLP. The cysteine thus produced was quantitatively analyzed using the Gaitonde method. As seen in Table 30, the cysteine conversion rate in the presence of both PLP and DTT was 2.3 times as large as that in the absence of both PLP and DTT. Thus, both PLP and DTT were observed to have a positive influence on the conversion.

TABLE 30

| Msm-T | Cysteine Conversion Rate (%) |
|---|---|
| (−) PLP, (−) DTT | 23.62 |
| (+) PLP, (−) DTT | 33.21 |
| (−) PLP, (+) DTT | 40.08 |
| (+) PLP, (+) DTT | 54.65 |

Example 41: The Influence of Temperature on the Activity of OPS Sulfhydrylase

Figure 2:
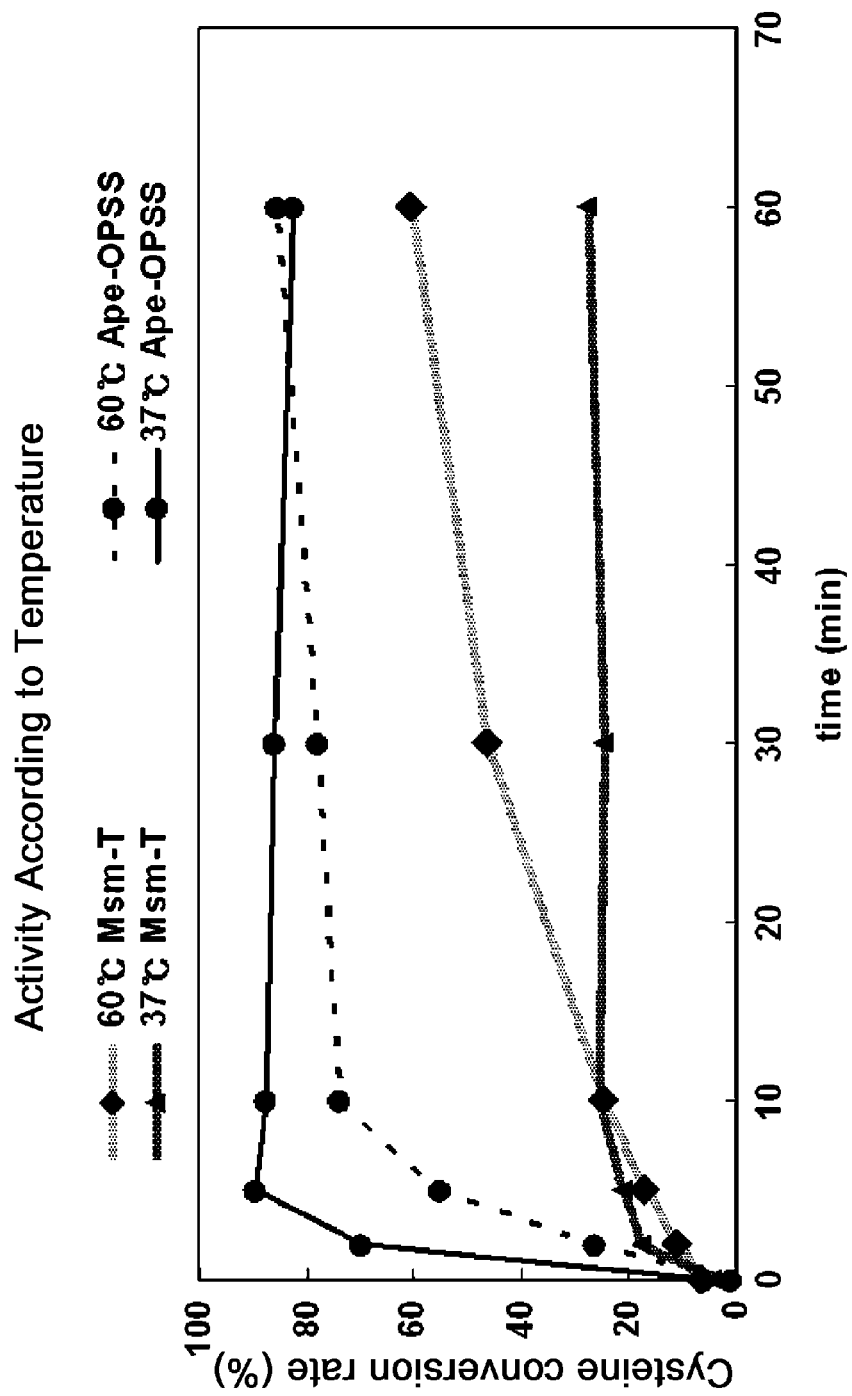
FIG. 2 is a graph showing the activity of OPS sulfhydrylase according to temperatures.

The cysteine conversion rates of Ape-OPSS and Msm-T according to temperatures were examined. The enzymatic activity at 37° C. and 60° C. was measured 2, 5, 10, 30, and 60 min after reaction. The reaction was conducted under the condition of 100 mM HEPES (pH 7.4), 5 mM OPS, 10 mM Na$_2$S, 0.2 mM PLP, and CysM 50 µg/mL. The amount of produced cysteine was determined using the Gaitonde method. In the condition of a buffer, as shown in FIG. 2, Ape-OPSS showed a faster initial reaction rate at 37° C. as well as higher reactivity at 60° C. than did Msm-T.

Example 42: Heat Stability of OPS Sulfhydrylase

Ape-OPSS and Msm-T were analyzed for heat stability. Each of the enzymes was diluted to a concentration of 2 mg/mL in an OPS broth and thermally treated at 37° C. and 60° C. for 10, 30, 60, 120, and 240 min, followed by reaction at 37° C. for 30 min under the condition of 5 mM OPS, 10 mM Na$_2$S, 0.2 mM PLP, and 100 mM HEPES (pH 7.4). For this reaction, 10 µg/mL Ape-OPSS and 50 µg/mL Msm-T were employed. The amounts of the produced cysteine were measured using the Gaitonde method. Ape-OPSS was observed to retain its intact activity in spite of heat treatment at 60° C. for 4 hours while the activity of Msm-T was maintained at 37° C., but decreased by 50% upon heat treatment at 60° C. for 30 min. The results are given in Table 31, below.

TABLE 31

|  | Relative activity (%) Heating time (min) | | | | | |
| --- | --- | --- | --- | --- | --- | --- |
|  | (—) | 10 min | 30 min | 60 min | 120 min | 240 min |
| Ape-OPSS | 100 | 102 | 107 | 100 | 107 | 101 |
| Msm-T | 100 | 82 | 50 | 32 | 19 | 8 |

An examination was made of the retention of enzymatic activity at 37° C. when Msm-T was used in an amount of 50 µg/mL, which is a practical concentration in OPS broth. In the absence of Na$_2$S, 50 µg/mL Msm-T was treated, together with 50 mM OPS broth and 0.2 mM PLP, at 37° C. for 0.5, 1, 2, 4, and 6 hours, after which Na$_2$S was added to induce the enzymatic reaction. After the reaction for 30 min, the activity of Msm-T was measured. The amounts of the produced cysteine were determined using the Gaitonde method. As a result, the activity of Msm-T was decreased below 50% 2 hours after reaction at 37° C. in OPS broth (Table 32).

TABLE 32

|  | Time | | | | | |
| --- | --- | --- | --- | --- | --- | --- |
|  | 0 | 30 min | 60 min | 120 min | 240 min | 360 min |
| Cysteine conversion rate (%) | 100 | 88 | 73 | 47 | 11 | 3 |

Example 43: The Influence of pH on the OPS Sulfhydrylase

Figure 3:
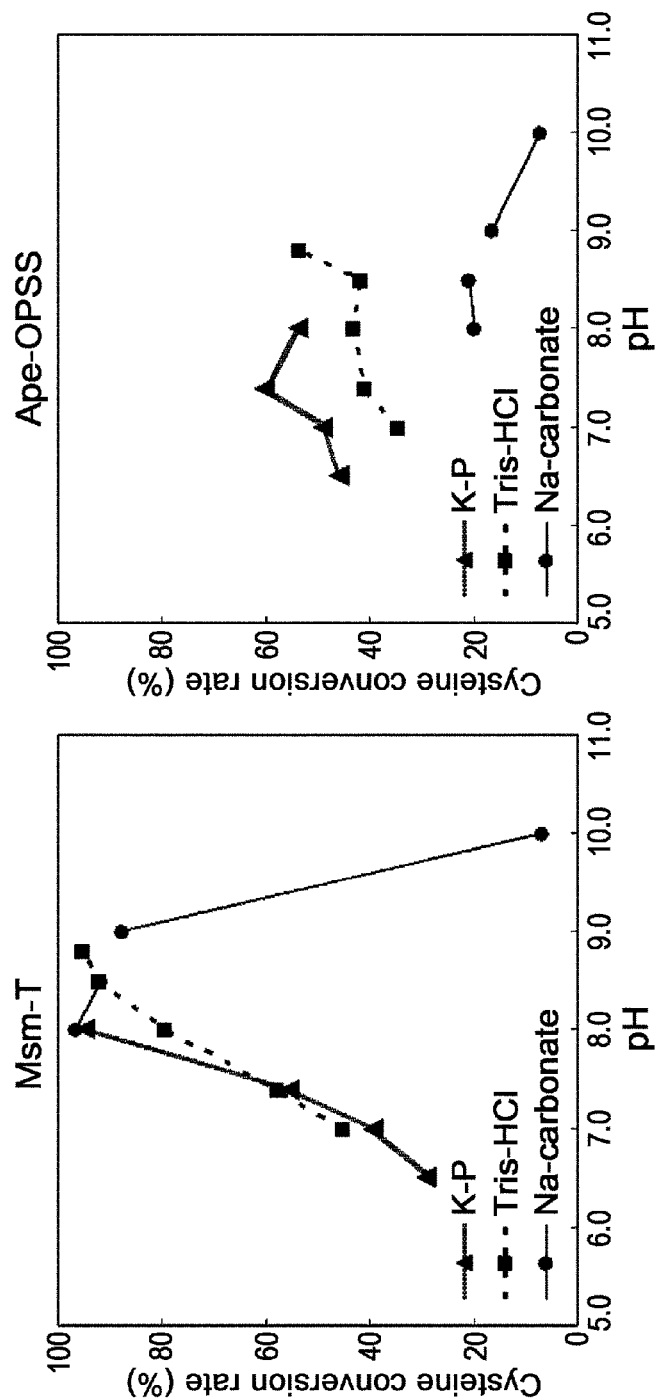
FIG. 3 is a set of graphs showing pH sensitivity of OPS sulfhydrylase.

The cysteine conversion rates of Ape-OPSS and Msm-T according to pH were measured. In 100 mM buffer, Ape-OPSS and Msm-T, each having a concentration of 50 µg/mL, were subjected to reaction at 37° C. for 10 min. In this regard, K-phosphate buffer with a pH of 6.4/7.0/7.4/8.0, Tris-HCl buffer with a pH of 7.0/7.4/8.0/8.5/8.8, and Na-carbonate buffer with a pH of 8.0/8.5/9.0/10.0 were used. The quantitative analysis of the produced cysteine was conducted using the Gaitonde method. As seen in FIG. 3, Msm-T exhibited the highest activity at a pH of from 8.0 to 9.0 irrespective of buffer. As for Ape-OPSS, its highest activity was detected in K-phosphate (pH 7.4), with an optimal pH differing from one buffer to another.

Example 44: Effect of Ions on the Activity of OPS Sulfhydrylase

Effects of ions on the activity of the OPSS enzymes were examined as follows. In a reaction mixture containing 5 mM OPS, 10 mM Na$_2$S, 0.2 mM PLP, and 100 mM HEPES (pH 7.4), the enzymes were subjected to reaction at 37° C. for 30 min in the presence of (NH$_4$)$_2$SO$_4$ (1, 3, 5, 10, 20 g/L), KH$_2$PO$_4$ (0.5, 1, 2, 4, 8 g/L), or NH$_4$Cl (0.2, 0.5, 1, 2 g/L). Ape-OPSS and Msm-T were used at a concentration of 10 µg/mL and 50 µg/mL, respectively. The amounts of the produced cysteine were determined using the Gaitonde method.

No changes were detected in the cysteine conversion rate when (NH$_4$)$_2$SO$_4$ or KH$_2$PO$_4$ was added to the reaction mixture. On the other hand, as seen in Table 33, the cysteine conversion rate was decreased with an increase in NH$_4$Cl concentration. Particularly, the maximal enzyme activity was decreased by more than 70% when 2 g/L NH$_4$Cl was added. Therefore, NH$_4$Cl was observed to have a negative effect on the conversion activity of OPS sulfhydrylase.

TABLE 33

|  | Relative activity (%) | |
| --- | --- | --- |
| NH$_4$Cl | Ape-OPSS | Msm-T |
| 0 | 100.00 | 100.00 |
| 0.2 | 86.26 | 91.49 |
| 0.5 | 73.35 | 91.30 |
| 1 | 49.11 | 67.11 |
| 2 | 27.72 | 47.12 |

Example 45: Effect of Sulfur Source on the Cysteine Synthesis Activity of OPS Sulfhydrylase An experiment was conducted to examine the effect of sulfur sources on the cysteine synthesis activity of each enzyme. In a reaction mixture containing 5 mM OPS, 0.2 mM PLP, and 100 mM HEPES, each enzyme (50 µg/mL Ape-OPSS, 50 µg/mL Msm-T) was subjected to reaction at 37° C. for 1 hour in the presence of 10 mM Na$_2$S, NaSH, or Na$_2$S$_2$O$_3$. The amounts of the produced cysteine were measured using the Gaitonde method. Ape-OPSS was observed to prefer Na$_2$S$_2$O$_3$ as a sulfur source, whereas Msm-T prefers Na$_2$S. The results are summarized in Table 34, below.

TABLE 34

|  | Relative activity (%) | | |
| --- | --- | --- | --- |
| Enzyme | Na$_2$S | NaSH | Na$_2$S$_2$O$_3$ |
| Ape-OPSS | 100.0 | 95.2 | 142.3 |
| Msm-T | 106.7 | 98.3 | 66.2 |

Example 46: Construction of the Expression Vector Carrying OPS Sulfhydrylase (pCL-Pcj1 System) and Expression in *E. Coli*

Figure 4:
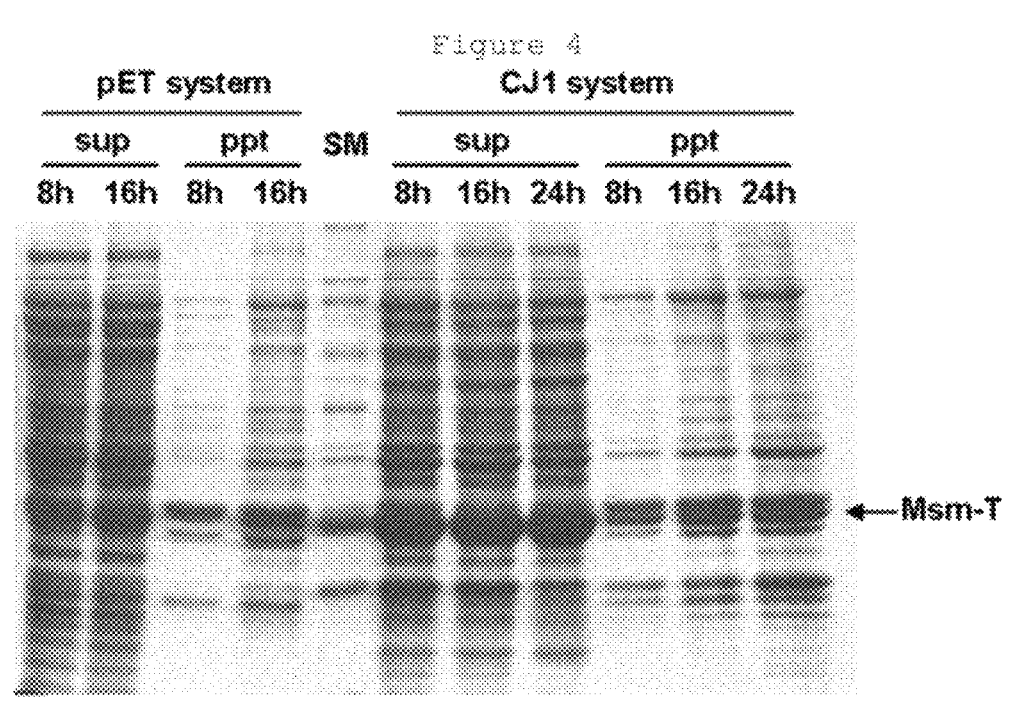

PCR was performed using primers of SEQ ID NOS: 123 and 124, with the pET28a-Msm-T vector serving as a template. The PCR product thus obtained was treated with EcoRV and HindIII and cloned into pCL-P(CJ1) to construct a recombinant vector named pCL-P(CJ1)-Msm-T. To examine a difference in the expression level of Msm-T between the pET system and the pCL-Pcj1 system, strains for expressing the enzyme were prepared. The pET system was introduced into Rosetta (DE3) while the pCL-Pcj1 system used the K12G strain. Single colonies taken from LB plates were inoculated into 5 mL of LB broth and cultured at 37° C. for 16 hours while shaking at 200 rpm. These cultures were transferred to 25 mL of fresh LB broth containing kanamycine or spectinomycine and 0.2% glucose (in 250 mL flasks) and incubated to an $OD_{600}$ of 0.5-0.6, immediately after which 1 mM IPTG was added to the media to induce the enzymes to be expressed. During incubation at 37° C. while shaking at 200 rpm, the expression levels of the enzyme were measured at various culture times (8, 16, 24 hours). The enzyme expression levels of the two systems were analyzed on 14% SDS PAGE (FIG. 4).

Example 47: Cysteine Synthesis by OPS Sulfhydrylase with the Purified OPS Fermentation Broth The conversion rates from purified OPS to cysteine of Msm-T and Ape-OPSS were determined. In the presence of 75 µg/mL of each of the enzymes and 0.2 mM PLP, 60 mM OPS purified from OPS fermentation broth was reacted with 120 mM $Na_2S$ at 37° C. or 70° C. for 30, 60, 90, and 120 min. The reaction was conducted only at 37° C. for Msm-T, but at both 37° C. and 70° C. for Ape-OPSS. The amounts of the produced cysteine were measured using the Gaitonde method. As seen in FIG. 5, a purified OPS fermentation broth served well as a substrate for the enzymatic conversion into cysteine. Particularly, the conversion rate of Ape-OPSS was increased at 70° C. even upon the use of the purified OPS fermentation broth.

Example 48: Cysteine Synthesis by Ops sulfhydrylase with the OPS Fermentation Broth When an OPS fermentation broth was used as a substrate, the cysteine conversion rates of Msm-T and Ape-OPSS were measured according to the concentrations of the enzymes. In the presence of 100 mM $Na_2S$ and 0.2 mM PLP, 50 mM of OPS fermentation broth was reacted with 5 µg/mL or 50 µg/mL of each of Msm-T and Ape-OPSS at 37° C. The amounts of the produced cysteine were measured using the Gaitonde method. As seen in FIG. 6, the highest conversion rate was detected in 50 µg/mL Msm-T. In addition, upon the use of OPS fermentation broth as a substrate, the activity of Msm-T was higher than that of Ape-OPSS.

Example 49: Cysteine Conversion Rate According to OPS Concentration

To examine the effect of OPS concentration on the conversion rate of Msm-T, predetermined amounts of purified OPS were added to OPS fermentation broth to induce the conversion reaction. The enzyme was used in an amount of 50 µg. The amounts of cysteine in the reaction solution were measured using the Gaitonde method. Msm-T exhibited a conversion rate of as high as 100% when the concentration of OPS was about 30 g/L.

When the concentration of OPS exceeded 50 g/L, both the conversion rate and the conversion percentage were found to decrease. From these results, it is understood that when OPS fermentation broth is used as a substrate, there is an optimal concentration ratio between OPS and the enzyme.

TABLE 35

Cysteine Conversion Rate (Msm-T 50 ug)

| | Time | | | | | |
| --- | --- | --- | --- | --- | --- | --- |
| | 0 min | 10 min | 30 min | 60 min | 120 min | 180 min |
| OPS measured 10.65 g/l | 0 | 23.03 | 65.38 | 65.70 | 61.95 | 55.35 |
| OPS measured 36.09 g/l | 0 | 1.15 | 10.23 | 28.07 | 97.84 | 100.34 |
| OPS measured 55.6 g/l | 0 | 0 | 2.36 | 7.41 | 42.69 | 66.67 |

The invention claimed is:

1. A method for producing cysteine or a derivative thereof, comprising:
   (a) culturing a recombinant microorganism in which the activity of an endogenous phosphoserine phosphatase (SerB) and a phosphonate transporter (PhnCDE; phnC (ATP-binding component of phosphonate transport, EG 10713)-phnD (periplasmic binding protein component of Pn transporter, EG 10714)-phnE (integral membrane component of the alkylphosphonate ABC transporter, EG 11283)) is reduced, and the activity of a phosphoglycerate dehydrogenase (SerA) is enhanced, to produce O-phosphoserine (OPS);
   wherein the level of endogenous SerB or PhnCDE activity is reduced by deletion of the endogenous SerB or PhnCDE gene
   wherein the level of SerA activity is increased by increasing copy number of the SerA gene or changing an endogenous promoter into a strong promoter, wherein the phosphoserine phosphatase comprises the amino acid sequence of SEQ ID NO: 1 or SEQ ID NO:2 and wherein the SerA having increased activity comprises the amino acid sequence selected from the group consisting of SEQ ID NOs: 3, 5, 6, and 7; and
   (b) reacting the OPS of step (a) with a sulfide in presence of O-phosphoserine sulfhydrylase (OPSS) or a microorganism expressing OPSS, to produce cysteine or derivatives thereof, wherein the OPSS comprises the amino acid sequence selected from the group consisting of SEQ ID NOs: 9, 10 and 12;
   wherein the recombinant microorganism has been further modified to
   (i) enhance the activity of a nucleotide transhydrogenase (PntAB), wherein the level of nucleotide transhydrogenase activity is enhanced by increasing the copy number of a gene encoding the nucleotide transhydrogenase or changing an endogenous promoter into a strong promoter; and/or
   (ii) enhance the activity of at least one enzyme selected from the group consisting of o-acetylserine/cysteine efflux permease (YfiK), homoserine/homoserine lactone efflux protein (RhtB), and threonine/homoserine efflux protein (RhtC), wherein the level of enzyme activity is enhanced by increasing the copy number of a gene encoding the enzyme or changing an endogenous promoter into a strong promoter.

2. The method of claim 1, wherein the recombinant microorganism is cultured in a medium containing glycine or serine.

3. The method of claim 2, wherein the medium contains glycine in an amount of from 0.1 to 10 g/L.

4. The method of claim 2, wherein the medium contains serine in an amount of from 0.1 to 5 g/L.

5. The method of claim 1, wherein the SerA is resistant to serine feedback inhibition.

6. The method of claim 1, wherein the recombinant microorganism has been further modified to enhance the activity a phosphoserine aminotransferase (SerC), wherein the level of phosphoserine aminotransferase activity is enhanced increasing the copy number of a gene encoding the phosphoserine aminotransferase or changing an endogenous promoter into a strong promoter, and wherein the SerC comprises the amino acid sequence of SEQ ID NO: 8.

7. The method of claim 1, wherein the recombinant microorganism has been further modified to reduce the activity of an alkaline phosphatase (PhoA) or an acid phosphatase (AphA), wherein the level of enzyme activity is reduced by deletion of the endogenous gene.

8. The method of claim 1, wherein the recombinant microorganism has been further modified to reduce the activity of at least one endogenous phosphoglycerate mutase isozyme selected from the group consisting of GpmA, GpmI and GpmB, wherein said activity is reduced by deletion of at least one endogenous gene encoding the at least one phosphoglycerate mutase isozyme.

9. The method of claim 1, wherein the recombinant microorganism has been further modified to reduce the activity of an L-serine dehydratase I (SdaA), wherein said activity is reduced by deletion of the endogenous gene encoding the L-serine dehydratase I.

10. The method of claim 1, wherein the recombinant microorganism has been further modified to reduce the activity of a 2-amino-3-ketobutyrate coenzyme A ligase (Kbl) or a transcription factor (IClR), wherein said activity is reduced by deletion of the endogenous gene encoding the 2-amino-3-ketobutyrate coenzyme A ligase or by deletion of the endogenous gene encoding the transcription factor.

11. The method of claim 1, wherein the recombinant microorganism has been further modified to enhance the activity of at least one enzyme selected from the group consisting of acetyl-CoA synthetase (Acs), acetic acid kinase (AckA), phosphotransacetylase (Pta), malate synthase G (GlcB), malate dehydrogenase (MaeB), glutamate dehydrogenase (GdhA), glyoxylate carboligase (Glc), tartronate semialdehyde reductase 2 (GlxR) and glycerate kinase II (GlxK), wherein the level of enzyme activity is enhanced by increasing the copy number of a gene encoding the enzyme or changing an endogenous promoter into a strong promoter.

12. The method of claim 11, wherein the recombinant microorganism is improved in sugar consumption and growth by enhancement of the activity of at least one enzyme selected from the group consisting of glyoxylate carboligase (Glc), tartronate semialdehyde reductase 2 (GlxR), and a glycerate kinase II (GlxK), wherein the level of enzyme activity is enhanced by increasing the copy number of a gene encoding the enzyme or changing an endogenous promoter into a strong promoter.

13. The method of claim 1, wherein the recombinant microorganism is *Escherichia* sp. or *Coryneform* bacteria.

14. The method of claim 1, wherein the sulfide of step (b) is selected from the group consisting of $Na_2S$, NaSH, $(NH_4)_2S$, $H_2S$, $Na_2S_2O_3$ and a combination thereof.

15. The method of claim 1, wherein the sulfide of step (b) is used at a molar concentration 0.1 to 3 times higher than that of OPS used in the enzymatic reaction.

16. The method of claim 1, wherein the reaction of step (b) is carried out in presence of a cofactor selected from the group consisting of PLP (pyridoxal-5-phosphate), DTT (dithiothreitol), and a combination thereof, wherein the concentration of PLP in the reaction is 0.001 to 2 mM and the concentration of DTT in the reaction is 0.001 to 100 mM.

17. The method of claim 1, further comprising isolating and purifying the cysteine or its derivative.

* * * * *

SEQUENCE LISTING

```
<160> NUMBER OF SEQ ID NOS: 124

<210> SEQ ID NO 1
<211> LENGTH: 446
<212> TYPE: PRT
<213> ORGANISM: Corynebacterium glutamicum 13032
<220> FEATURE:
<221> NAME/KEY: PEPTIDE
<222> LOCATION: (1)..(446)
<223> OTHER INFORMATION: phosphoserine phosphatase, SerB

<400> SEQUENCE: 1

Met Ser Cys Ser Ala Leu Arg His Glu Thr Ile Val Ala Val Thr Glu
  1               5                  10                  15

Leu Ile Gln Asn Glu Ser Gln Glu Ile Ala Glu Leu Glu Ala Gly Gln
             20                  25                  30

Gln Val Ala Leu Arg Glu Gly Tyr Leu Pro Ala Val Ile Thr Val Ser
         35                  40                  45

Gly Lys Asp Arg Pro Gly Val Thr Ala Ala Phe Phe Arg Val Leu Ser
     50                  55                  60
```

```
Ala Asn Gln Val Gln Val Leu Asp Val Glu Gln Ser Met Phe Arg Gly
 65                  70                  75                  80

Phe Leu Asn Leu Ala Ala Phe Val Gly Ile Ala Pro Glu Arg Val Glu
                 85                  90                  95

Thr Val Thr Thr Gly Leu Thr Asp Thr Leu Lys Val His Gly Gln Ser
            100                 105                 110

Val Val Val Glu Leu Gln Glu Thr Val Gln Ser Ser Arg Pro Arg Ser
        115                 120                 125

Ser His Val Val Val Leu Gly Asp Pro Val Asp Ala Leu Asp Ile
    130                 135                 140

Ser Arg Ile Gly Gln Thr Leu Ala Asp Tyr Asp Ala Asn Ile Asp Thr
145                 150                 155                 160

Ile Arg Gly Ile Ser Asp Tyr Pro Val Thr Gly Leu Glu Leu Lys Val
                165                 170                 175

Thr Val Pro Asp Val Ser Pro Gly Gly Glu Ala Met Arg Lys Ala
            180                 185                 190

Leu Ala Ala Leu Thr Ser Glu Leu Asn Val Asp Ile Ala Ile Glu Arg
        195                 200                 205

Ser Gly Leu Leu Arg Arg Ser Lys Arg Leu Val Cys Phe Asp Cys Asp
    210                 215                 220

Ser Thr Leu Ile Thr Gly Glu Val Ile Glu Met Leu Ala Ala His Ala
225                 230                 235                 240

Gly Lys Glu Ala Glu Val Ala Ala Val Thr Glu Arg Ala Met Arg Gly
                245                 250                 255

Glu Leu Asp Phe Glu Glu Ser Leu Arg Glu Arg Val Lys Ala Leu Ala
            260                 265                 270

Gly Leu Asp Ala Ser Val Ile Asp Glu Val Ala Ala Ile Glu Leu
        275                 280                 285

Thr Pro Gly Ala Arg Thr Thr Ile Arg Thr Leu Asn Arg Met Gly Tyr
    290                 295                 300

Gln Thr Ala Val Val Ser Gly Gly Phe Ile Gln Val Leu Glu Gly Leu
305                 310                 315                 320

Ala Glu Glu Leu Glu Leu Asp Tyr Val Arg Ala Asn Thr Leu Glu Ile
                325                 330                 335

Val Asp Gly Lys Leu Thr Gly Asn Val Thr Gly Lys Ile Val Asp Arg
            340                 345                 350

Ala Ala Lys Ala Glu Phe Leu Arg Glu Phe Ala Ala Asp Ser Gly Leu
        355                 360                 365

Lys Met Tyr Gln Thr Val Ala Val Gly Asp Gly Ala Asn Asp Ile Asp
    370                 375                 380

Met Leu Ser Ala Ala Gly Leu Gly Val Ala Phe Asn Ala Lys Pro Ala
385                 390                 395                 400

Leu Lys Glu Ile Ala Asp Thr Ser Val Asn His Pro Phe Leu Asp Glu
                405                 410                 415

Val Leu His Ile Met Gly Ile Ser Arg Asp Glu Ile Leu Ala Asp
            420                 425                 430

Gln Glu Asp Gly Thr Phe His Arg Val Pro Leu Thr Asn Ala
        435                 440                 445

<210> SEQ ID NO 2
<211> LENGTH: 322
<212> TYPE: PRT
<213> ORGANISM: Escherichia coli K12 W3110
<220> FEATURE:
<221> NAME/KEY: PEPTIDE
```

<222> LOCATION: (1)..(322)
<223> OTHER INFORMATION: phosphoserine phosphatase, SerB

<400> SEQUENCE: 2

```
Met Pro Asn Ile Thr Trp Cys Asp Leu Pro Glu Asp Val Ser Leu Trp
 1               5                  10                  15

Pro Gly Leu Pro Leu Ser Leu Ser Gly Asp Glu Val Met Pro Leu Asp
            20                  25                  30

Tyr His Ala Gly Arg Ser Gly Trp Leu Leu Tyr Gly Arg Gly Leu Asp
        35                  40                  45

Lys Gln Arg Leu Thr Gln Tyr Gln Ser Lys Leu Gly Ala Ala Met Val
    50                  55                  60

Ile Val Ala Ala Trp Cys Val Glu Asp Tyr Gln Val Ile Arg Leu Ala
65                  70                  75                  80

Gly Ser Leu Thr Ala Arg Ala Thr Arg Leu Ala His Glu Ala Gln Leu
                85                  90                  95

Asp Val Ala Pro Leu Gly Lys Ile Pro His Leu Arg Thr Pro Gly Leu
            100                 105                 110

Leu Val Met Asp Met Asp Ser Thr Ala Ile Gln Ile Glu Cys Ile Asp
        115                 120                 125

Glu Ile Ala Lys Leu Ala Gly Thr Gly Glu Met Val Ala Glu Val Thr
    130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175

Arg Glu Asn Leu Pro Leu Met Pro Gly Leu Thr Gln Leu Val Leu Lys
            180                 185                 190

Leu Glu Thr Leu Gly Trp Lys Val Ala Ile Ala Ser Gly Gly Phe Thr
        195                 200                 205

Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
        275                 280                 285

Tyr His Ala Lys Pro Lys Val Asn Glu Lys Ala Glu Val Thr Ile Arg
    290                 295                 300

His Ala Asp Leu Met Gly Val Phe Cys Ile Leu Ser Gly Ser Leu Asn
305                 310                 315                 320

Gln Lys
```

<210> SEQ ID NO 3
<211> LENGTH: 530
<212> TYPE: PRT
<213> ORGANISM: Artificial Sequence
<220> FEATURE:
<223> OTHER INFORMATION: D-3-phosphoglycerate dehydrogenase(E235K),
    SerA(E235K)

<400> SEQUENCE: 3

Met Ser Gln Asn Gly Arg Pro Val Val Leu Ile Ala Asp Lys Leu Ala

-continued

```
  1               5                  10                 15
Gln Ser Thr Val Asp Ala Leu Gly Asp Ala Val Glu Val Arg Trp Val
             20                 25                 30
Asp Gly Pro Asn Arg Pro Glu Leu Leu Asp Ala Val Lys Glu Ala Asp
             35                 40                 45
Ala Leu Leu Val Arg Ser Ala Thr Thr Val Asp Ala Glu Val Ile Ala
 50                 55                 60
Ala Ala Pro Asn Leu Lys Ile Val Gly Arg Ala Gly Val Gly Leu Asp
 65                 70                 75                 80
Asn Val Asp Ile Pro Ala Ala Thr Glu Ala Gly Val Met Val Ala Asn
                 85                 90                 95
Ala Pro Thr Ser Asn Ile His Ser Ala Cys Glu His Ala Ile Ser Leu
             100                105                110
Leu Leu Ser Thr Ala Arg Gln Ile Pro Ala Ala Asp Ala Thr Leu Arg
             115                120                125
Glu Gly Glu Trp Lys Arg Ser Ser Phe Asn Gly Val Glu Ile Phe Gly
             130                135                140
Lys Thr Val Gly Ile Val Gly Phe Gly His Ile Gly Gln Leu Phe Ala
145                150                155                160
Gln Arg Leu Ala Ala Phe Glu Thr Thr Ile Val Ala Tyr Asp Pro Tyr
                 165                170                175
Ala Asn Pro Ala Arg Ala Ala Gln Leu Asn Val Glu Leu Val Glu Leu
             180                185                190
Asp Glu Leu Met Ser Arg Ser Asp Phe Val Thr Ile His Leu Pro Lys
             195                200                205
Thr Lys Glu Thr Ala Gly Met Phe Asp Ala Gln Leu Leu Ala Lys Ser
210                215                220
Lys Lys Gly Gln Ile Ile Asn Ala Ala Arg Gly Gly Leu Val Asp
225                230                235                240
Glu Gln Ala Leu Ala Asp Ala Ile Glu Ser Gly His Ile Arg Gly Ala
             245                250                255
Gly Phe Asp Val Tyr Ser Thr Glu Pro Cys Thr Asp Ser Pro Leu Phe
             260                265                270
Lys Leu Pro Gln Val Val Thr Pro His Leu Gly Ala Ser Thr Glu
             275                280                285
Glu Ala Gln Asp Arg Ala Gly Thr Asp Val Ala Asp Ser Val Leu Lys
             290                295                300
Ala Leu Ala Gly Glu Phe Val Ala Asp Ala Val Asn Val Ser Gly Gly
305                310                315                320
Arg Val Gly Glu Lys Val Ala Val Trp Met Asp Leu Ala Arg Lys Leu
                 325                330                335
Gly Leu Leu Ala Gly Lys Leu Val Asp Ala Ala Pro Val Ser Ile Glu
             340                345                350
Val Glu Ala Arg Gly Glu Leu Ser Ser Glu Gln Val Asp Ala Leu Gly
             355                360                365
Leu Ser Ala Val Arg Gly Leu Phe Ser Gly Ile Ile Glu Glu Ser Val
             370                375                380
Thr Phe Val Asn Ala Pro Arg Ile Ala Glu Glu Arg Gly Leu Asp Ile
385                390                395                400
Ser Val Lys Thr Asn Ser Glu Ser Val Thr His Arg Ser Val Leu Gln
             405                410                415
Val Lys Val Ile Thr Gly Ser Gly Ala Ser Ala Thr Val Val Gly Ala
             420                425                430
```

```
Leu Thr Gly Leu Glu Arg Val Glu Lys Ile Thr Arg Ile Asn Gly Arg
        435                 440                 445

Gly Leu Asp Leu Arg Ala Glu Gly Leu Asn Leu Phe Leu Gln Tyr Thr
    450                 455                 460

Asp Ala Pro Gly Ala Leu Gly Thr Val Gly Thr Lys Leu Gly Ala Ala
465                 470                 475                 480

Gly Ile Asn Ile Glu Ala Ala Ala Leu Thr Gln Ala Glu Lys Gly Asp
                485                 490                 495

Gly Ala Val Leu Ile Leu Arg Val Glu Ser Ala Val Ser Glu Glu Leu
                500                 505                 510

Glu Ala Glu Ile Asn Ala Glu Leu Gly Ala Thr Ser Phe Gln Val Asp
        515                 520                 525

Leu Asp
    530

<210> SEQ ID NO 4
<211> LENGTH: 333
<212> TYPE: PRT
<213> ORGANISM: Artificial Sequence
<220> FEATURE:
<223> OTHER INFORMATION: D-3-phosphoglycerate dehydrogenase(197 delta),
      SerA(197 delta)

<400> SEQUENCE: 4

Met Ser Gln Asn Gly Arg Pro Val Val Leu Ile Ala Asp Lys Leu Ala
  1               5                  10                  15

Gln Ser Thr Val Asp Ala Leu Gly Asp Ala Val Glu Val Arg Trp Val
                 20                  25                  30

Asp Gly Pro Asn Arg Pro Glu Leu Leu Asp Ala Val Lys Glu Ala Asp
             35                  40                  45

Ala Leu Leu Val Arg Ser Ala Thr Thr Val Asp Ala Glu Val Ile Ala
     50                  55                  60

Ala Ala Pro Asn Leu Lys Ile Val Gly Arg Ala Gly Val Gly Leu Asp
 65                  70                  75                  80

Asn Val Asp Ile Pro Ala Ala Thr Glu Ala Gly Val Met Val Ala Asn
                 85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
```

```
                            245                 250                 255
Gly Phe Asp Val Tyr Ser Thr Glu Pro Cys Thr Asp Ser Pro Leu Phe
                260                 265                 270

Lys Leu Pro Gln Val Val Thr Pro His Leu Gly Ala Ser Thr Glu
            275                 280                 285

Glu Ala Gln Asp Arg Ala Gly Thr Asp Val Ala Asp Ser Val Leu Lys
        290                 295                 300

Ala Leu Ala Gly Glu Phe Val Asp Ala Val Asn Val Ser Gly Gly
305                 310                 315                 320

Arg Val Gly Glu Glu Val Ala Val Trp Met Asp Leu Ala
                325                 330

<210> SEQ ID NO 5
<211> LENGTH: 410
<212> TYPE: PRT
<213> ORGANISM: Artificial Sequence
<220> FEATURE:
<223> OTHER INFORMATION: D-3-phosphoglycerate dehydrogenase(G336V),
      SerA(G336V)

<400> SEQUENCE: 5

Met Ala Lys Val Ser Leu Glu Lys Asp Lys Ile Lys Phe Leu Leu Val
  1               5                  10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270
```

```
Asn Ser Asp Pro Phe Thr Ser Pro Leu Cys Glu Phe Asp Asn Val Leu
            275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Gly Arg Arg Leu Met His Ile His Glu Asn Arg Pro Gly Val Leu Thr
                340                 345                 350

Ala Leu Asn Lys Ile Phe Ala Glu Gln Gly Val Asn Ile Ala Ala Gln
            355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 6
<211> LENGTH: 410
<212> TYPE: PRT
<213> ORGANISM: Artificial Sequence
<220> FEATURE:
<223> OTHER INFORMATION: D-3-phosphoglycerate dehydrogenase(G336V,
      G337V), SerA(G336V, G337V)

<400> SEQUENCE: 6

Met Ala Lys Val Ser Leu Glu Lys Asp Lys Ile Lys Phe Leu Leu Val
  1               5                  10                  15

Glu Gly Val His Gln Lys Ala Leu Glu Ser Leu Arg Ala Ala Gly Tyr
                20                  25                  30

Thr Asn Ile Glu Phe His Lys Gly Ala Leu Asp Asp Glu Gln Leu Lys
            35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
 65                  70                  75                  80

Cys Phe Cys Ile Gly Thr Asn Gln Val Asp Leu Asp Ala Ala Ala Lys
                 85                  90                  95

Arg Gly Ile Pro Val Phe Asn Ala Pro Phe Ser Asn Thr Arg Ser Val
                100                 105                 110

Ala Glu Leu Val Ile Gly Glu Leu Leu Leu Leu Leu Arg Gly Val Pro
            115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
                180                 185                 190

Gln Val Gln His Leu Ser Asp Leu Leu Asn Met Ser Asp Val Val Ser
            195                 200                 205

Leu His Val Pro Glu Asn Pro Ser Thr Lys Asn Met Met Gly Ala Lys
    210                 215                 220
```

```
Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Val Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 7
<211> LENGTH: 410
<212> TYPE: PRT
<213> ORGANISM: Artificial Sequence
<220> FEATURE:
<223> OTHER INFORMATION: D-3-phosphoglycerate dehydrogenase(G336V,
      R338G), SerA(G336V, R338G)

<400> SEQUENCE: 7

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
                20                  25                  30

Thr Asn Ile Glu Phe His Lys Gly Ala Leu Asp Asp Glu Gln Leu Lys
            35                  40                  45

Glu Ser Ile Arg Asp Ala His Phe Ile Gly Leu Arg Ser Arg Thr His
        50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
```

```
                165                 170                 175
Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Gly Gly Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 8
<211> LENGTH: 362
<212> TYPE: PRT
<213> ORGANISM: Escherichia coli K12 W3110
<220> FEATURE:
<221> NAME/KEY: PEPTIDE
<222> LOCATION: (1)..(362)
<223> OTHER INFORMATION: 3-phosphoserine/phosphohydroxythreonine
      aminotransferase, SerC

<400> SEQUENCE: 8

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
```

```
                    100                 105                 110
Tyr Cys Thr Pro Asn Val Phe Asp Ala Lys Val Thr Val Asp Gly Leu
            115                 120                 125

Arg Ala Val Lys Pro Met Arg Glu Trp Gln Leu Ser Asp Asn Ala Ala
130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
            195                 200                 205

Ile Val Arg Glu Asp Leu Leu Gly Lys Ala Asn Ile Ala Cys Pro Ser
            210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
                260                 265                 270

Ala Glu Leu Leu Tyr Gly Val Ile Asp Asn Ser Asp Phe Tyr Arg Asn
            275                 280                 285

Asp Val Ala Lys Ala Asn Arg Ser Arg Met Asn Val Pro Phe Gln Leu
            290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
            355                 360

<210> SEQ ID NO 9
<211> LENGTH: 323
<212> TYPE: PRT
<213> ORGANISM: Mycobacterium smegmatics str. MC2 155
<220> FEATURE:
<221> NAME/KEY: PEPTIDE
<222> LOCATION: (1)..(323)
<223> OTHER INFORMATION: Msm-OPSS

<400> SEQUENCE: 9

Met Thr Arg Tyr Asp Ser Leu Leu Gln Ala Leu Gly Asn Thr Pro Leu
1               5                   10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
    50                  55                  60

Asp Gly Leu Leu Gln Pro Gly Ala Thr Ile Leu Glu Pro Thr Ser Gly
65                  70                  75                  80

Asn Thr Gly Ile Ser Leu Ala Met Ala Ala Leu Leu Lys Gly Tyr Asn
                85                  90                  95
```

```
Met Ile Cys Val Met Pro Glu Asn Thr Ser Ile Glu Arg Arg Gln Ile
                100                 105                 110

Leu Glu Leu Tyr Gly Ala Arg Ile Ile Phe Ser Pro Ala Glu Gly Gly
            115                 120                 125

Ser Asn Thr Ala Val Ala Thr Ala Lys Glu Leu Ala Ala Gln Asn Pro
        130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
            180                 185                 190

Gly Arg Phe Leu Arg Glu His Val Pro Gly Val Gln Ile Val Ala Ala
        195                 200                 205

Glu Pro Arg Tyr Gly Glu Gly Val Tyr Ala Leu Arg Asn Ile Asp Glu
210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
            260                 265                 270

Ala Leu Gly Met Ala Ala Lys Ala Val Lys Ala Gly Glu Arg Ala Asp
        275                 280                 285

Ile Ala Phe Val Val Ala Asp Ala Gly Trp Lys Tyr Leu Ser Thr Gly
    290                 295                 300

Ala Tyr Ala Gly Ser Leu Asp Asp Ala Glu Asp Ala Leu Glu Gly Gln
305                 310                 315                 320

Leu Trp Ala

<210> SEQ ID NO 10
<211> LENGTH: 318
<212> TYPE: PRT
<213> ORGANISM: Mycobacterium smegmatics str. MC2 155
<220> FEATURE:
<221> NAME/KEY: PEPTIDE
<222> LOCATION: (1)..(318)
<223> OTHER INFORMATION: Msm-T

<400> SEQUENCE: 10

Met Thr Arg Tyr Asp Ser Leu Leu Gln Ala Leu Gly Asn Thr Pro Leu
1               5                   10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
    50                  55                  60

Asp Gly Leu Leu Gln Pro Gly Ala Thr Ile Leu Glu Pro Thr Ser Gly
65                  70                  75                  80

Asn Thr Gly Ile Ser Leu Ala Met Ala Leu Leu Lys Gly Tyr Asn
                85                  90                  95

Met Ile Cys Val Met Pro Glu Asn Thr Ser Ile Glu Arg Arg Gln Ile
                100                 105                 110

Leu Glu Leu Tyr Gly Ala Arg Ile Ile Phe Ser Pro Ala Glu Gly Gly
            115                 120                 125
```

```
            115                 120                 125
Ser Asn Thr Ala Val Ala Thr Ala Lys Glu Leu Ala Ala Gln Asn Pro
130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
                180                 185                 190

Gly Arg Phe Leu Arg Glu His Val Pro Gly Val Gln Ile Val Ala Ala
            195                 200                 205

Glu Pro Arg Tyr Gly Glu Gly Val Tyr Ala Leu Arg Asn Ile Asp Glu
        210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
                260                 265                 270

Ala Leu Gly Met Ala Ala Lys Ala Val Lys Ala Gly Glu Arg Ala Asp
            275                 280                 285

Ile Ala Phe Val Val Ala Asp Ala Gly Trp Lys Tyr Leu Ser Thr Gly
        290                 295                 300

Ala Tyr Ala Gly Ser Leu Asp Asp Ala Glu Asp Ala Leu Glu
305                 310                 315

<210> SEQ ID NO 11
<211> LENGTH: 318
<212> TYPE: PRT
<213> ORGANISM: Mycobacterium tuberculosis H37Rv
<220> FEATURE:
<221> NAME/KEY: PEPTIDE
<222> LOCATION: (1)..(318)
<223> OTHER INFORMATION: Mtb-T

<400> SEQUENCE: 11

Met Thr Arg Tyr Asp Ser Leu Leu Gln Ala Leu Gly Asn Thr Pro Leu
  1               5                  10                  15

Val Gly Leu Gln Arg Leu Ser Pro Arg Trp Asp Asp Gly Arg Asp Gly
                20                  25                  30

Pro His Val Arg Leu Trp Ala Lys Leu Glu Asp Arg Asn Pro Thr Gly
            35                  40                  45

Ser Ile Lys Asp Arg Pro Ala Val Arg Met Ile Glu Gln Ala Glu Ala
        50                  55                  60

Asp Gly Leu Leu Arg Pro Gly Ala Thr Ile Leu Glu Pro Thr Ser Gly
65                  70                  75                  80

Asn Thr Gly Ile Ser Leu Ala Met Ala Ala Arg Leu Lys Gly Tyr Arg
                85                  90                  95

Leu Ile Cys Val Met Pro Glu Asn Thr Ser Val Glu Arg Arg Gln Leu
            100                 105                 110

Leu Glu Leu Tyr Gly Ala Gln Ile Ile Phe Ser Ala Ala Glu Gly Gly
        115                 120                 125

Ser Asn Thr Ala Val Ala Thr Ala Lys Glu Leu Ala Ala Thr Asn Pro
130                 135                 140

Ser Trp Val Met Leu Tyr Gln Tyr Gly Asn Pro Ala Asn Thr Asp Ser
145                 150                 155                 160
```

His Tyr Cys Gly Thr Gly Pro Glu Leu Leu Ala Asp Leu Pro Glu Ile
            165                 170                 175

Thr His Phe Val Ala Gly Leu Gly Thr Thr Gly Thr Leu Met Gly Thr
        180                 185                 190

Gly Arg Phe Leu Arg Glu His Val Ala Asn Val Lys Ile Val Ala Ala
    195                 200                 205

Glu Pro Arg Tyr Gly Glu Gly Val Tyr Ala Leu Arg Asn Met Asp Glu
210                 215                 220

Gly Phe Val Pro Glu Leu Tyr Asp Pro Glu Ile Leu Thr Ala Arg Tyr
225                 230                 235                 240

Ser Val Gly Ala Val Asp Ala Val Arg Arg Thr Arg Glu Leu Val His
            245                 250                 255

Thr Glu Gly Ile Phe Ala Gly Ile Ser Thr Gly Ala Val Leu His Ala
        260                 265                 270

Ala Leu Gly Val Gly Ala Gly Leu Ala Ala Gly Glu Arg Ala Asp
    275                 280                 285

Ile Ala Leu Val Val Ala Asp Ala Gly Trp Lys Tyr Leu Ser Thr Gly
290                 295                 300

Ala Tyr Ala Gly Ser Leu Asp Asp Ala Glu Thr Ala Leu Glu
305                 310                 315

<210> SEQ ID NO 12
<211> LENGTH: 389
<212> TYPE: PRT
<213> ORGANISM: Artificial Sequence
<220> FEATURE:
<223> OTHER INFORMATION: Ape-OPSS

<400> SEQUENCE: 12

Met Ala Leu Ala Asp Ile Ser Gly Tyr Leu Asp Val Leu Asp Ser Val
 1               5                  10                  15

Arg Gly Phe Ser Tyr Leu Glu Asn Ala Arg Glu Val Leu Arg Ser Gly
            20                  25                  30

Glu Ala Arg Cys Leu Gly Asn Pro Arg Ser Glu Pro Glu Tyr Val Lys
        35                  40                  45

Ala Leu Tyr Val Ile Gly Ala Ser Arg Ile Pro Val Gly Asp Gly Cys
    50                  55                  60

Ser His Thr Leu Glu Glu Leu Gly Val Phe Asp Ile Ser Val Pro Gly
65                  70                  75                  80

Glu Met Val Phe Pro Ser Pro Leu Asp Phe Phe Glu Arg Gly Lys Pro
            85                  90                  95

Thr Pro Leu Val Arg Ser Arg Leu Gln Leu Pro Asn Gly Val Arg Val
        100                 105                 110

Trp Leu Lys Leu Glu Trp Tyr Asn Pro Phe Ser Leu Ser Val Lys Asp
    115                 120                 125

Arg Pro Ala Val Glu Ile Ile Ser Arg Leu Ser Arg Arg Val Glu Lys
130                 135                 140

Gly Ser Leu Val Ala Asp Ala Thr Ser Ser Asn Phe Gly Val Ala Leu
145                 150                 155                 160

Ser Ala Val Ala Arg Leu Tyr Gly Tyr Arg Ala Arg Val Tyr Leu Pro
            165                 170                 175

Gly Ala Ala Glu Glu Phe Gly Lys Leu Leu Pro Arg Leu Leu Gly Ala
        180                 185                 190

Gln Val Ile Val Asp Pro Glu Ala Pro Ser Thr Val His Leu Leu Pro
    195                 200                 205

```
Arg Val Met Lys Asp Ser Lys Asn Glu Gly Phe Val His Val Asn Gln
210                 215                 220

Phe Tyr Asn Asp Ala Asn Phe Glu Ala His Met Arg Gly Thr Ala Arg
225                 230                 235                 240

Glu Ile Phe Val Gln Ser Arg Arg Gly Gly Leu Ala Leu Arg Gly Val
            245                 250                 255

Ala Gly Ser Leu Gly Thr Ser Gly His Met Ser Ala Ala Ala Phe Tyr
            260                 265                 270

Leu Gln Ser Val Asp Pro Ser Ile Arg Ala Val Leu Val Gln Pro Ala
        275                 280                 285

Gln Gly Asp Ser Ile Pro Gly Ile Arg Arg Val Glu Thr Gly Met Leu
    290                 295                 300

Trp Ile Asn Met Leu Asp Ile Ser Tyr Thr Leu Ala Glu Val Thr Leu
305                 310                 315                 320

Glu Glu Ala Met Glu Ala Val Val Gly Val Ala Arg Ser Asp Gly Leu
                325                 330                 335

Val Ile Gly Pro Ser Gly Gly Ala Val Lys Ala Leu Ala Lys Lys
            340                 345                 350

Ala Ala Glu Gly Asp Leu Glu Pro Gly Asp Tyr Val Val Val Pro
        355                 360                 365

Asp Thr Gly Phe Lys Tyr Leu Ser Leu Val Gln Asn Ala Leu Glu Gly
    370                 375                 380

Ala Gly Asp Ser Val
385
```

<210> SEQ ID NO 13
<211> LENGTH: 1341
<212> TYPE: DNA
<213> ORGANISM: Corynebacterium glutamicum 13032
<220> FEATURE:
<221> NAME/KEY: gene
<222> LOCATION: (1)..(1341)
<223> OTHER INFORMATION: serB

<400> SEQUENCE: 13

```
atgtcgtgtt ccgcgctcag acatgagaca attgttgccg tgactgaact catccagaat     60
gaatcccaag aaatcgctga gctggaagcc ggccagcagg ttgcattgcg tgaaggttat    120
cttcctgcgg tgatcacagt gagcggtaaa gaccgcccag gtgtgactgc cgcgttcttt    180
agggtcttgt ccgctaatca ggttcaggtc ttggacgttg agcagtcaat gttccgtggc    240
tttttgaact tggcggcgtt tgtgggtatc gcacctgagc gtgtcgagac cgtcaccaca    300
ggcctgactg acaccctcaa ggtgcatgga cagtccgtgg tggtggagct gcaggaaact    360
gtgcagtcgt cccgtcctcg ttcttcccat gttgttgtgg tgttgggtga tccggttgat    420
gcgttggata tttcccgcat tggtcagacc ctggcggatt acgatgccaa cattgacacc    480
attcgtggta tttcggatta ccctgtgacc ggcctggagc tgaaggtgac tgtgccggat    540
gtcagccctg gtggtggtga agcgatgcgt aaggcgcttg ctgctcttac ctctgagctg    600
aatgtggata ttgcgattga gcgttctggt tgctgcgtc gttctaagcg tctggtgtgc    660
ttcgattgtg attccacgtt gatcactggt gaggtcattg agatgctggc ggctcacgcg    720
ggcaaggaag ctgaagttgc ggcagttact gagcgtgcga tgcgcggtga gctcgatttc    780
gaggagtctc tgcgtgagcg tgtgaaggcg ttggctggtt tggatgcgtc ggtgatcgat    840
gaggtcgctg ccgctattga gctgaccccct ggtgcgcgca ccacgatccg tacgctgaac    900
```

```
cgcatgggtt accagaccgc tgttgtttcc ggtggtttca tccaggtgtt ggaaggtttg      960
gctgaggagt tggagttgga ttatgtccgc gccaacactt tggaaatcgt tgatggcaag     1020
ctgaccggca acgtcaccgg aaagatcgtt gaccgcgctg cgaaggctga gttcctccgt     1080
gagttcgctg cggattctgg cctgaagatg taccagactg tcgctgtcgg tgatggcgct     1140
aatgacatcg atatgctctc cgctgcgggt ctgggtgttg ctttcaacgc gaagcctgcg     1200
ctgaaggaga ttgcggatac ttccgtgaac cacccattcc tcgacgaggt tttgcacatc     1260
atgggcattt cccgcgacga gatcgatctg gcggatcagg aagacggcac ttttccaccgc    1320 gttccattga ccaatgccta a                                                1341
```

<210> SEQ ID NO 14
<211> LENGTH: 1593
<212> TYPE: DNA
<213> ORGANISM: Artificial Sequence
<220> FEATURE:
<223> OTHER INFORMATION: serA*(E235K)

<400> SEQUENCE: 14

```
atgagccaga atggccgtcc ggtagtcctc atcgccgata agcttgcgca gtccactgtt       60
gacgcgcttg gagatgcagt agaagtccgt tgggttgacg gacctaaccg cccagaactg      120
cttgatgcag ttaaggaagc ggacgcactg ctcgtgcgtt ctgctaccac tgtcgatgct      180
gaagtcatcg ccgctgcccc taacttgaag atcgtcggtc gtgccggcgt gggcttggac      240
aacgttgaca tccctgctgc cactgaagct ggcgtcatgg ttgctaacgc accgacctct      300
aatattcact ccgcttgtga gcacgcaatt tctttgctgc tgtctactgc tcgccagatc      360
cctgctgctg atgcgacgct gcgtgagggc gagtggaagc ggtcttcttt caacggtgtg      420
gaaattttcg gaaaaactgt cggtatcgtc ggttttggcc acattggtca gttgtttgct      480
cagcgtcttg ctgcgtttga gaccaccatt gttgcttacg atccttacgc taaccctgct      540
cgtgcggctc agctgaacgt tgagttggtt gagttggatg agctgatgag ccgttctgac      600
tttgtcacca ttcaccttcc taagaccaag gaaactgctg gcatgtttga tgcgcagctc      660
cttgctaagt ccaagaaggg ccagatcatc atcaacgctg ctcgtggtgg ccttgttgat      720
gagcaggctt ggctgatgc gattgagtcc ggtcacattc gtggcgctgg tttcgatgtg       780
tactccaccg agccttgcac tgattctcct ttgttcaagt tgcctcaggt tgttgtgact      840
cctcacttgg gtgcttctac tgaagaggct caggatcgtg cgggtactga cgttgctgat      900
tctgtgctca aggcgctggc tggcgagttc gtggcggatg ctgtgaacgt ttccggtggt      960
cgcgtgggcg aaaaggttgc tgtgtggatg gatctggctc gcaagcttgg tcttcttgct     1020
ggcaagcttg tcgacgccgc cccagtctcc attgaggttg aggctcgagg cgagcttttct    1080 tccgagcagg tcgatgcact tggtttgtcc gctgttcgtg gtttgttctc cggaattatc     1140
gaagagtccg ttactttcgt caacgctcct cgcattgctg aagagcgtgg cctggacatc     1200
tccgtgaaga ccaactctga gtctgttact caccgttccg tcctgcaggt caaggtcatt     1260
actggcagcg gcgcgagcgc aactgttgtt ggtgccctga ctggtcttga gcgcgttgag     1320
aagatcaccc gcatcaatgg ccgtggcctg gatctgcgcg cagagggtct gaacctcttc     1380
ctgcagtaca ctgacgctcc tggtgcactg ggtaccgttg gtaccaagct gggtgctgct     1440
ggcatcaaca tcgaggctgc tgccgttgact caggctgaga agggtgacgg cgctgtcctg    1500
atcctgcgtg ttgagtccgc tgtctctgaa gagctggaag ctgaaatcaa cgctgagttg    1560
ggtgctactt ccttccaggt tgatcttgac taa                                  1593
```

<210> SEQ ID NO 15
<211> LENGTH: 1002
<212> TYPE: DNA
<213> ORGANISM: Artificial Sequence
<220> FEATURE:
<223> OTHER INFORMATION: serA*(197 delta)

<400> SEQUENCE: 15

```
atgagccaga atggccgtcc ggtagtcctc atcgccgata agcttgcgca gtccactgtt      60
gacgcgcttg gagatgcagt agaagtccgt tgggttgacg gacctaaccg cccagaactg     120
cttgatgcag ttaaggaagc ggacgcactg ctcgtgcgtt ctgctaccac tgtcgatgct     180
gaagtcatcg ccgctgcccc taacttgaag atcgtcggtc gtgccggcgt gggcttggac     240
aacgttgaca tccctgctgc cactgaagct ggcgtcatgg ttgctaacgc accgacctct     300
aatattcact ccgcttgtga gcacgcaatt tctttgctgc tgtctactgc tcgccagatc     360
cctgctgctg atgcgacgct gcgtgagggc gagtggaagc ggtcttcttt caacggtgtg     420
gaaattttcg gaaaaactgt cggtatcgtc ggttttggcc acattggtca gttgtttgct     480
cagcgtcttg ctgcgtttga gaccaccatt gttgcttacg atccttacgc taaccctgct     540
cgtgcggctc agctgaacgt tgagttggtt gagttggatg agctgatgag ccgttctgac     600
tttgtcacca ttcaccttcc taagaccaag gaaactgctg gcatgtttga tgcgcagctc     660
cttgctaagt ccaagaaggg ccagatcatc atcaacgctg ctcgtggtgg ccttgttgat     720
gagcaggctt tggctgatgc gattgagtcc ggtcacattc gtggcgctgg tttcgatgtg     780
tactccaccg agccttgcac tgattctcct ttgttcaagt tgcctcaggt tgttgtgact     840
cctcacttgg gtgcttctac tgaagaggct caggatcgtg cgggtactga cgttgctgat     900
tctgtgctca aggcgctggc tggcgagttc gtggcggatg ctgtgaacgt tccggtggt     960
cgcgtgggcg aagaggttgc tgtgtggatg gatctggctt aa                      1002
```

<210> SEQ ID NO 16
<211> LENGTH: 969
<212> TYPE: DNA
<213> ORGANISM: Escherichia coli K12 W3110
<220> FEATURE:
<221> NAME/KEY: gene
<222> LOCATION: (1)..(969)
<223> OTHER INFORMATION: serB

<400> SEQUENCE: 16

```
atgcctaaca ttacctggtg cgacctgcct gaagatgtct ctttatggcc gggtctgcct      60
ctttcattaa gtggtgatga agtgatgcca ctggattacc acgcaggtcg tagcggctgg     120
ctgctgtatg tcgtgggct ggataaacaa cgtctgaccc aataccagag caaactgggt     180
gcggcgatgg tgattgttgc cgcctggtgc gtggaagatt atcaggtgat cgtctggca     240
ggttcactca ccgcacgggc tacacgcctg gcccacgaag cgcagctgga tgtcgccccg     300
ctggggaaaa tcccgcacct gcgcacgccg ggtttgctgg tgatggatat ggactccacc     360
gccatccaga ttgaatgtat tgatgaaatt gccaaactgg ccggaacggg cgagatggtg     420
gcggaagtaa ccgaacgggc gatgcgcggc gaactcgatt ttaccgccag cctgcgcagc     480
cgtgtggcga cgctgaaagg cgctgacgcc aatattctgc aacaggtgcg tgaaaatctg     540
ccgctgatgc aggcttaac gcaactggtg ctcaagctgg aaacgctggg ctggaaagtg     600
gcgattgcct ccggcggctt tacttctctt gctgaatacc tgcgcgacaa gctgcgcctg     660
```

```
accgccgtgg tagccaatga actggagatc atggacggta aatttaccgg caatgtgatc    720
ggcgacatcg tagacgcgca gtacaaagcg aaaactctga ctcgcctcgc gcaggagtat    780
gaaatcccgc tggcgcagac cgtggcgatt ggcgatggag ccaatgacct gccgatgatc    840
aaagcggcag gctggggat tgcctaccat gccaagccaa aagtgaatga aaaggcggaa     900
gtcaccatcc gtcacgctga cctgatgggg gtattctgca tcctctcagg cagcctgaat    960
cagaagtaa                                                             969

<210> SEQ ID NO 17
<211> LENGTH: 1233
<212> TYPE: DNA
<213> ORGANISM: Escherichia coli K12 W3110
<220> FEATURE:
<221> NAME/KEY: gene
<222> LOCATION: (1)..(1233)
<223> OTHER INFORMATION: serA

<400> SEQUENCE: 17
atggcaaagg tatcgctgga aaagacaag attaagtttc tgctggtaga aggcgtgcac      60
caaaaggcgc tggaaagcct tcgtgcagct ggttacacca acatcgaatt tcacaaaggc    120
gcgctggatg atgaacaatt aaaagaatcc atccgcgatg cccacttcat cggcctgcga    180
tcccgtaccc atctgactga agacgtgatc aacgccgcag aaaaactggt cgctattggc    240
tgtttctgta tcgaacaaa ccaggttgat ctggatgcgg cggcaaagcg cgggatcccg    300
gtatttaacg caccgttctc aaatacgcgc tctgttgcgg agctggtgat ggcgaactg    360 ctgctgctat tgcgcggcgt gccggaagcc aatgctaaag cgcaccgtgg cgtgtggaac    420
aaactggcgg cgggttcttt tgaagcgcgc ggcaaaaagc tgggtatcat cggctacggt    480
catattggta cgcaattggg cattctggct gaatcgctgg aatgtatgt ttactttat    540 gatattgaaa ataaactgcc gctgggcaac gccactcagg tacagcatct ttctgacctg    600
ctgaatatga gcgatgtggt gagtctgcat gtaccagaga atccgtccac caaaaatatg    660
atgggcgcga agaaatttc actaatgaag cccggctcgc tgctgattaa tgcttcgcgc    720
ggtactgtgg tggatattcc ggcgctgtgt gatgcgctgg cgagcaaaca tctggcgggg    780
gcggcaatcg acgtattccc gacggaaccg gcgaccaata gcgatccatt tacctctccg    840
ctgtgtgaat tcgacaacgt ccttctgacg ccacacattg gcggttcgac tcaggaagcg    900
caggagaata tcggcctgga agttgcgggt aaattgatca gtattctgaa caatggctca    960
acgctctctg cggtgaactt cccggaagtc tcgctgccac tgcacggtgg cgtcgtctg   1020 atgcacatcc acgaaaaccg tccgggcgtg ctaactgcgc tgaacaaaat cttcgccgag   1080
cagggcgtca acatcgccgc gcaatatctg caaacttccg cccagatggg ttatgtggtt   1140
attgatattg aagccgacga agacgttgcc gaaaaagcgc tgcaggcaat gaaagctatt   1200
ccgggtacca ttcgcgcccg tctgctgtac taa                                1233

<210> SEQ ID NO 18
<211> LENGTH: 1233
<212> TYPE: DNA
<213> ORGANISM: Artificial Sequence
<220> FEATURE:
<223> OTHER INFORMATION: serA*(G336V)

<400> SEQUENCE: 18
atggcaaagg tatcgctgga aaagacaag attaagtttc tgctggtaga aggcgtgcac      60
caaaaggcgc tggaaagcct tcgtgcagct ggttacacca acatcgaatt tcacaaaggc    120
```

```
gcgctggatg atgaacaatt aaaagaatcc atccgcgatg cccacttcat cggcctgcga      180
tcccgtaccc atctgactga agacgtgatc aacgccgcag aaaaactggt cgctattggc      240
tgtttctgta tcggaacaaa ccaggttgat ctggatgcgg cggcaaagcg cgggatcccg      300
gtatttaacg caccgttctc aaatacgcgc tctgttgcgg agctggtgat tggcgaactg      360
ctgctgctat tgcgcggcgt gccggaagcc aatgctaaag cgcaccgtgg cgtgtggaac      420
aaactggcgg cgggttcttt tgaagcgcgc ggcaaaaagc tgggtatcat cggctacggt      480
catattggta cgcaattggg cattctggct gaatcgctgg gaatgtatgt ttactttat       540 gatattgaaa ataaactgcc gctgggcaac gccactcagg tacagcatct ttctgacctg      600
ctgaatatga gcgatgtggt gagtctgcat gtaccagaga atccgtccac caaaaatatg      660
atgggcgcga aagaaatttc actaatgaag cccggctcgc tgctgattaa tgcttcgcgc      720
ggtactgtgg tggatattcc ggcgctgtgt gatgcgctgg cgagcaaaca tctggcgggg      780
gcggcaatcg acgtattccc gacggaaccg cgaccaata gcgatccatt tacctctccg      840
ctgtgtgaat tcgacaacgt ccttctgacg ccacacattg gcggttcgac tcaggaagcg      900
caggagaata tcggcctgga agttgcgggt aaattgatca agtattctga caatggctca      960
acgctctctg cggtgaactt cccggaagtc tcgctgccac tgcacgttgg cgtcgtctg     1020 atgcacatcc acgaaaaccg tccgggcgtg ctaactgcgc tgaacaaaat cttcgccgag    1080
cagggcgtca acatcgccgc gcaatatctg caaacttccg cccagatggg ttatgtggtt    1140
attgatattg aagccgacga agacgttgcc gaaaaagcgc tgcaggcaat gaaagctatt    1200
ccgggtacca ttcgcgcccg tctgctgtac taa                                 1233
```

<210> SEQ ID NO 19
<211> LENGTH: 1233
<212> TYPE: DNA
<213> ORGANISM: Artificial Sequence
<220> FEATURE:
<223> OTHER INFORMATION: serA*(G336V,G337V)

<400> SEQUENCE: 19

```
atggcaaagg tatcgctgga gaaagacaag attaagtttc tgctggtaga aggcgtgcac       60
caaaaggcgc tggaaaagcct tcgtgcagct ggttacacca acatcgaatt tcacaaaggc     120
gcgctggatg atgaacaatt aaaagaatcc atccgcgatg cccacttcat cggcctgcga      180
tcccgtaccc atctgactga agacgtgatc aacgccgcag aaaaactggt cgctattggc      240
tgtttctgta tcggaacaaa ccaggttgat ctggatgcgg cggcaaagcg cgggatcccg      300
gtatttaacg caccgttctc aaatacgcgc tctgttgcgg agctggtgat tggcgaactg      360
ctgctgctat tgcgcggcgt gccggaagcc aatgctaaag cgcaccgtgg cgtgtggaac      420
aaactggcgg cgggttcttt tgaagcgcgc ggcaaaaagc tgggtatcat cggctacggt      480
catattggta cgcaattggg cattctggct gaatcgctgg gaatgtatgt ttactttat       540 gatattgaaa ataaactgcc gctgggcaac gccactcagg tacagcatct ttctgacctg      600
ctgaatatga gcgatgtggt gagtctgcat gtaccagaga atccgtccac caaaaatatg      660
atgggcgcga aagaaatttc actaatgaag cccggctcgc tgctgattaa tgcttcgcgc      720
ggtactgtgg tggatattcc ggcgctgtgt gatgcgctgg cgagcaaaca tctggcgggg      780
gcggcaatcg acgtattccc gacggaaccg cgaccaata gcgatccatt tacctctccg      840
ctgtgtgaat tcgacaacgt ccttctgacg ccacacattg gcggttcgac tcaggaagcg      900
```

| | |
|---|---|
| caggagaata tcggcctgga agttgcgggt aaattgatca agtattctga caatggctca | 960 |
| acgctctctg cggtgaactt cccggaagtc tcgctgccac tgcacgttgt gcgtcgtctg | 1020 |
| atgcacatcc acgaaaaccg tccgggcgtg ctaactgcgc tgaacaaaat cttcgccgag | 1080 |
| cagggcgtca acatcgccgc gcaatatctg caaacttccg cccagatggg ttatgtggtt | 1140 |
| attgatattg aagccgacga agacgttgcc gaaaaagcgc tgcaggcaat gaaagctatt | 1200 |
| ccgggtacca ttcgcgcccg tctgctgtac taa | 1233 |

```
<210> SEQ ID NO 20
<211> LENGTH: 1233
<212> TYPE: DNA
<213> ORGANISM: Artificial Sequence
<220> FEATURE:
<223> OTHER INFORMATION: serA*(G336V,R338G)

<400> SEQUENCE: 20
```

| | |
|---|---|
| atggcaaagg tatcgctgga gaaagacaag attaagtttc tgctggtaga aggcgtgcac | 60 |
| caaaaggcgc tggaaagcct tcgtgcagct ggttacacca catcgaatt tcacaaaggc | 120 |
| gcgctggatg atgaacaatt aaaagaatcc atccgcgatg cccacttcat cggcctgcga | 180 |
| tcccgtaccc atctgactga agacgtgatc aacgccgcag aaaaactggt cgctattggc | 240 |
| tgtttctgta tcggaacaaa ccaggttgat ctggatgcgg cggcaaagcg cgggatcccg | 300 |
| gtatttaacg caccgttctc aaatacgcgc tctgttgcgg agctggtgat tggcgaactg | 360 |
| ctgctgctat tgcgcggcgt gccggaagcc aatgctaaag cgcaccgtgg cgtgtggaac | 420 |
| aaactggcgg cgggttcttt tgaagcgcgc ggcaaaaagc tgggtatcat cggctacggt | 480 |
| catattggta cgcaattggg cattctggct gaatcgctgg gaatgtatgt ttactttat | 540 |
| gatattgaaa ataaactgcc gctgggcaac gccactcagg tacagcatct ttctgacctg | 600 |
| ctgaatatga gcgatgtggt gagtctgcat gtaccagaga tccgtccac caaaaatatg | 660 |
| atgggcgcga aagaaatttc actaatgaag cccggctcgc tgctgattaa tgcttcgcgc | 720 |
| ggtactgtgg tggatattcc ggcgctgtgt gatgcgctgg cgagcaaaca tctggcgggg | 780 |
| gcggcaatcg acgtattccc gacggaaccg gcgaccaata gcgatccatt tacctctccg | 840 |
| ctgtgtgaat tcgacaacgt ccttctgacg ccacacattg gcggttcgac tcaggaagcg | 900 |
| caggagaata tcggcctgga agttgcgggt aaattgatca agtattctga caatggctca | 960 |
| acgctctctg cggtgaactt cccggaagtc tcgctgccac tgcacgttgt gggtcgtctg | 1020 |
| atgcacatcc acgaaaaccg tccgggcgtg ctaactgcgc tgaacaaaat cttcgccgag | 1080 |
| cagggcgtca acatcgccgc gcaatatctg caaacttccg cccagatggg ttatgtggtt | 1140 |
| attgatattg aagccgacga agacgttgcc gaaaaagcgc tgcaggcaat gaaagctatt | 1200 |
| ccgggtacca ttcgcgcccg tctgctgtac taa | 1233 |

```
<210> SEQ ID NO 21
<211> LENGTH: 1089
<212> TYPE: DNA
<213> ORGANISM: Escherichia coli K12 W3110
<220> FEATURE:
<221> NAME/KEY: gene
<222> LOCATION: (1)..(1089)
<223> OTHER INFORMATION: serC

<400> SEQUENCE: 21
```

| | |
|---|---|
| atggctcaaa tcttcaattt tagttctggt ccggcaatgc taccggcaga ggtgcttaaa | 60 |
| caggctcaac aggaactgcg cgactggaac ggtcttggta cgtcggtgat ggaagtgagt | 120 |

```
caccgtggca aagagttcat tcaggttgca gaggaagccg agaaggattt tcgcgatctt    180
cttaatgtcc cctccaacta caaggtatta ttctgccatg gcggtggtcg cggtcagttt    240
gctgcggtac cgctgaatat tctcggtgat aaaaccaccg cagattatgt tgatgccggt    300
tactgggcgg caagtgccat taagaagcg aaaaaatact gcacgcctaa tgtctttgac     360
gccaaagtga ctgttgatgg tctgcgcgcg gttaagccaa tgcgtgaatg caactctct    420 gataatgctg cttatatgca ttattgcccg aatgaaacca tcgatggtat cgccatcgac    480
gaaacgccag acttcggcgc agatgtggtg gtcgccgctg acttctcttc aaccattctt    540
tcccgtccga ttgacgtcag ccgttatggt gtaatttacg ctggcgcgca gaaaaatatc    600
ggcccggctg gcctgacaat cgtcatcgtt cgtgaagatt tgctgggcaa agcgaatatc    660
gcgtgtccgt cgattctgga ttattccatc ctcaacgata acggctccat gtttaacacg    720
ccgccgacat ttgcctggta tctatctggt ctggtcttta aatggctgaa agcgaacggc    780
ggtgtagctg aaatggataa aatcaatcag caaaaagcag aactgctata tggggtgatt    840
gataacagcg atttctaccg caatgacgtg gcgaaagcta accgttcgcg gatgaacgtg    900
ccgttccagt tggcggacag tgcgcttgac aaattgttcc ttgaagagtc ttttgctgct    960
ggccttcatg cactgaaagg tcaccgtgtg gtcggcggaa tgcgcgcttc tatttataac   1020
gccatgccgc tggaaggcgt taaagcgctg acagacttca tggttgagtt cgaacgccgt   1080
cacggttaa                                                           1089

<210> SEQ ID NO 22
<211> LENGTH: 26
<212> TYPE: DNA
<213> ORGANISM: Artificial Sequence
<220> FEATURE:
<223> OTHER INFORMATION: primer for deletion cassette of serB

<400> SEQUENCE: 22
gcgatatcat gaccttagaa tggtgg                                          26

<210> SEQ ID NO 23
<211> LENGTH: 23
<212> TYPE: DNA
<213> ORGANISM: Artificial Sequence
<220> FEATURE:
<223> OTHER INFORMATION: primer for deletion cassette of serB

<400> SEQUENCE: 23
gctctagatc acgcatgcct cgc                                             23

<210> SEQ ID NO 24
<211> LENGTH: 30
<212> TYPE: DNA
<213> ORGANISM: Artificial Sequence
<220> FEATURE:
<223> OTHER INFORMATION: primer for deletion cassette of serB

<400> SEQUENCE: 24
gcgatatcat gtcacccctg tgaaaatgac                                      30

<210> SEQ ID NO 25
<211> LENGTH: 29
<212> TYPE: DNA
<213> ORGANISM: Artificial Sequence
<220> FEATURE:
<223> OTHER INFORMATION: primer for deletion cassette of serB
```

```
<400> SEQUENCE: 25
gctctagatc agttcgatac ctggggtat                              29

<210> SEQ ID NO 26
<211> LENGTH: 24
<212> TYPE: DNA
<213> ORGANISM: Artificial Sequence
<220> FEATURE:
<223> OTHER INFORMATION: primer for deletion cassette of serB

<400> SEQUENCE: 26
atcatgttac tggcaggcgc tatc                                   24

<210> SEQ ID NO 27
<211> LENGTH: 29
<212> TYPE: DNA
<213> ORGANISM: Artificial Sequence
<220> FEATURE:
<223> OTHER INFORMATION: primer for deletion cassette of serB

<400> SEQUENCE: 27
gctctagatt acaaagtgaa agagagacg                              29

<210> SEQ ID NO 28
<211> LENGTH: 26
<212> TYPE: DNA
<213> ORGANISM: Artificial Sequence
<220> FEATURE:
<223> OTHER INFORMATION: primer for construction of serA*

<400> SEQUENCE: 28
acgatatcat gagccagaat ggccgt                                 26

<210> SEQ ID NO 29
<211> LENGTH: 28
<212> TYPE: DNA
<213> ORGANISM: Artificial Sequence
<220> FEATURE:
<223> OTHER INFORMATION: primer for construction of serA*

<400> SEQUENCE: 29
cgtctagatt agtcaagatc aacctgga                               28

<210> SEQ ID NO 30
<211> LENGTH: 41
<212> TYPE: DNA
<213> ORGANISM: Artificial Sequence
<220> FEATURE:
<223> OTHER INFORMATION: primer for construction of serA*(E325K)

<400> SEQUENCE: 30
atccatccac acagcaacct tttcgcccac gcgaccaccg g                41

<210> SEQ ID NO 31
<211> LENGTH: 41
<212> TYPE: DNA
<213> ORGANISM: Artificial Sequence
<220> FEATURE:
<223> OTHER INFORMATION: primer for construction of serA*(E325K)

<400> SEQUENCE: 31
ccggtggtcg cgtgggcgaa aaggttgctg tgtggatgga t                41

<210> SEQ ID NO 32
<211> LENGTH: 31
```

-continued

```
<212> TYPE: DNA
<213> ORGANISM: Artificial Sequence
<220> FEATURE:
<223> OTHER INFORMATION: primer for construction of serA* (197 delta)

<400> SEQUENCE: 32
cgtctagatt aagccagatc catccacaca g                                    31

<210> SEQ ID NO 33
<211> LENGTH: 70
<212> TYPE: DNA
<213> ORGANISM: Artificial Sequence
<220> FEATURE:
<223> OTHER INFORMATION: primer for deletion cassette of serB

<400> SEQUENCE: 33
atgcctaaca ttacctggtg cgacctgcct gaagatgtct ctttatggcc gtgtaggctg     60
gagctgcttc                                                            70

<210> SEQ ID NO 34
<211> LENGTH: 70
<212> TYPE: DNA
<213> ORGANISM: Artificial Sequence
<220> FEATURE:
<223> OTHER INFORMATION: primer for deletion cassette of serB

<400> SEQUENCE: 34
ggatggcggg ccaccaatta cttctgattc aggctgcctg agaggatgca catatgaata    60
tcctccttag                                                            70

<210> SEQ ID NO 35
<211> LENGTH: 27
<212> TYPE: DNA
<213> ORGANISM: Artificial Sequence
<220> FEATURE:
<223> OTHER INFORMATION: primer for amplification of pself-serB to
      construct pBAC-pself-serB

<400> SEQUENCE: 35
cccaagcttc ttccaccctt tgaaaat                                         27

<210> SEQ ID NO 36
<211> LENGTH: 27
<212> TYPE: DNA
<213> ORGANISM: Artificial Sequence
<220> FEATURE:
<223> OTHER INFORMATION: primer for amplification of pself-serB to
      construct pBAC-pself-serB

<400> SEQUENCE: 36
cccaagcttt tacttctgat tcaggct                                         27

<210> SEQ ID NO 37
<211> LENGTH: 19
<212> TYPE: DNA
<213> ORGANISM: Artificial Sequence
<220> FEATURE:
<223> OTHER INFORMATION: primer for amplification of pself-CTG-serB to
      construct pBAC-pself-CTG-serB

<400> SEQUENCE: 37
ggagccttac tgcctaaca                                                  19

<210> SEQ ID NO 38
<211> LENGTH: 19
```

```
<212> TYPE: DNA
<213> ORGANISM: Artificial Sequence
<220> FEATURE:
<223> OTHER INFORMATION: primer for amplification of pself-CTG-serB to
      construct pBAC-pself-CTG-serB

<400> SEQUENCE: 38
tgttaggcag taaggctcc                                              19

<210> SEQ ID NO 39
<211> LENGTH: 20
<212> TYPE: DNA
<213> ORGANISM: Artificial Sequence
<220> FEATURE:
<223> OTHER INFORMATION: primer for construction of serA*

<400> SEQUENCE: 39
agggcgtggt gaccgataat                                             20

<210> SEQ ID NO 40
<211> LENGTH: 28
<212> TYPE: DNA
<213> ORGANISM: Artificial Sequence
<220> FEATURE:
<223> OTHER INFORMATION: primer for construction of serA*

<400> SEQUENCE: 40
cctagagctc cattctggct gaatcgct                                    28

<210> SEQ ID NO 41
<211> LENGTH: 26
<212> TYPE: DNA
<213> ORGANISM: Artificial Sequence
<220> FEATURE:
<223> OTHER INFORMATION: primer for construction of serA*

<400> SEQUENCE: 41
acggatcccc cctgagactg actgtt                                      26

<210> SEQ ID NO 42
<211> LENGTH: 37
<212> TYPE: DNA
<213> ORGANISM: Artificial Sequence
<220> FEATURE:
<223> OTHER INFORMATION: primer for construction of serA*(G336V)

<400> SEQUENCE: 42
tctcgctgcc actgcacgtt gggcgtcgtc tgatgca                          37

<210> SEQ ID NO 43
<211> LENGTH: 37
<212> TYPE: DNA
<213> ORGANISM: Artificial Sequence
<220> FEATURE:
<223> OTHER INFORMATION: primer for construction of serA*(G336V)

<400> SEQUENCE: 43
tgcatcagac gacgcccaac gtgcagtggc agcgaga                          37

<210> SEQ ID NO 44
<211> LENGTH: 37
<212> TYPE: DNA
<213> ORGANISM: Artificial Sequence
<220> FEATURE:
<223> OTHER INFORMATION: primer for construction of serA*(G336V, G337V)

<400> SEQUENCE: 44
```

```
cgctgccact gcacgttgtg cgtcgtctga tgcacat                                    37

<210> SEQ ID NO 45
<211> LENGTH: 37
<212> TYPE: DNA
<213> ORGANISM: Artificial Sequence
<220> FEATURE:
<223> OTHER INFORMATION: primer for construction of serA*(G336V, G337V)

<400> SEQUENCE: 45
atgtgcatca gacgacgcac aacgtgcagt ggcagcg                                    37

<210> SEQ ID NO 46
<211> LENGTH: 37
<212> TYPE: DNA
<213> ORGANISM: Artificial Sequence
<220> FEATURE:
<223> OTHER INFORMATION: primer for construction of serA*(G336V, R338G)

<400> SEQUENCE: 46
ctgccactgc acgttgtggg tcgtctgatg cacatcc                                    37

<210> SEQ ID NO 47
<211> LENGTH: 37
<212> TYPE: DNA
<213> ORGANISM: Artificial Sequence
<220> FEATURE:
<223> OTHER INFORMATION: primer for construction of serA*(G336V, R338G)

<400> SEQUENCE: 47
ggatgtgcat cagacgaccc acaacgtgca gtggcag                                    37

<210> SEQ ID NO 48
<211> LENGTH: 28
<212> TYPE: DNA
<213> ORGANISM: Artificial Sequence
<220> FEATURE:
<223> OTHER INFORMATION: primer for amplification of serA to construct
      pCL-Prmf-serA

<400> SEQUENCE: 48
gatatcatgg caaaggtatc gctggaga                                              28

<210> SEQ ID NO 49
<211> LENGTH: 26
<212> TYPE: DNA
<213> ORGANISM: Artificial Sequence
<220> FEATURE:
<223> OTHER INFORMATION: primer for amplification of serA to construct
      pCL-Prmf-serA

<400> SEQUENCE: 49
aagcttttag tacagcagac gggcgc                                                26

<210> SEQ ID NO 50
<211> LENGTH: 24
<212> TYPE: DNA
<213> ORGANISM: Artificial Sequence
<220> FEATURE:
<223> OTHER INFORMATION: primer for amplification of serA to construct
      pCL-Prmf-serC

<400> SEQUENCE: 50
gatatcatgg ctcaaatctt caat                                                  24
```

```
<210> SEQ ID NO 51
<211> LENGTH: 27
<212> TYPE: DNA
<213> ORGANISM: Artificial Sequence
<220> FEATURE:
<223> OTHER INFORMATION: primer for amplification of serA to construct
      pCL-Prmf-serC

<400> SEQUENCE: 51
cccaagcttt taaccgtgac ggcgttc                                          27

<210> SEQ ID NO 52
<211> LENGTH: 24
<212> TYPE: DNA
<213> ORGANISM: Artificial Sequence
<220> FEATURE:
<223> OTHER INFORMATION: primer for amplification of serA to construct
      pCL-Prmf-serA-(RBS)serC

<400> SEQUENCE: 52
aagcttacgc aacgtggtga gggg                                             24

<210> SEQ ID NO 53
<211> LENGTH: 70
<212> TYPE: DNA
<213> ORGANISM: Artificial Sequence
<220> FEATURE:
<223> OTHER INFORMATION: primer for deletion cassette of phnCDE

<400> SEQUENCE: 53
atgcaaacga ttatccgtgt cgagaagctc gccaaaacct tcaatcagca gtgtaggctg      60
gagctgcttc                                                             70

<210> SEQ ID NO 54
<211> LENGTH: 70
<212> TYPE: DNA
<213> ORGANISM: Artificial Sequence
<220> FEATURE:
<223> OTHER INFORMATION: primer for deletion cassette of phnCDE

<400> SEQUENCE: 54
tcagataaag tgcttacgca accgttgaga gaggaaatcc agcaggctga catatgaata      60
tcctccttag                                                             70

<210> SEQ ID NO 55
<211> LENGTH: 70
<212> TYPE: DNA
<213> ORGANISM: Artificial Sequence
<220> FEATURE:
<223> OTHER INFORMATION: primer for deletion cassette of phoA

<400> SEQUENCE: 55
gtgaaacaaa gcactattgc actggcactc ttaccgttac tgtttacccc gtgtaggctg      60
gagctgcttc                                                             70

<210> SEQ ID NO 56
<211> LENGTH: 70
<212> TYPE: DNA
<213> ORGANISM: Artificial Sequence
<220> FEATURE:
<223> OTHER INFORMATION: primer for deletion cassette of phoA

<400> SEQUENCE: 56
ttatttcagc cccagagcgg ctttcatggt gtagaagaga tcggtctggt catatgaata      60
```

-continued tcctccttag                                                         70

<210> SEQ ID NO 57
<211> LENGTH: 70
<212> TYPE: DNA
<213> ORGANISM: Artificial Sequence
<220> FEATURE:
<223> OTHER INFORMATION: primer for deletion cassette of aphA

<400> SEQUENCE: 57
atgcgcaaga tcacacaggc aatcagtgcc gtttgcttat tgttcgctct gtgtaggctg    60
gagctgcttc                                                         70

<210> SEQ ID NO 58
<211> LENGTH: 70
<212> TYPE: DNA
<213> ORGANISM: Artificial Sequence
<220> FEATURE:
<223> OTHER INFORMATION: primer for deletion cassette of aphA

<400> SEQUENCE: 58
tcagtattct gaattgacga tcacctcttc accaaacgca cccgcttgtg catatgaata    60
tcctccttag                                                         70

<210> SEQ ID NO 59
<211> LENGTH: 70
<212> TYPE: DNA
<213> ORGANISM: Artificial Sequence
<220> FEATURE:
<223> OTHER INFORMATION: primer for promoter replacement cassette of
      pntAB

<400> SEQUENCE: 59
tatcacattc cttaagccaa ttttaatcct gctcaaatga ccgtctatgc aggtgacact    60
atagaacgcg                                                         70

<210> SEQ ID NO 60
<211> LENGTH: 67
<212> TYPE: DNA
<213> ORGANISM: Artificial Sequence
<220> FEATURE:
<223> OTHER INFORMATION: primer for promoter replacement cassette of
      pntAB

<400> SEQUENCE: 60
gcaacacggg tttcattggt taaccgttct cttggtatgc caattcgcat ggtctgtttc    60
ctgtgtg                                                            67

<210> SEQ ID NO 61
<211> LENGTH: 28
<212> TYPE: DNA
<213> ORGANISM: Artificial Sequence
<220> FEATURE:
<223> OTHER INFORMATION: primer for amplification of gdhA to construct
      pcc1BAC-P(native)-gdhA

<400> SEQUENCE: 61
cgaagcttgt ctctgctact gataacgg                                     28

<210> SEQ ID NO 62
<211> LENGTH: 26
<212> TYPE: DNA
<213> ORGANISM: Artificial Sequence
<220> FEATURE:

```
<223> OTHER INFORMATION: primer for amplification of gdhA to construct
      pcc1BAC-P(native)-gdhA

<400> SEQUENCE: 62
cgaagcttgg gagcatcatc cgttaa                                              26

<210> SEQ ID NO 63
<211> LENGTH: 28
<212> TYPE: DNA
<213> ORGANISM: Artificial Sequence
<220> FEATURE:
<223> OTHER INFORMATION: primer for amplification of ydeD to construct
      pCL-Prmf-ydeD

<400> SEQUENCE: 63
aagatatcat gtcgcgaaaa gatggggt                                            28

<210> SEQ ID NO 64
<211> LENGTH: 29
<212> TYPE: DNA
<213> ORGANISM: Artificial Sequence
<220> FEATURE:
<223> OTHER INFORMATION: primer for amplification of ydeD to construct
      pCL-Prmf-ydeD

<400> SEQUENCE: 64
cccaagcttg tgccaatgtc gtggttgtt                                           29

<210> SEQ ID NO 65
<211> LENGTH: 28
<212> TYPE: DNA
<213> ORGANISM: Artificial Sequence
<220> FEATURE:
<223> OTHER INFORMATION: primer for amplification of yfiK to construct
      pCL-Prmf-yfiK

<400> SEQUENCE: 65
aagatatcgt gacaccgacc cttttaag                                            28

<210> SEQ ID NO 66
<211> LENGTH: 29
<212> TYPE: DNA
<213> ORGANISM: Artificial Sequence
<220> FEATURE:
<223> OTHER INFORMATION: primer for amplification of yfiK to construct
      pCL-Prmf-yfiK

<400> SEQUENCE: 66
cccaagctta ccatccgtgt atccggtta                                           29

<210> SEQ ID NO 67
<211> LENGTH: 26
<212> TYPE: DNA
<213> ORGANISM: Artificial Sequence
<220> FEATURE:
<223> OTHER INFORMATION: primer for amplification of rhtB to construct
      pCL-Prmf-rhtB

<400> SEQUENCE: 67
gcgatatcat gaccttagaa tggtgg                                              26

<210> SEQ ID NO 68
<211> LENGTH: 23
<212> TYPE: DNA
<213> ORGANISM: Artificial Sequence
<220> FEATURE:
<223> OTHER INFORMATION: primer for amplification of rhtB to construct
``` pCL-Prmf-rhtB

<400> SEQUENCE: 68
gctctagatc acgcatgcct cgc                                          23

<210> SEQ ID NO 69
<211> LENGTH: 32
<212> TYPE: DNA
<213> ORGANISM: Artificial Sequence
<220> FEATURE:
<223> OTHER INFORMATION: primer for amplification of rhtC to construct
      pCL-Prmf-rhtC

<400> SEQUENCE: 69
gcgatatcat gttgatgtta tttctcaccg tc                                32

<210> SEQ ID NO 70
<211> LENGTH: 32
<212> TYPE: DNA
<213> ORGANISM: Artificial Sequence
<220> FEATURE:
<223> OTHER INFORMATION: primer for amplification of rhtC to construct
      pCL-Prmf-rhtC

<400> SEQUENCE: 70
gctctagatc accgcgaaat aatcaaatga at                                32

<210> SEQ ID NO 71
<211> LENGTH: 24
<212> TYPE: DNA
<213> ORGANISM: Artificial Sequence
<220> FEATURE:
<223> OTHER INFORMATION: primer for amplification of asrB to construct
      pCL-Prmf-asrB

<400> SEQUENCE: 71
atcatgttac tggcaggcgc tatc                                         24

<210> SEQ ID NO 72
<211> LENGTH: 29
<212> TYPE: DNA
<213> ORGANISM: Artificial Sequence
<220> FEATURE:
<223> OTHER INFORMATION: primer for amplification of asrB to construct
      pCL-Prmf-asrB

<400> SEQUENCE: 72
gctctagatt acaaagtgaa agagagacg                                    29

<210> SEQ ID NO 73
<211> LENGTH: 29
<212> TYPE: DNA
<213> ORGANISM: Artificial Sequence
<220> FEATURE:
<223> OTHER INFORMATION: primer for amplification of livHM to construct
      pCL-Prmf-livHM

<400> SEQUENCE: 73
gcgatatcat gtctgagcag tttttgtat                                    29

<210> SEQ ID NO 74
<211> LENGTH: 29
<212> TYPE: DNA
<213> ORGANISM: Artificial Sequence
<220> FEATURE:
<223> OTHER INFORMATION: primer for amplification of livHM to construct
      pCL-Prmf-livHM

<400> SEQUENCE: 74
gctctagatc atgcctgctc tcctttcgc                                          29

<210> SEQ ID NO 75
<211> LENGTH: 70
<212> TYPE: DNA
<213> ORGANISM: Artificial Sequence
<220> FEATURE:
<223> OTHER INFORMATION: primer for deletion cassette of gpmA

<400> SEQUENCE: 75
gtgtaggctg gagctgcttc tataatgaga attattatca ttaaaagatg atttgaggag        60
taagtatatg                                                               70

<210> SEQ ID NO 76
<211> LENGTH: 70
<212> TYPE: DNA
<213> ORGANISM: Artificial Sequence
<220> FEATURE:
<223> OTHER INFORMATION: primer for deletion cassette of gpmA

<400> SEQUENCE: 76
catatgaata tcctccttag tcggctttct cattttaaac gaatgacgtt tacttcgctt        60
taccctggtt                                                               70

<210> SEQ ID NO 77
<211> LENGTH: 26
<212> TYPE: DNA
<213> ORGANISM: Artificial Sequence
<220> FEATURE:
<223> OTHER INFORMATION: primer for amplification of gpmI to construct
      pSG76C-gpmI

<400> SEQUENCE: 77
acggatcccg agcggtcgta tatttt                                             26

<210> SEQ ID NO 78
<211> LENGTH: 43
<212> TYPE: DNA
<213> ORGANISM: Artificial Sequence
<220> FEATURE:
<223> OTHER INFORMATION: primer for amplification of gpmI to construct
      pSG76C-gpmI
      involved stop codon

<400> SEQUENCE: 78
cagcgcggca aatttttctt actattttt cagcgaggat tca                          43

<210> SEQ ID NO 79
<211> LENGTH: 43
<212> TYPE: DNA
<213> ORGANISM: Artificial Sequence
<220> FEATURE:
<223> OTHER INFORMATION: primer for amplification of gpmI to construct
      pSG76C-gpmI involved stop codon

<400> SEQUENCE: 79
tgaatcctcg ctgaaaaaat agtaagaaaa atttgccgcg ctg                          43

<210> SEQ ID NO 80
<211> LENGTH: 28
<212> TYPE: DNA
<213> ORGANISM: Artificial Sequence
<220> FEATURE:

<223> OTHER INFORMATION: primer for amplification of gpmI to construct
pSG76C-gpmI

<400> SEQUENCE: 80
cctagagctc aacgactctt ctacgcca                                28

<210> SEQ ID NO 81
<211> LENGTH: 70
<212> TYPE: DNA
<213> ORGANISM: Artificial Sequence
<220> FEATURE:
<223> OTHER INFORMATION: primer for deletion cassette of gpmB

<400> SEQUENCE: 81
gcatgttaca ggtatacctc gtccgccacg gtgaaacgca gtggaacgcc gtgtaggctg    60
gagctgcttc                                                          70

<210> SEQ ID NO 82
<211> LENGTH: 70
<212> TYPE: DNA
<213> ORGANISM: Artificial Sequence
<220> FEATURE:
<223> OTHER INFORMATION: primer for deletion cassette of gpmB

<400> SEQUENCE: 82 tccctgcgg tttcaacgac ccagccagac gccagccaca ggctttcctg catatgaata    60
tcctccttag                                                          70

<210> SEQ ID NO 83
<211> LENGTH: 70
<212> TYPE: DNA
<213> ORGANISM: Artificial Sequence
<220> FEATURE:
<223> OTHER INFORMATION: primer for deletion cassette of kbl

<400> SEQUENCE: 83
aagtttgggt aatatgtgct ggaatttgcc ctgtctggag aatcgcaatg gtgtaggctg    60
gagctgcttc                                                          70

<210> SEQ ID NO 84
<211> LENGTH: 70
<212> TYPE: DNA
<213> ORGANISM: Artificial Sequence
<220> FEATURE:
<223> OTHER INFORMATION: primer for deletion cassette of kbl

<400> SEQUENCE: 84
agtttggata acgctttcat ctcacatcct caggcgataa cgcccagttg catatgaata    60
tcctccttag                                                          70

<210> SEQ ID NO 85
<211> LENGTH: 73
<212> TYPE: DNA
<213> ORGANISM: Artificial Sequence
<220> FEATURE:
<223> OTHER INFORMATION: primer for deletion cassette of sdaA

<400> SEQUENCE: 85
gtgtattagt tcgttactgg aagtccagtc accttgtcag gagtattatc gtggtgtagg    60
ctggagctgc ttc                                                      73

<210> SEQ ID NO 86

```
<211> LENGTH: 70
<212> TYPE: DNA
<213> ORGANISM: Artificial Sequence
<220> FEATURE:
<223> OTHER INFORMATION: primer for deletion cassette of sdaA

<400> SEQUENCE: 86
atccgttgca gatgggcgag taagaagtat tagtcacact ggactttgat catatgaata    60
tcctccttag                                                            70

<210> SEQ ID NO 87
<211> LENGTH: 70
<212> TYPE: DNA
<213> ORGANISM: Artificial Sequence
<220> FEATURE:
<223> OTHER INFORMATION: primer for deletion cassette of iclR

<400> SEQUENCE: 87
atggtcgcac ccattcccgc gaaacgcggc agaaaacccg ccgttgccac gtgtaggctg    60
gagctgcttc                                                            70

<210> SEQ ID NO 88
<211> LENGTH: 70
<212> TYPE: DNA
<213> ORGANISM: Artificial Sequence
<220> FEATURE:
<223> OTHER INFORMATION: primer for deletion cassette of iclR

<400> SEQUENCE: 88
tcagcgcatt ccaccgtacg ccagcgtcac ttccttcgcc gctttaatca catatgaata    60
tcctccttag                                                            70

<210> SEQ ID NO 89
<211> LENGTH: 21
<212> TYPE: DNA
<213> ORGANISM: Artificial Sequence
<220> FEATURE:
<223> OTHER INFORMATION: primer for amplification of acs to construct
      pCL-Prmf-acs

<400> SEQUENCE: 89
actatgagcc aaattcacaa a                                               21

<210> SEQ ID NO 90
<211> LENGTH: 27
<212> TYPE: DNA
<213> ORGANISM: Artificial Sequence
<220> FEATURE:
<223> OTHER INFORMATION: primer for amplification of acs to construct
      pCL-Prmf-acs

<400> SEQUENCE: 90
cccaagcttt tacgatggca tcgcgat                                         27

<210> SEQ ID NO 91
<211> LENGTH: 24
<212> TYPE: DNA
<213> ORGANISM: Artificial Sequence
<220> FEATURE:
<223> OTHER INFORMATION: primer for amplification of poxB to construct
      pCL-Prmf-poxB

<400> SEQUENCE: 91
actatgaaac aaacggttgc agct                                            24
```

<210> SEQ ID NO 92
<211> LENGTH: 30
<212> TYPE: DNA
<213> ORGANISM: Artificial Sequence
<220> FEATURE:
<223> OTHER INFORMATION: primer for amplification of poxB to construct pCL-Prmf-poxB

<400> SEQUENCE: 92
cccaagcttt taccttagcc agtttgtttt                                    30

<210> SEQ ID NO 93
<211> LENGTH: 21
<212> TYPE: DNA
<213> ORGANISM: Artificial Sequence
<220> FEATURE:
<223> OTHER INFORMATION: primer for amplification of ackA-pta to construct pCL-Prmf-ackA-pta

<400> SEQUENCE: 93
atcatgtcga gtaagttagt a                                             21

<210> SEQ ID NO 94
<211> LENGTH: 27
<212> TYPE: DNA
<213> ORGANISM: Artificial Sequence
<220> FEATURE:
<223> OTHER INFORMATION: primer for amplification of ackA-pta to construct pCL-Prmf-ackA-pta

<400> SEQUENCE: 94
cccaagcttt tactgctgct gtgcaga                                       27

<210> SEQ ID NO 95
<211> LENGTH: 24
<212> TYPE: DNA
<213> ORGANISM: Artificial Sequence
<220> FEATURE:
<223> OTHER INFORMATION: primer for amplification of aceBA to construct pCL-Prmf-aceBA

<400> SEQUENCE: 95
actatgactg aacaggcaac aaca                                          24

<210> SEQ ID NO 96
<211> LENGTH: 30
<212> TYPE: DNA
<213> ORGANISM: Artificial Sequence
<220> FEATURE:
<223> OTHER INFORMATION: primer for amplification of aceBA to construct pCL-Prmf-aceBA

<400> SEQUENCE: 96
cccaagcttc tacgttcggc aacggctgta                                    30

<210> SEQ ID NO 97
<211> LENGTH: 24
<212> TYPE: DNA
<213> ORGANISM: Artificial Sequence
<220> FEATURE:
<223> OTHER INFORMATION: primer for amplification of pckA to construct pCL-Prmf-pckA

<400> SEQUENCE: 97
actatgcgcg ttaacaatgg tttg                                          24

<210> SEQ ID NO 98
<211> LENGTH: 30
<212> TYPE: DNA
<213> ORGANISM: Artificial Sequence
<220> FEATURE:
<223> OTHER INFORMATION: primer for amplification of pckA to construct
      pCL-Prmf-pckA

<400> SEQUENCE: 98
cccaagctta taaacgggag gcgaaggtgc                                    30

<210> SEQ ID NO 99
<211> LENGTH: 24
<212> TYPE: DNA
<213> ORGANISM: Artificial Sequence
<220> FEATURE:
<223> OTHER INFORMATION: primer for amplification of glcB to construct
      pCL-Prmf-glcB

<400> SEQUENCE: 99
atcatgagtc aaaccataac ccag                                          24

<210> SEQ ID NO 100
<211> LENGTH: 30
<212> TYPE: DNA
<213> ORGANISM: Artificial Sequence
<220> FEATURE:
<223> OTHER INFORMATION: primer for amplification of glcB to construct
      pCL-Prmf-glcB

<400> SEQUENCE: 100
cccaagcttt taatgacttt cttttcgcg                                     30

<210> SEQ ID NO 101
<211> LENGTH: 21
<212> TYPE: DNA
<213> ORGANISM: Artificial Sequence
<220> FEATURE:
<223> OTHER INFORMATION: primer for amplification of maeB to construct
      pCL-Prmf-maeB

<400> SEQUENCE: 101
atcatggatg accagttaaa a                                             21

<210> SEQ ID NO 102
<211> LENGTH: 27
<212> TYPE: DNA
<213> ORGANISM: Artificial Sequence
<220> FEATURE:
<223> OTHER INFORMATION: primer for amplification of maeB to construct
      pCL-Prmf-maeB

<400> SEQUENCE: 102
cccaagcttt tacagcggtt gggtttg                                       27

<210> SEQ ID NO 103
<211> LENGTH: 21
<212> TYPE: DNA
<213> ORGANISM: Artificial Sequence
<220> FEATURE:
<223> OTHER INFORMATION: primer for construction of gcl

<400> SEQUENCE: 103
atcatggcaa aaatgagagc c                                             21

<210> SEQ ID NO 104
<211> LENGTH: 23

```
<212> TYPE: DNA
<213> ORGANISM: Artificial Sequence
<220> FEATURE:
<223> OTHER INFORMATION: primer for construction of gcl

<400> SEQUENCE: 104
gcgcaagctt ttattcatag tgc                                           23

<210> SEQ ID NO 105
<211> LENGTH: 22
<212> TYPE: DNA
<213> ORGANISM: Artificial Sequence
<220> FEATURE:
<223> OTHER INFORMATION: primer for construction of glxR-glxK

<400> SEQUENCE: 105
gcgcgatatc atgaaactgg ga                                            22

<210> SEQ ID NO 106
<211> LENGTH: 34
<212> TYPE: DNA
<213> ORGANISM: Artificial Sequence
<220> FEATURE:
<223> OTHER INFORMATION: primer for construction of glxR-glxK

<400> SEQUENCE: 106
ataaactggc ctgatctaga tttgttgaaa aagg                               34

<210> SEQ ID NO 107
<211> LENGTH: 34
<212> TYPE: DNA
<213> ORGANISM: Artificial Sequence
<220> FEATURE:
<223> OTHER INFORMATION: primer for construction of glxR-glxK

<400> SEQUENCE: 107
cctttttcaa caaatctaga tcaggccagt ttat                               34

<210> SEQ ID NO 108
<211> LENGTH: 32
<212> TYPE: DNA
<213> ORGANISM: Artificial Sequence
<220> FEATURE:
<223> OTHER INFORMATION: primer for construction of glxR-glxK

<400> SEQUENCE: 108
ggcaagctta ttgcggccgc ttagtttttta at                                32

<210> SEQ ID NO 109
<211> LENGTH: 29
<212> TYPE: DNA
<213> ORGANISM: Artificial Sequence
<220> FEATURE:
<223> OTHER INFORMATION: forward primer for Ape-OPSS

<400> SEQUENCE: 109
gtcatatgat ggctctggct gacatctct                                     29

<210> SEQ ID NO 110
<211> LENGTH: 29
<212> TYPE: DNA
<213> ORGANISM: Artificial Sequence
<220> FEATURE:
<223> OTHER INFORMATION: reverse primer for Ape-OPSS

<400> SEQUENCE: 110
```
gtaagctttt aaacagagtc accagcacc                              29

<210> SEQ ID NO 111
<211> LENGTH: 29
<212> TYPE: DNA
<213> ORGANISM: Artificial Sequence
<220> FEATURE:
<223> OTHER INFORMATION: forward primer for Mtb-OPSS

<400> SEQUENCE: 111
gtcatatgat gacacgatac gactcgctg                              29

<210> SEQ ID NO 112
<211> LENGTH: 29
<212> TYPE: DNA
<213> ORGANISM: Artificial Sequence
<220> FEATURE:
<223> OTHER INFORMATION: reverse primer for Mtb-OPSS

<400> SEQUENCE: 112
gtaagctttc atgcccatag ttgcccttc                              29

<210> SEQ ID NO 113
<211> LENGTH: 29
<212> TYPE: DNA
<213> ORGANISM: Artificial Sequence
<220> FEATURE:
<223> OTHER INFORMATION: forward primer for Msm-OPSS

<400> SEQUENCE: 113
ataagctttc atgcccatag ctgcccttc                              29

<210> SEQ ID NO 114
<211> LENGTH: 29
<212> TYPE: DNA
<213> ORGANISM: Artificial Sequence
<220> FEATURE:
<223> OTHER INFORMATION: reverse primer for Msm-OPSS

<400> SEQUENCE: 114
ataagctttc attccagcgc gtcctcggc                              29

<210> SEQ ID NO 115
<211> LENGTH: 29
<212> TYPE: DNA
<213> ORGANISM: Artificial Sequence
<220> FEATURE:
<223> OTHER INFORMATION: forward primer for Rjo-OPSS

<400> SEQUENCE: 115
gtcatatgat ggcgcggttc gattcgctg                              29

<210> SEQ ID NO 116
<211> LENGTH: 31
<212> TYPE: DNA
<213> ORGANISM: Artificial Sequence
<220> FEATURE:
<223> OTHER INFORMATION: reverse primer for Rjo-OPSS

<400> SEQUENCE: 116
tagcggccgc tcatgcccac aactgccctt c                           31

<210> SEQ ID NO 117
<211> LENGTH: 29
<212> TYPE: DNA
<213> ORGANISM: Artificial Sequence

```
<220> FEATURE:
<223> OTHER INFORMATION: forward primer for Nfa-OPSS

<400> SEQUENCE: 117
gtcatatgat ggcacgctac gaatcgctg                                29

<210> SEQ ID NO 118
<211> LENGTH: 28
<212> TYPE: DNA
<213> ORGANISM: Artificial Sequence
<220> FEATURE:
<223> OTHER INFORMATION: reverse primer for Nfa-OPSS

<400> SEQUENCE: 118
gtaagctttc aggcccagag ctggcctt                                 28

<210> SEQ ID NO 119
<211> LENGTH: 29
<212> TYPE: DNA
<213> ORGANISM: Artificial Sequence
<220> FEATURE:
<223> OTHER INFORMATION: forward primer for Mtb-T

<400> SEQUENCE: 119
gtcatatgat gacacgatac gactcgctg                                29

<210> SEQ ID NO 120
<211> LENGTH: 29
<212> TYPE: DNA
<213> ORGANISM: Artificial Sequence
<220> FEATURE:
<223> OTHER INFORMATION: reverse primer for Mtb-T

<400> SEQUENCE: 120
gtaagctttc attccagagc ggtctcggc                                29

<210> SEQ ID NO 121
<211> LENGTH: 29
<212> TYPE: DNA
<213> ORGANISM: Artificial Sequence
<220> FEATURE:
<223> OTHER INFORMATION: forward primer of Msm-T

<400> SEQUENCE: 121
gtcatatgat gacgcgctac gactccctg                                29

<210> SEQ ID NO 122
<211> LENGTH: 29
<212> TYPE: DNA
<213> ORGANISM: Artificial Sequence
<220> FEATURE:
<223> OTHER INFORMATION: reverse primer of Msm-T

<400> SEQUENCE: 122
ataagctttc attccagcgc gtcctcggc                                29

<210> SEQ ID NO 123
<211> LENGTH: 21
<212> TYPE: DNA
<213> ORGANISM: Artificial Sequence
<220> FEATURE:
<223> OTHER INFORMATION: forward primer of pCL-P(CJ1)-Msm-T

<400> SEQUENCE: 123
gatatcgcag cagccatcat c                                        21
```

```
<210> SEQ ID NO 124
<211> LENGTH: 28
<212> TYPE: DNA
<213> ORGANISM: Artificial Sequence
<220> FEATURE:
<223> OTHER INFORMATION: reverse primer of pCL-P(CJ1)-Msm-T

<400> SEQUENCE: 124
cccaagcttt cattccagcg cgtcctcg                                          28
```